United States Patent
Curtis

(10) Patent No.: US 6,740,514 B2
(45) Date of Patent: May 25, 2004

(54) NUCLEIC ACIDS CORRESPONDING TO 46798 A NOVEL HUMAN MATRIX METALLOPROTEINASE AND USES THEREOF

(75) Inventor: Rory A. J. Curtis, Southborough, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/950,510

(22) Filed: Sep. 10, 2001

(65) Prior Publication Data

US 2002/0150978 A1 Oct. 17, 2002

Related U.S. Application Data

(60) Provisional application No. 60/231,136, filed on Sep. 8, 2000.

(51) Int. Cl.$^7$ .......................... C12N 9/64; C12N 15/00; C12N 5/00; C07H 21/04

(52) U.S. Cl. .................... 435/226; 435/320.1; 435/325; 435/252.3; 536/23.2; 536/23.5

(58) Field of Search ................................ 435/226, 69.1, 435/320.1, 325, 252.33, 419, 254.2, 348; 536/23.2, 23.5; 530/350

(56) References Cited

U.S. PATENT DOCUMENTS 5,498,539 A  3/1996  Harrison et al.

FOREIGN PATENT DOCUMENTS

| WO | WO 98/40475 A1 | 9/1998 |
|---|---|---|
| WO | WO 01/10903 A2 * | 2/2001 |
| WO | WO 01/40466 A2 | 6/2001 |
| WO | WO 01/55428 A2 * | 8/2001 |
| WO | WO 01/90326 A2 | 11/2001 |

OTHER PUBLICATIONS

Marchenko G. N. et al. MMP–28, a new human matrix metalloproteinase with an unusual cysteine–switch sequence is widely expressed in tumor, Gene, 2001, 265, 87–93.*
Lohi J. et al., Epilysin, a Novel Human Matrix Metalloproteinase (MMP–28) Expressed in Testis and Keratynocytes and in Response to Injury, J. Biol. Chem. 2001, 276, 1134–10144.*
GENBANK® Database, Accession No. AW001264.
GENBANK® Database, Accession No. AI816763.
Manikopoulos, et al., "Performance Analysis of a Gateway Connecting the CEBUS to the ISDN", *IEEE Transactions on Consumer Electronics,* vol. 39, No. 4, pp. 870–877 (1993).
GENBANK® Database, Accession No. AAG41981.
GENBANK® Database, Accession No. AAK01480.
GENBANK® Database, Accession No. AAK01706.
GENBANK® Database, Accession No. AF219624.
GENBANK® Database, Accession No. AF315683.
GENBANK® Database, Accession No. AF330002.
GENBANK® Database, Accession No. NP_077278.
GENBANK® Database, Accession No. NP_116568.
GENBANK® Database, Accession No. XP_039490.
DePaola et al., "Vascular endothelium responds to fluid shear stress gradients," Arteriosclerosis and Thrombosis 12(11):1254–1257 (1992) (Abstract only).
DePaola et al., "Spatial and temporal regulation of gap junction connexin43 in vascular endothelial cells exposed to controlled distrubed flows in vitro," Proc. Natl. Acad. Sci. USA 96:3154–3159 (1999).
Eberwine et al., "An (alysis of gene expression in single live neurons," Proc. Natl. Acad. Sci. USA 89:3010–3014 (1992).
Lohi et al., "Epilysin, a novel human matrix metalloproteinase (MMP–28) expressed in testis and keratinocytes and in response to injury," J. Biolog. Chem. 276(13):10134–10144 (2001).
Marchenko et al., "MMP–28, a new human matrix metalloproteinase with an unusual cysteine–switch sequence is widely expressed in tumors," Gene 265:87–93 (2001).
Nagase et al., "Matrix metalloproteinases," J. Biolog. Chem. 274(31):21491–21494 (1999).
Nagel et al., "Vascular endothelial cells respond to spatial gradients in fluid shear stress by enhanced activation of transcription factors," Arterioscler. Thromb. Vasc. Biol. 19:1825–1834.
Nakashima et al., "Upregulation of VCAM–1 and ICAM–1 at atherosclerosis–prone sites on the endothelium in the ApoE–deficient mouse," Arterioscler. Thromb. Fasc. Biol. 18(5):842–851 (1998).
Topper et al., "Identification of vascular endothelial genes differentially responsive to fluid mechanical stimuli: cyclooxygenase–2, manganese superoxide dismutase, and endothelial cell nitric oxide synthase are selectively up–regulated by steady laminar shear stress," Proc. Natl. Acad. Sci. USA 93:10417–10422 (1996).

(List continued on next page.)

*Primary Examiner*—Rebecca Prouty
*Assistant Examiner*—Malgorzata A. Walicka
(74) *Attorney, Agent, or Firm*—Millennium Pharmaceuticals, Inc.

(57) ABSTRACT

The invention provides isolated nucleic acids molecules, designated 46798 nucleic acid molecules, which encode a novel matrix metalloproteinase. The invention also provides antisense nucleic acid molecules, recombinant expression vectors containing 46798 nucleic acid molecules, host cells into which the expression vectors have been introduced, and non-human transgenic animals in which a 46798 gene has been introduced or disrupted. The invention still further provides isolated 46798 proteins, fusion proteins, antigenic peptides and anti-46798 antibodies. Diagnostic methods utilizing compositions of the invention are also provided.

16 Claims, 12 Drawing Sheets

OTHER PUBLICATIONS

Topper et al., "Expression of the bumetanide–sensitive Na–K–Cl cotransporter BSC2 is differentially regulated by fluid mechanical and inflammatory cytokine stimuli in vascular endothelium," J. Clin. Invest. 99(12):2941–2949 (1997).

Topper et al., "Vascular MADs: two novel MAD–related genes selectively inducible by flow in human vascular endothelium," Proc. Natl. Acad. Sci. USA, 94:9314–9319 (1997).

Walpola, et al., "Expression of ICAM–1 and VCAM–1 and monocyte adherence in arteries exposed to altered shear stress," Arterioscl. Thromb. Vascu. Biol. 15(1):2–10 (1995).

Zarins et al., "Carotid bifurcation atherosclerosis. Quantitative correlation of plaque localization with flow velocity profiles and wall shear stress," Circulation Research, 53:502–514 (1983) (Abstract only).

* cited by examiner

```
GCCGGGCCTCCGCCCCCCTCCGCCTGCCTTTCCTTCCTCCCTCGGTCCCCGGGCCGGGGACCCGCGGGCAGGCA
CTGCCCGGGCTGGACGACGTCTGGCCGCCGGAGGGCAGGAGGAGGCGGCCAGAGCGCGCAGCTAGGGCAC
TGGCGAAACCCGGGACAGTCCCCTCTCCCGTGCGGGGCGGGGCGCAGAGACAGTCCCATCCCCGGGTCCGCGGCTG

M   V   A   R       4
ACTGCCGGCTGGTTCCCTGCGCGCAGTAGCTCCCCGAGCCGGGCTGCACCGGAGGGGCGAG ATG GTC GCG CGC  12

V   G   L   L   R   A   L   Q   L   W   G   H   L   D   A   Q   P       24
GTC GGC CTC CTG CGC GCC CTG CAG CTG TGG GGC CAC CTG GAC GCC CAG CCC          72

A   E   R   G   G   Q   E   L   R   K   E   A   F   L   E   K   Y   G      44
GCG GAG CGC GGA GGC CAG GAG CTG CGC AAG GAG GCA TTC CTA GAG AAG TAC GGA     132

Y   L   N   E   Q   V   S   P   K   A   P   T   S   D   R   A   I   R      64
TAC CTC AAT GAA CAG GTC CCC AAA GCT CCC ACC TCC AGC GAT GCC ATC AGA         192

A   F   Q   W   V   S   Q   L   P   V   T   G   V   L   D   R   A   T   L   R   84
GCG TTT CAG TGG GTG TCC CAG CTA CCT GTC ACA GGC GTT TTG GAC CGC GCC ACC CTG CGC  252

Q   M   T   R   P   R   C   G   V   T   D   T   N   S   Y   A   A   E     104
CAG ATG ACT CGT CCC CGC TGC GGG GTT ACA GAT ACC AAC AGT TAT GCG GCC GAG    312

R   I   S   D   L   F   A   R   H   R   T   K   M   R   K   R   F   A     124
AGG ATC AGT GAC TTG TTT GCT AGA CAC CGG ACC AAA ATG AGG AGG CGT AAA CGC TTT GCA  372

| | | | | | | | | | | | | | | | | | | | | aa | nt |
|---|---|---|---|---|---|---|---|---|---|---|---|---|---|---|---|---|---|---|---|---|---|
| K | Q | N | K | W | Y | K | Q | H | L | S | Y | R | L | V | N | W | P | E | | 144 | 432 |
| AAG | CAA | AAC | AAA | TGG | TAC | AAG | CAG | CAC | CTC | TCC | TAC | CGC | CTG | GTG | AAC | TGG | CCT | GAG | | | |
| H | L | E | P | A | V | F | A | R | L | V | Q | F | N | W | S | | | | | 164 | 492 |
| CAT | CTG | GAG | CCG | GCA | GTT | TTC | GCC | CGC | CTG | GTG | CAG | TTC | AAC | TGG | AGC | | | | | | |
| V | S | A | E | L | W | E | T | A | R | A | P | G | I | R | L | | | | | 184 | 552 |
| GTC | TCA | GCG | GAG | CTG | TGG | GAG | ACA | GCC | CGC | GCT | CCC | GGC | ATC | CGG | CTC | | | | | | |
| F | F | Q | G | D | N | A | H | F | D | P | Q | G | G | E | A | | | | | 204 | 612 |
| TTC | TTC | CAA | GGG | GAC | AAT | GCC | CAC | TTT | GAT | CCC | CAA | GGC | GGG | GAG | GCC | | | | | | |
| L | A | H | R | F | L | R | G | E | H | F | Q | D | E | D | G | | | | | 224 | 672 |
| CTG | GCG | CAC | CGC | TTC | CTG | CGC | GGC | GAA | CAC | TTC | CAG | GAC | GAG | GAT | GCC | | | | | | |
| S | L | R | R | G | N | R | F | V | L | A | H | E | I | G | H | | | | | 244 | 732 |
| TCC | CTG | CGC | CGC | GGG | AAC | CGC | TTC | GTG | CTG | GCG | CAC | GAG | ATC | GGT | CAC | | | | | | |
| T | L | G | S | P | H | L | A | R | M | P | Y | Y | K | R | | | | | | 264 | 792 |
| ACG | CTT | GGC | TCG | CCC | CAC | CTG | GCG | ATG | CCC | TAC | TAC | AAG | CGG | | | | | | | | |
| L | R | D | A | L | W | D | V | L | A | Q | S | L | Y | G | E | | | | | 284 | 852 |
| CTG | CGC | GAC | GCG | CTC | AGC | TGG | GAC | GTG | GCC | CAG | AGC | CTG | TAT | GGG | GAG | | | | | | |
| K | P | L | G | K | P | G | Q | V | A | S | V | L | F | T | D | F | | | | 304 | 912 |
| AAG | CCC | CTA | GGG | AAG | CCA | GGA | CAG | GTC | GCC | TCA | GTG | CTG | TTC | ACT | GAC | TTT | | | | | |

| | | | | | | | | | | | | | | | | | | | | | |
|---|---|---|---|---|---|---|---|---|---|---|---|---|---|---|---|---|---|---|---|---|---|
| T | W | D | S | Y | S | P | Q | G | R | R | P | E | T | Q | G | P | K | Y | C | 324 | |
| ACC | TGG | GAC | TCC | TAC | AGC | CCC | CAA | GGA | AGG | CGC | CCT | GAA | ACG | CAG | GGC | CCT | AAA | TAC | TGC | | 972 |
| H | S | F | D | A | I | T | V | D | R | Q | Q | L | I | Y | F | K | G | 344 | |
| CAC | TCT | TTC | GAT | GCC | ATC | ACT | GTA | GAC | AGG | CAA | CAG | CTG | ATT | TAC | TTT | AAA | GGG | | 1032 |
| S | H | F | W | E | V | A | A | D | G | N | S | E | Q | Q | R | P | L | Q | E | 364 | |
| AGC | CAT | TTC | TGG | GAG | GTG | GCA | GCT | GAT | GGC | AAC | TCA | GAG | CAA | CAG | CGT | CCA | CTG | CAG | GAA | | 1092 |
| R | W | V | G | L | P | P | N | I | E | A | A | V | S | L | N | D | G | 384 | |
| AGA | TGG | GTC | GGG | CTG | CCC | CCC | AAC | ATT | GAG | GCT | GCA | GTG | TCA | TTG | AAT | GAT | GGA | | 1152 |
| F | Y | F | K | C | R | G | R | W | F | R | G | P | K | P | G | V | 404 | |
| TTC | TAC | TTC | AAA | TGC | CGA | GGG | AGG | TGG | TTC | CGG | GGC | CCC | AAG | CCA | GGT | GTG | | 1212 |
| L | Q | L | C | R | A | G | L | I | L | P | R | H | P | D | A | A | L | F | 424 | |
| CTG | CAG | CTG | TGC | CGG | GCA | GGG | CTC | ATC | CTC | CCC | CGC | CAT | CCT | GAC | GCC | GCC | CTC | TTC | | 1272 |
| P | P | R | R | L | F | K | G | A | Y | R | Y | A | R | V | G | 444 | |
| CCT | CCT | CGC | CGC | CTC | TTC | AAG | GGT | GCC | TAC | CGC | TAC | GCC | CGA | GTG | GGG | | 1332 |
| G | L | Q | V | E | P | Y | P | R | S | L | Q | D | W | G | P | I | E | 464 | |
| GGA | CTG | CAA | GTG | GAG | CCC | TAC | CCC | CGA | AGT | CTG | CAG | GAC | TGG | GGA | GGC | ATC | CCT | GAG | | 1392 |

Fig. 1C

```
E   V   S   G   A   L   P   R   P   D   G   S   I   I   F   F   R   D   D   R    484
GAG GTC AGC GGC GCC CTG CCG AGG CCC GAT GGC TCC ATC ATC TTC TTC CGA GAT GAC CGC  1452

Y   W   R   L   D   Q   A   K   L   Q   A   T   T   S   G   R   W   A   T   E    504
TAC TGG CGC CTC GAC CAG GCC AAA CTG CAG GCA ACC ACC TCG GGC CGC TGG GCC ACC GAG  1512

L   P   W   M   G   C   W   H   A   N   S   G   S   A   L   F   *                521
CTG CCC TGG ATG GGC TGC TGG CAT GCC AAC TCG GGG AGC GCC CTG TTC TGA              1563

AGGCACCTCCTCACCTCAGAAACTGGTGGTGCTCTCAGGGCAAAATCATGTTCCCCACCCCGGGGCAGAACCCCTCTT
AGAAGCCCTCTGAGTCCCTGTCTGTGTCTGCCCTTGTCTGCCCCACCACATGGAGGCCAGCAGTCTGTGCCTTTGTTCCTTGAAG
AATGCAGCATTGTCTGTCTGCCCTTGTCTGCCCTTGTCTGCCCTTGTCTGCCCCACCACATGGAGGTGGGATCAATCTTAGGAAAAGCAAAAAGGGTCC
CAGATCCCTTGGCCCTTCCTCCGAGGACTTCTATCCTCCCCAGGCCTTTGTTTTTTCGGCTAAAGGTACAGTTCCTTT
CAAGAGGTAACAGACAGGGGATCCAAGCACTGGGATGAAAAACTCAGCAGAGAAATTCGAGACCATTTGCAAGACTGT
GCCCTTCCTCCAGGACCCCCTGGCTCAGTGTTCTTGAAAAACGGTGTCATATTTAGTCAGGAGGCCCCACCCCCAGGAAGC
ATGGATGGGGATGAAGGCACAGGCGTCTCCAAGCCTCAAAGCCCTTTGTGGGGCTGGAATAAAGAGGTGCCTTCAGCTGGAGACT
GATGCAGGCCTACCAGTCCCTGGCTTTTTGTCTGGGCTGGAATAAAGAGGTGCCTTCAGCTGGTGGGCCGAGAGGCAG
GAAGCAGCCTTCCTTGGAAAAAAAAAAAAAAAAA
```

Fig. 1D

```
GTCGACCCAC GCGTCCGGCC GGGCCTCCCG CCCCTCCGCC TGCCTTTCCT TCCTCCCTCC
CTCGGTCCCC GGGGCCGGCG GACCCGCGGG CAGGCACTGC CCGGGCTGGA CGACGTCTGG
CCGGCTCCCG GCGAAGGGCA GCGGAGGAGC GCCCAGAGC GCGCAGCTAG GGCACTGGCG
AAACCCCGGG ACAGTCCCTC TCCGTGCGGG GGCGGCGCAG AGCAGTCCCA TCCCCGGGGT
CCCGGGCGCG GCTGACTGCC GGCTGGTTCC CTGCGCGCAG TAGCTCCCCG AGCCGGGCTG
CACCGGAGGC GGCGAGATGG TCGCGCGCGT CGGCCTCCTG CTGCGCGCCC TGCAGCTGCT
ACTGTGGGGC CACCTGGACG CCCAGCCCGC GGAGCGCGGA GGCCAGGAGC TGCGCAAGGA
GGCGGAGGCA TTCCTAGAGA AGTACGGATA CCTCAATGAA CAGGTCCCCA AAGCTCCCAC
CTCCACTCGA TTCAGCGATG CCATCAGAGC GTTTCAGTGG GTGTCCCAGC TACCTGTCAG
CGGCGTGTTG GACCGCGCCA CCCTGCGCCA GATGACTCGT CCCCGCTGCG GGGTTACAGA
TACCAACAGT TATGCGGCCT GGGCTGAGAG GATCAGTGAC TTGTTTGCTA GACACCGGAC
CAAAATGAGG CGTAAGAAAC GCTTTGCAAA GCAAGGGGGC GCCCTGGCGC ACGCCTTCCT
GCCCCGCCGC GGCGAAGCGC ACTTCGACCA AGATGAGCGC TGGTCCCCTGA GCCGCCGCCG
CGGGCGCAAC CTGTTCGTGG TGCTGCGCA CGAGATCGGT CACACGCTTG GCCTCACCCA
CTCGCGCGCG CCGCGCGCGC TCATGGCGCC CTACTACAAG AGGCTGGGGC GCGACGCGCT
GCTCAGCTGG GACGACGTGC TGGCCGTGCA GAGCCTGCA CACTGACTTT GGGAAGCCCC TAGGGGGCTC
AGTGGCCGTC CAGGCTCCCAG GAAAAGCTGTT CACTGACTTT GAGACCCTGG ACTCCTACAG
CCCCAAGGA AGGCGCCCTG AAACGCAGGG CCCTAAATAC TGCCACTCTT CCTTCGATGC
CATCACTGTA GACAACGAAC AGCAACTGTA CATTTTAAA GGGAGCCATT TCTGGAGGT
GGCAGCTGAT GGCAACGTCT CAGAGCCCCG TCCACTGCAG GAAAGATGGG TCGGGCTGCC
CCCCAACATT GAGGCTGCGG CAGTGTCATT GAATGATGGA GATTTCTACT TCTTCAAAGG
GGGTCGATGC TGGAGGTTCC GGGCCCCAA GCCAGTGTGG GGTCTCCCAC AGCTGTGCCG
GGCAGGGGGC CTGCCCCGCC ATCCTGACGC CGCCCCTCTTC TTCCCTCCTC TGCGCCGCCT
```

FIG. 3A

```
CATCCTCTTC AAGGGTGCCC GCTACTACGT GCTGGCCCGA GGGGGACTGC AAGTGGAGCC
CTACTACCCC CGAAGTCTGC AGGACTGGGG AGGCATCCCT GAGGAGGTCA GCGGCGCCCT
GCCGAGGCCC GATGGCTCCA TCATCTTCTT CCGAGATGAC CGCTACTGGC GCCTCGACCA
GGCCAAACTG CAGGCAACCA CCTCGGGCCG CTGGGCCACC GAGCTGCCCT GGATGGGCTG
CTGGCATGCC AACTCGGGGA GCGCCCTGTT CTGAAGGCAC CTCCTCACCT CAGAAACTGG
TGGTGCTCTC AGGGCAAAAT CATGTTCCCC ACCCCCGGGG CAGAACCCCT CTTAGAAGCC
TCTGAGTCCC TCTGCAGAAG ACCGGGCAGC AAAGCCTCCA TCTGGAAGTC TGTCTGCCTT
TGTTCCTTGA AGAATGCAGC ATTGTCTTTG TCTGTCCCCA CCACATGGAG GTGGGGTGG
GATCAATCTT AGGAAAAGCA AAAAAGGGTC CCAGATCCCT TGGCCCTTTC CTCCGAGGAC
TTCTATCCTC CCCAGGCCTT TGTTTCTTCG CAGTTCCTTT CAAGAGGTAA
CAGCACTGGG ATCCAAGCAG AACTCAGCAG AGAAATTCGA GACCATTTTG
CAAGACTGTG CCCTTCTCCT CAGGACCCCC TGGCTCAGTT CTTGAAAAAC GGTGTCATAT
TTAGTCAGAG GCCCCACCCC CAGGAAGCAT GGATGGGGAT GAAGGCACAG GCGTCTCCAA
CCTCAGAGGC CCTTTGTGGG GTCAGGACAC AGAGTGGGAG GGAGACTGAT GCAGGCCTAC
CAGTCCCTGG CTTTTTGTCT GGGGCTGGAA TAAAGAGGTG CCTTTCAGCT GTGGGCCGAG
AAAAAAAAAA GGGCGGCCGC
```

FIG. 3B

MVARVGLLLRALQLLLWGHLDAQPAERGGQELRKEAEAFLEKYGYLNEQVPKAPTSTRFS
DAIRAFQWVSQLPVSGVLDRATLRQMTRPRCGVTDTNSYAAWAERISDLFARHRTKMRRK
KRFAKQGGALAHAFLPRRGEAHFDQDERWSLSRRRGRNLFVVLAHEIGHTLGLTHSPAPR
ALMAPYYKRLGRDALLSWDDVLAVQSLYGKPLGGSVAVQLPGKLFTDFETWDSYSPQGRR
PETQGPKYCHSSFDAITVDRQQQLYIFKGSHFWEVAADGNVSEPRPLQERWVGLPPNIEA
AAVSLNDGDFYFFKGGRCWRFRGPKPVWGLPQLCRAGGLPRHPDAALFFPPLRRLILFKG
ARYYVLARGGLQVEPYYPRSLQDWGGIPEEVSGALPRPDGSIIFFRDDRYWRLDQAKLQA
TTSGRWATELPWMGCWHANSGSALF

FIG. 3C

```
              1              15 16              30 31              45 46              60
MMP19         ---------------  ---------------  ---------------  ------KAPTSTRFS
PMIM23        MVARVGLLLRALQLL  LWGHLDAQPAERGGQ  ELRKEAEAFLEKYGY  LNEQVPKAPTSTRFS
LONG          MVARVGLLLRALQLL  LWGHLDAQPAERGGQ  ELRKEAEAFLEKYGY  LNEQVPKAPTSTRFS
SHORT         MVARVGLLLRALQLL  LWGHLDAQPAERGGQ  ELRKEAEAFLEKYGY  LNEQVPKAPTSTRFS
ISO-1         MVARVGLLLRALQLL  LWGHLDAQPAERGGQ  ELRKEAEAFLEKYGY  LNEQVPKAPTSTRFS
ISO-2         MVARVGLLLRALQLL  LWGHLDAQPAERGGQ  ELRKEAEAFLEKYGY  LNEQVPKAPTSTRFS 61             75 76             90 91            105 106            120
MMP19         DAIRAFQWVSQLPVS  GVLDRANLRQMTRPR  CGVTDTNSYAAWAER  ISDLFARHRTKMRRK
PMIM23        DAIRAFQWVSQLPVS  GVLDRATLRQMTRPR  CGVTDTNSYAAWAER  ISDLFARHRTKMRRK
LONG          DAIRAFQWVSQLPVS  GVLDRATLRQMTRPR  CGVTDTNSYAAWAER  ISDLFARHRTKMRRK
SHORT         DAIRAFQWVSQLPVS  GVLDRATLRQMTRPR  CGVTDTNSYAAWAER  ISDLFARHRTKMRRK
ISO-1         DAIRAFQWVSQLPVS  GVLDRATLRQMTRPR  CGVTDTNSYAAWAER  ISDLFARHRTKMRRK
ISO-2         DAIRAFQWVSQLPVS  GVLDRATLRQMTRPR  CGVTDTNSYAAWAER  ISDLFARHRTKMRRK 121           135 136           150 151           165 166           180
MMP19         KRFAKQGNKWYKQHL  SYRLVNWPEHLPEPA  VRGAVRAAFQLWSNV  SALEFWEAPATGPAD
PMIM23        KRFAKQGNKWYKQHL  SYRLVNWPEHLPEPA  VRGAVRAAFQLWSNV  SALEFWEAPATGPAD
LONG          KRFAKQGNKWYKQHL  SYRLVNWPEHLPEPA  VRGAVRAAFQLWSNV  SALEFWEAPATGPAD
SHORT         KRFAKQ---------  ---------------  ---------------  ---------------
ISO-1         KRFAKQGNKWYKQHL  SYRLVNWPEHLPEPA  VRGAVRAAFQLWSNV  SALEFWEAPATGPAD
ISO-2         KRFAKQGNKWYKQHL  SYRLVNWPEHLPEPA  VRGAVRAAFQLWSNV  SALEFWEAPATGPAD
```

FIG. 5A

|         | 181                | 195 | 196           | 210 | 211           | 225 | 226            | 240 |
|---------|--------------------|-----|---------------|-----|---------------|-----|----------------|-----|
| MMP19   | IRLTFFQGDHNDGLG    |     | NAFDGPGGALAHAFL |   | PRRGEAHFDQDERWS |   | LSRRRGRNLFVVLAH |   |
| PMIM23  | IRLTFFQGDHNDGLG    |     | NAFDGPGGALAHAFL |   | PRRGEAHFDQDERWS |   | LSRRRGRNLFVVLAH |   |
| LONG    | IRLTFFQGDHNDGLG    |     | NAFDGPGGALAHAFL |   | PRRGEAHFDQDERWS |   | LSRRRGRNLFVVLAH |   |
| SHORT   | ---------------    |     | -----GGALAHAFL  |   | PRRGEAHFDQDERWS |   | LSRRRGRNLFVVLAH |   |
| ISO-1   | IRLTFFQGDHNDGLG    |     | NAFDGPGGALAHAFL |   | PRRGEAHFDQDERWS |   | LSRRRGRNLFVVLAH |   |
| ISO-2   | IRLTFFQGDHNDGLG    |     | NAFDGPGGALAHAFL |   | PRRGEAHFDQDERWS |   | LSRRRGRNLFVVLAH |   |

|         | 241                | 255 | 256           | 270 | 271           | 285 | 286            | 300 |
|---------|--------------------|-----|---------------|-----|---------------|-----|----------------|-----|
| MMP19   | EIGHTLGLTHSPAPR    |     | ALMAPYYKRLGRDAL |   | LSWDDVLAVQSLYGK |   | PLGGSVAVQLPGKLF |   |
| PMIM23  | EIGHTLGLTHSPAPR    |     | ALMAPYYKRLGRDAL |   | LSWDDVLAVQSLYGK |   | PLGGSVAVQLPGKLF |   |
| LONG    | EIGHTLGLTHSPAPR    |     | ALMAPYYKRLGRDAL |   | LSWDDVLAVQSLYGK |   | PLGGSVAVQLPGKLF |   |
| SHORT   | EIGHTLGLTHSPAPR    |     | ALMAPYYKRLGRDAL |   | LSWDDVLAVQSLYGK |   | PLGGSVAVQLPGKLF |   |
| ISO-1   | EIGHTLGLTHSPAPR    |     | ALMAPYYKRLGRDAL |   | LSWDDVLAVQSLYGK |   | PLGGSVAVQLPGKLF |   |
| ISO-2   | EIGHTLGLTHSPAPR    |     | ALMAPYYKRLGRDAL |   | LSWDDVLAVQSLYGK |   | PLGGSVAVQLPGKLF |   |

|         | 301                | 315 | 316           | 330 | 331           | 345 | 346            | 360 |
|---------|--------------------|-----|---------------|-----|---------------|-----|----------------|-----|
| MMP19   | TDFETWDSYSPQGRR    |     | PETQGPKYCHSSFDA |   | ITVDRQQQLYIFKGS |   | HFWEVAADGNVSEPR |   |
| PMIM23  | TDFETWDSYSPQGRR    |     | PETQGPKYCHSSFDA |   | ITVDRQQQLYIFKGS |   | HFWEVAADGNVSEPR |   |
| LONG    | TDFETWDSYSPQGRR    |     | PETQGPKYCHSSFDA |   | ITVDRQQQLYIFKGS |   | HFWEVAADGNVSEPR |   |
| SHORT   | TDFETWDSYSPQGRR    |     | PETQGPKYCHSSFDA |   | ITVDRQQQLYIFKGS |   | HFWEVAADGNVSEPR |   |
| ISO-1   | TDFETWDSYSPQGRR    |     | PETQGPKYCHSSFDA |   | ITVDRQQQLYIFKGS |   | HFWEVAADGNVSEPR |   |
| ISO-2   | TDFETWDSYSPQGRR    |     | PETQGPKYCHSSFDA |   | ITVDRQQQLYIFKGS |   | HFWEVAADGNVSEPR |   |

FIG. 5B

```
        361           375 376           390 391           405 406           420
MMP19   PLQERWVGLPPNIEA AAVSLNDGDFYFFKG GRCWRFRGPKPVWGL PQLCRAGGLPRHPDA
PMIM23  PLQERWVGLPPNIEA AAVSLNDGDFYFFKG GRCWRFRGPKPVWGL PQLCRAGGLPRHPDA
LONG    PLQERWVGLPPNIEA AAVSLNDGDFYFFKG GRCWRFRGPKPVWGL PQLCRAGGLPRHPDA
SHORT   PLQERWVGLPPNIEA AAVSLNDGDFYFFKG GRCWRFRGPKPVWGL PQLCRAGGLPRHPDA
ISO-1   PLQERWVGLPPNIEA AAVSLNDGDFYFFKG GRCWRFRGPKPVWGL PQLCRAGGLPRHPDA
ISO-2   PLQERWVGLPPNIEA AAVSLNDGDFYFFKV QSV------------ ---------------

421           435 436           450 451           465 466           480
MMP19   ALFFPPLRRLILFKG ARYYVLARGGLQVEP YYPRSLQDWGGIPEE VSGALPRPDGSIIFF
PMIM23  ALFFPPLRRLILFKG ARYYVLARGGLQVEP YYPRSLQDWGGIPEE VSGALPRPDGSIIFF
LONG    ALFFPPLRRLILFKG ARYYVLARGGLQVEP YYPRSLQDWGGIPEE VSGALPRPDGSIIFF
SHORT   ALFFPPLRRLILFKG ARYYVLARGGLQVEP YYPRSLQDWGGIPEE VSGALPRPDGSIIFF
ISO-1   ALFFPPLRRLILFKG ARYYVLARGGLQVEP YYPRSLQDWGGIPEE VSGALPRPDGSIIFF
ISO-2   --------------- --------------- --------------- ---------------

481           495 496           510 511
MMP19   RDDRYWRLDQAKLQA TTSGRWATELPWMGC WHANSGSALF
PMIM23  RDDRYWRLDQAKLQA TTSGRWATELPWMGC WHANSGSALF
LONG    RDDRYWRLDQAKLQA TTSGRWATELPWMGC WHANSGSALF
SHORT   RDDRYWRLDQAKLQA TTSGRWATELPWMGC WHANSGSALF
ISO-1   RDDRYWRLDQAKLQA TTSGRWATELPWMGC WHANSGSALF
ISO-2   --------------- --------------- ----------
```

FIG. 5C

– NUCLEIC ACIDS CORRESPONDING TO 46798 A NOVEL HUMAN MATRIX METALLOPROTEINASE AND USES THEREOF

CROSS-REFERENCE TO RELATED APPLICATIONS

This application is entitled to priority pursuant to 35 U.S.C. §119(e) to U.S. provisional patent application 60/231,136, which was filed on Sep. 8, 2000.

STATEMENT REGARDING FEDERALLY SPONSORED RESEARCH OR DEVELOPMENT

Not Applicable

REFERENCE TO MICROFICHE APPENDIX

Not Applicable

BACKGROUND OF THE INVENTION

Degradation of extracellular matrix (ECM) is critical for normal embryonic development, blastocyst implantation, organ morphogenesis, nerve growth, ovulation, cervical dilatation, postpartum uterine involution, endometrial cycling, hair follicle cycling, bone remodeling, wound healing, angiogenesis, apoptosis, and numerous other normal physiological processes. Aberrant degradation of ECM is associated with numerous disease states including, for example, tissue invasion and metastasis by tumor cells, aberrant angiogenesis, cardiovascular diseases (e.g., heart failure and atherosclerosis), arthritis, nephritis, neurological diseases (e.g., macular degeneration), breakdown of the blood-brain barrier, periodontal disease, skin ulceration, gastric ulceration, corneal ulceration, liver fibrosis, emphysema, fibrotic lung disease, and other pathological conditions.

Secreted proteinases of the extracellular matrix metalloproteinase (MMP) gene family are essential for maintaining the architecture of tissues and organs. MMPs are sometimes designated 'matrixins,' and catalyze degradation of ECM. The protein degradative activity of MMPs can be modulated by endogenous inhibitors, alpha-macroglobulins, and tissue inhibitors of metalloproteinases (TIMPs). In addition, expression of most MMPs is transcriptionally regulated by one or more growth factors, hormones, and cytokines, and tends to be differentially regulated during various phases of cellular transformation.

MMPs are generally synthesized in the form of catalytically inactive pre-pro-enzymes, and secreted in the form of inactive pro-enzymes. Pro-MMPs can be activated in vitro using various proteases, thiol-reactive agents, mercurial compounds, reactive oxygen, and denaturing agents. In vivo, pro-MMPs are believed to be activated by removal of the propeptide domain, catalyzed by tissue or plasma proteinases, or sometimes by opportunistic bacterial proteinases. In vivo activation of pro-MMPs is believed to occur primarily at cell surfaces.

Although a primary function of MMPs is catalysis of simple removal (i.e., resorption) of ECM, MMPs can also alter the biological activity exhibited by ECM components. For example, MMP-2 released from neurite growth cones inactivates neurite growth-inhibiting chondroitin sulfate proteoglycans and uncovers laminin (which enhances neurite growth). Other normal and pathological processes in which MMP-catalyzed changes in ECM protein structures have been implicated are described, for example in Nagase et al. (1999, J. Biol. Chem. 274:21491–21494).

No fewer than 23 classes of MMPs, characterized by no fewer than eight characteristic domain arrangements, have been described. In view of the widespread and critical nature of MMP activities in normal and pathological physiological processes, a need exists for identification of further members of this protein family. The present invention satisfies this need by providing a novel human MMP.

BRIEF SUMMARY OF THE INVENTION

The present invention is based, in part, on the discovery of a novel gene encoding an MMP, the gene being referred to herein as "46798". cDNAs encoding 46798 have been isolated in at least two different forms, herein designated the 'short' and 'long' forms. The nucleotide sequence of a cDNA encoding the long form of 46798 is shown in SEQ ID NO: 1, and the amino acid sequence of the long form of the 46798 polypeptide is shown in SEQ ID NO: 2. In addition, the nucleotide sequence of the coding region is depicted in SEQ ID NO: 3. The nucleotide sequence of a cDNA encoding the short form of 46798 is shown in SEQ ID NO: 11, and the amino acid sequence of the short form of the 46798 polypeptide is shown in SEQ ID NO: 12. In addition, the nucleotide sequence of the coding region is depicted in SEQ ID NO: 13. The short and long forms of 46798 are individually and collectively referred to herein as '46798 proteins' or '46798 nucleic acids.'

Accordingly, in one aspect, the invention features a nucleic acid molecule that encodes a 46798 protein or polypeptide, e.g., a biologically active portion of the 46798 protein. In a preferred embodiment the isolated nucleic acid molecule encodes a polypeptide having the amino acid sequence of either of SEQ ID NOs: 2 and 12. In other embodiments, the invention provides isolated 46798 nucleic acid molecules having the nucleotide sequence of one of SEQ ID NOs: 1, 3, 11, and 13. In still other embodiments, the invention provides nucleic acid molecules that have sequences that are substantially identical (e.g., naturally occurring allelic variants) to the nucleotide sequence of one of SEQ ID NOs: 1, 3, 11, and 13. In other embodiments, the invention provides a nucleic acid molecule which hybridizes under stringent hybridization conditions with a nucleic acid molecule having a sequence comprising the nucleotide sequence of one of SEQ ID NOs: 1, 3, 11, and 13, wherein the nucleic acid encodes a full length 46798 protein or an active fragment thereof.

In a related aspect, the invention further provides nucleic acid constructs that include a 46798 nucleic acid molecule described herein. In certain embodiments, the nucleic acid molecules of the invention are operatively linked to native or heterologous regulatory sequences. Also included are vectors and host cells containing the 46798 nucleic acid molecules of the invention, e.g., vectors and host cells suitable for producing 46798 nucleic acid molecules and polypeptides.

In another related aspect, the invention provides nucleic acid fragments suitable as primers or hybridization probes for detection of 46798-encoding nucleic acids.

In still another related aspect, isolated nucleic acid molecules that are antisense to a 46798-encoding nucleic acid molecule are provided.

In another aspect, the invention features 46798 polypeptides, and biologically active or antigenic fragments thereof that are useful, e.g., as reagents or targets in assays applicable to treatment and diagnosis of 46798-mediated or related disorders (e.g., MMP-mediated disorders such as those described herein). In another embodiment, the invention provides 46798 polypeptides having matrix metalloproteinase activity. Preferred polypeptides are 46798 proteins including at least one MMP domain, and preferably having a 46798 activity, e.g., a 46798 activity as described herein. Preferred polypeptides are 46798 proteins including at least one transmembrane domain and at least one peptidase_M10 domain.

In other embodiments, the invention provides 46798 polypeptides, e.g., a 46798 polypeptide having the amino acid sequence shown in one of SEQ ID NOs: 2 and 12; an amino acid sequence that is substantially identical to the amino acid sequence shown in one of SEQ ID NOs: 2 and 12; or an amino acid sequence encoded by a nucleic acid molecule having a nucleotide sequence which hybridizes under stringent hybridization conditions to a nucleic acid molecule comprising the nucleotide sequence of any of SEQ ID NOs: 1, 3, 11, and 13, wherein the nucleic acid encodes a full length 46798 protein or an active fragment thereof.

In a related aspect, the invention further provides nucleic acid constructs that include a 46798 nucleic acid molecule described herein.

In a related aspect, the invention provides 46798 polypeptides or fragments operatively linked to non-46798 polypeptides to form fusion proteins.

In another aspect, the invention features antibodies and antigen-binding fragments thereof, that react with, or more preferably, specifically bind, 46798 polypeptides.

In another aspect, the invention provides methods of screening for compounds that modulate the expression or activity of the 46798 polypeptides or nucleic acids.

In still another aspect, the invention provides a process for modulating 46798 polypeptide or nucleic acid expression or activity, e.g., using the screened compounds. In certain embodiments, the methods involve treatment of conditions related to aberrant activity or expression of the 46798 polypeptides or nucleic acids, such as conditions involving aberrant or deficient degradation or resorption of ECM proteins or aberrant or deficient proteolytic activation of extracellular matrix proteins.

The invention also provides assays for determining the activity of or the presence or absence of 46798 polypeptides or nucleic acid molecules in a biological sample, including for disease diagnosis.

In further aspect the invention provides assays for determining the presence or absence of a genetic alteration in a 46798 polypeptide or nucleic acid molecule, including for disease diagnosis.

Other features and advantages of the invention will be apparent from the following detailed description, and from the claims.

BRIEF DESCRIPTION OF THE SEVERAL VIEWS OF THE DRAWINGS

FIG. 1 depicts a cDNA sequence (SEQ ID NO: 1) and predicted amino acid sequence (SEQ ID NO: 2) of long form human 46798. The methionine-initiated open reading frame of long form human 46798 (without the 5'- and 3'-non-translated regions) starts at nucleotide 300 of SEQ ID NO: 1, and the coding region (not including the terminator codon; shown in SEQ ID NO: 3) extends through nucleotide 1859 of SEQ ID NO: 1.

FIG. 3, comprising FIGS. 3A though C, is a cDNA sequence (FIGS. 3A through 3B; SEQ ID NO: 11) and predicted amino acid sequence (FIG. 3C; SEQ ID NO: 12) of short form human 46798. The methionine-initiated open reading frame of short form human 46798 (without the 5'- and 3'-non-translated regions) starts at nucleotide 317 of SEQ ID NO: 11, and the coding region (not including the terminator codon; shown in SEQ ID NO: 13) extends through nucleotide 1652 of SEQ ID NO: 11.

FIG. 5, comprising FIGS. 5A through 5C, is an alignment of the amino acid sequence of long form human 46798 ("long"; SEQ ID NO: 2), short form human 46798 ("short"; SEQ ID NO: 12), matrix metalloproteinase 19 ("MMP19"; SEQ ID NO: 23), PPIM23 ("PPIM23"; SEQ ID NO: 24); matrix metalloproteinase 28 (MMP-28) isoform 1 ("iso 1"; SEQ ID NO: 21), and MMP-28 isoform 2 ("iso 2"; SEQ ID NO: 22), made using the CLUSTALW software and its default settings. The amino acid sequence "MMP19" corresponds to the amino acid sequence in International publication number WO 98/40475 designated SEQ ID NO: 10. The amino acid sequence "PPIM23" corresponds to the amino acid sequence in International publication number WO 01/10903 designated SEQ ID NO: 23. MMP-28 isoform 1 corresponds to GENPEPT® accession number NP_077278 and MMP-28 isoform 2 corresponds to GENPEPT® accession number NP_116568. The ClustalW software is available commercially and at various World Wide Web addresses, and default parameters used at any of those sites can be used.

DETAILED DESCRIPTION OF THE INVENTION

Figure 2:
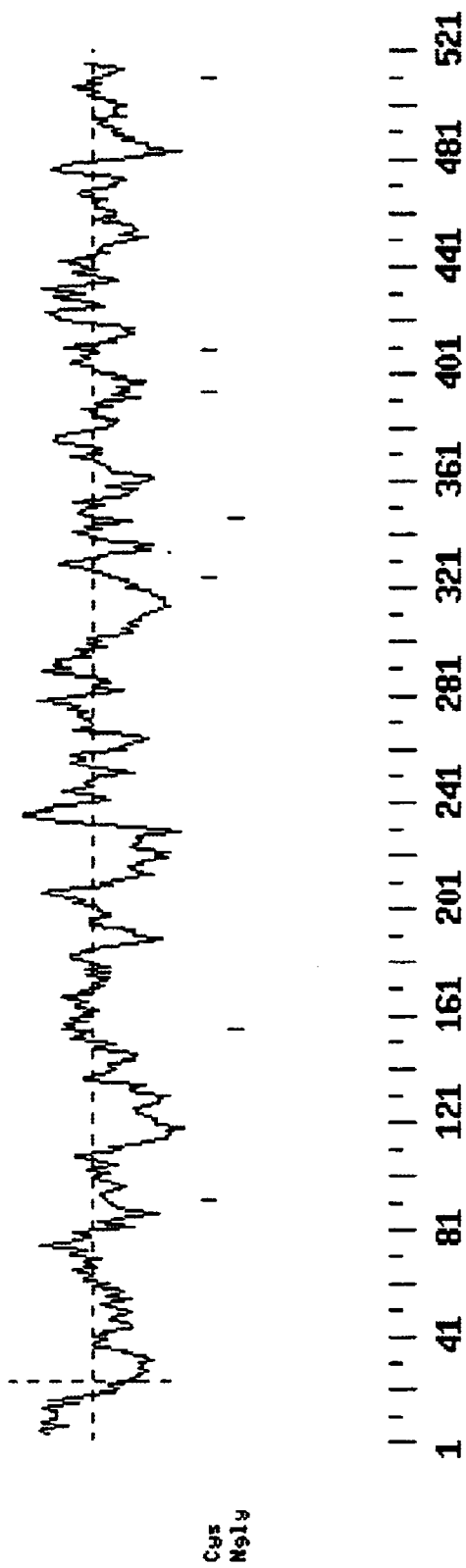
FIG. 2 depicts a hydropathy plot of long form human 46798. Relatively hydrophobic residues are shown above the dashed horizontal line, and relative hydrophilic residues are below the dashed horizontal line. The cysteine residues (cys) are indicated by short vertical lines below the hydropathy trace. The numbers corresponding to the amino acid sequence of human 46798 are indicated. Polypeptides of the invention include fragments which include: all or part of a hydrophobic sequence, i.e., a sequence above the dashed line, e.g., the sequence of about residues 230–250 of SEQ ID NO: 2; all or part of a hydrophilic sequence, i.e., a sequence below the dashed line, e.g., the sequence of residues 210–230 or 300–320 of SEQ ID NO: 2; a sequence which includes a cysteine residue; or a glycosylation site.
Figure 4:
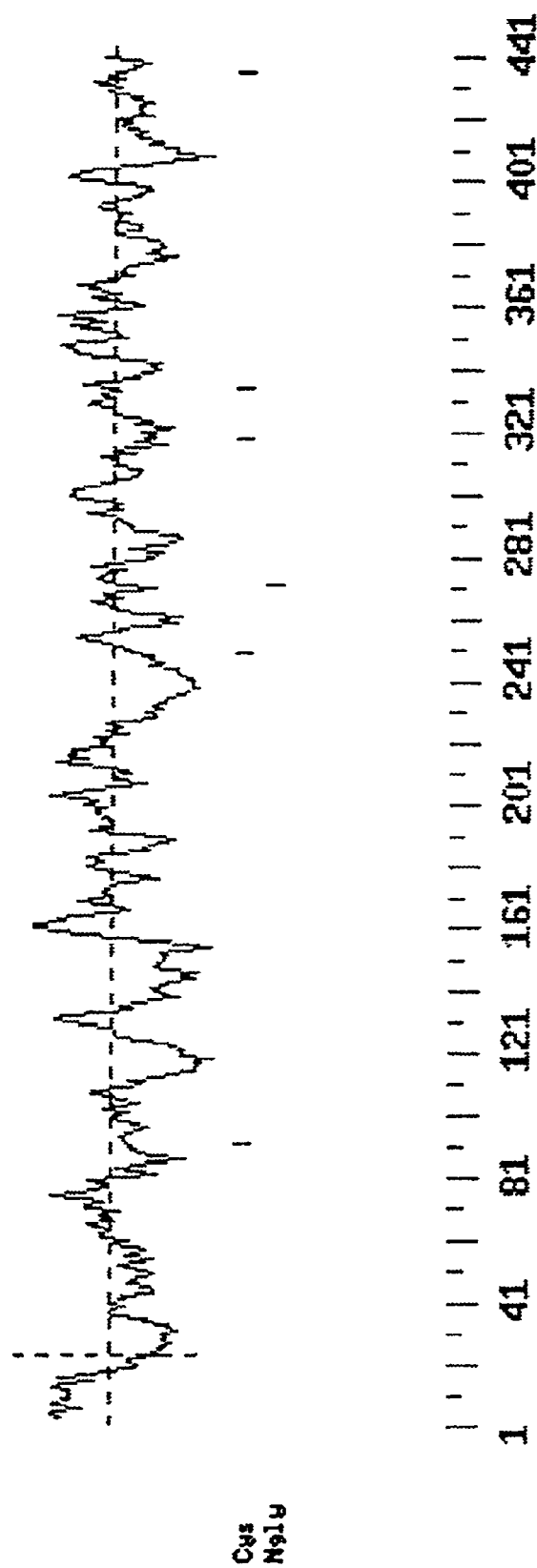
FIG. 4 is a hydropathy plot of short form human 46798. Relatively hydrophobic residues are shown above the dashed horizontal line, and relative hydrophilic residues are below the dashed horizontal line. The cysteine residues (cys) are indicated by short vertical lines below the hydropathy trace. The numbers corresponding to the amino acid sequence of human 46798 are indicated. Polypeptides of the invention include fragments which include: all or part of a hydrophobic sequence, i.e., a sequence above the dashed line, e.g., the sequence of about residues 155–175 of SEQ ID NO: 12; all or part of a hydrophilic sequence, i.e., a sequence below the dashed line, e.g., the sequence of residues 135–155 or 225–245 of SEQ ID NO: 12; a sequence which includes a cysteine residue; or a glycosylation site.

The invention relates to a novel matrix metalloproteinase protein that can exist in at least two forms, herein designated 'short' and 'long' forms. The matrix metalloproteinase (i.e., in either form) is referred to herein as "46798."

The long form human 46798 cDNA sequence (FIG. 1; SEQ ID NO: 1), which is approximately 2527 nucleotide residues long including non-translated regions, contains a predicted methionine-initiated coding sequence of about 1560 nucleotide residues, excluding termination codon (i.e., nucleotide residues 300–1860 of SEQ ID NO: 1; also shown in SEQ ID NO: 3). The coding sequence encodes a 520 amino acid protein having the amino acid sequence SEQ ID NO: 2.

The short form human 46798 cDNA sequence (FIG. 3; SEQ ID NO: 11), which is approximately 2310 nucleotide residues long including non-translated regions, contains a predicted methionine-initiated coding sequence of about 1335 nucleotide residues, excluding termination codon (i.e., nucleotide residues 317–1652 of SEQ ID NO: 11; also shown in SEQ ID NO: 13). The coding sequence encodes a 445 amino acid residue protein having the amino acid sequence SEQ ID NO: 12.

The long form human 46798 contains the following regions or other structural features: a predicted peptidase_M10 domain (PF00413) at about amino acid residues 39 to 225 of SEQ ID NO: 2, and four predicted hemopexin domains at about amino acid residues 328 to 371, 373 to 416, 418 to 464, and 466 to 510 of SEQ ID NO: 2. A transmembrane domain is predicted at about amino acid residues 1 to 22 of SEQ ID NO: 2. This transmembrane domain is predicted to form a signal sequence which is cleaved during or after synthesis of the protein, leading to its secretion. Mature long form 46798 protein is therefore predicted to be about 498 amino acid residues in length, it being recognized that cleavage of the signal sequence can occur within one or two residues of the predicted site (i.e., cleavage can occur following any of residues 20, 21, 22, 23, and 24 of SEQ ID NO: 2) and that immature long form 46798 protein can exist, at least temporarily, in a membrane-bound form prior to (or in the absence of) cleavage of the signal sequence.

The long form human 46798 protein has predicted N-glycosylation sites (Pfam accession number PS00001) at about amino acid residues 164–167 and 355–358 of SEQ ID NO: 2; five predicted protein kinase C phosphorylation sites (Pfam accession number PS00005) at about amino acid residues 56–58, 82–84, 136–138, 227–229, and 498–500 of SEQ ID NO: 2; six predicted casein kinase II phosphorylation sites (Pfam accession number PS00006) located at about amino acid residues 166–169, 272–275, 301–304, 326–329, 379–382, and 455–458 of SEQ ID NO: 2; seven predicted N-myristoylation sites (Pfam accession number PS00008) at about amino acid residues 92–97, 153–158, 193–198, 202–207, 288–293, 368–373, and 509–514 of SEQ ID NO: 2; a predicted amidation site (Pfam accession number PS00009) at about amino acid residues 312–315 of SEQ ID NO: 2; and a predicted neutral zinc metallopeptidase zinc-binding region signature sequence (Pfam accession number PS00142) at about amino acid residues 237–246 of SEQ ID NO: 2.

The short form human 46798 contains the following regions or other structural features: a predicted peptidase_M10 domain (PF00413) at about amino acid residues 39 to 150 of SEQ ID NO: 12, and four predicted hemopexin domains at about amino acid residues 253 to 296, 298 to 341, 343 to 389, and 391 to 435 of SEQ ID NO: 12. A transmembrane domain is predicted at about amino acid residues 1 to 22 of SEQ ID NO: 12. This transmembrane domain is predicted to form a signal sequence which is cleaved during or after synthesis of the protein, leading to its secretion. Mature short form 46798 protein is therefore predicted to be about 423 amino acid residues in length, it being recognized that cleavage of the signal sequence can occur within one or two residues of the predicted site (i.e., cleavage can occur following any of residues 20, 21, 22, 23, and 24 of SEQ ID NO: 12) and that immature short form 46798 protein can exist, at least temporarily, in a membrane-bound form prior to (or in the absence of) cleavage of the signal sequence.

The short form human 46798 protein has a predicted N-glycosylation site (Pfam accession number PS00001) at about amino acid residues 280–283 of SEQ ID NO: 12; four predicted protein kinase C phosphorylation sites (Pfam accession number PS00005) at about amino acid residues 56–58, 82–84, 152–154, and 423–425 of SEQ ID NO: 12; five predicted casein kinase II phosphorylation sites (Pfam accession number PS00006) located at about amino acid residues 197–200, 226–229, 251–254, 304–307, and 380–383 of SEQ ID NO: 12; five predicted N-myristoylation sites (Pfam accession number PS00008) at about amino acid residues 92–97, 127–132, 213–218, 293–298, and 434–439 of SEQ ID NO: 12; a predicted amidation site (Pfam accession number PS00009) at about amino acid residues 237–240 of SEQ ID NO: 12; and a predicted neutral zinc metallopeptidase zinc-binding region signature sequence (Pfam accession number PS00142) at about amino acid residues 162–171 of SEQ ID NO: 12.

For general information regarding PFAM identifiers, PS prefix and PF prefix domain identification numbers, refer to Sonnhammer et al. (1997, Protein 28:405–420).

Both the long and the short 46798 proteins contain a significant number of structural characteristics in common with members of the MMP family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., MMP proteins for any species described in the art (e.g., Nagase et al., supra, and references cited therein). Members of a family can also have common functional characteristics.

A 46798 polypeptide can include a peptidase_M10 domain. As used herein, the term "peptidase_M10 domain" refers to a protein domain having an amino acid sequence of about 50–200 amino acid residues in length, preferably, at least about 100–200 amino acids, more preferably about 150–190 amino acid residues, even more preferably about 190 amino acids or about 186 amino acids and has a bit score for the alignment of the sequence to the peptidase_M10 domain (HMM) of at least 50 or greater, preferably 60 or greater, more preferably, 75 or greater, and most preferably, 100 or greater. The peptidase_M10 domain has been assigned the PFAM accession PF00413.

In a preferred embodiment, 46798 polypeptide or protein has a peptidase_M10 domain or a region which includes at least about 50–200, more preferably about 100–200, 150–190, 190 or 186 amino acid residues and has at least about 60%, 70%, 80%, 90%, 95%, 99%, or 100% homology with a peptidase_M10 domain, e.g., the peptidase_M10 domain of human 46798 (e.g., residues 39–225 of SEQ ID NO: 2 or residues 39–150 of SEQ ID NO: 12).

To identify the presence of a peptidase_M10 domain profile in a 46798 receptor, the amino acid sequence of the protein is searched against a database of HMMs (e.g., the Pfam database, release 2.1) using the default parameters of the Washington University (St. Louis) Pfam World Wide Web site. For example, the hmmsf program, which is available as part of the HMMER package of search programs, is a family specific default program for PF00413 and score of 15 is the default threshold score for determining a hit. For example, using ORFAnalyzer software, a peptidase_M10 domain profile was identified in the amino acid sequence of SEQ ID NO: 2 (e.g., amino acids 39–225 of SEQ ID NO: 2 or amino acids 39–150 of SED ID NO: 12). Accordingly, a 46798 protein having at least about 60–70%, more preferably about 70–80%, or about 80–90% homology with the peptidase_M10 domain profile of human 46798 are within the scope of the invention.

In one embodiment, a 46798 protein exists in a mature form which does not include residues 1 to about 22 of either of SEQ ID NOs: 2 or 12. In this embodiment, the long form 46798 protein can have a length of about 498 (e.g., 496–500) amino acid residues, corresponding to a protein having an amino terminus at about residue 22 of SEQ ID NO: 2 (i.e., at residue 20–24) and having a carboxyl terminus at about residue 520 of SEQ ID NO: 2. In this embodiment the short form 46798 protein can have a length of about 423 (e.g., 421–425) amino acid residues, corresponding to a protein having an amino terminus at about residue 22 of SEQ ID NO: 12 (i.e., at residue 20–24) and having a carboxyl terminus at about residue 445 of SEQ ID NO: 12. In this embodiment, the protein is preferably not membrane-bound, and is also preferably extracellular.

In another embodiment, a 46798 protein includes at least one transmembrane domain. As used herein, the term "transmembrane domain" includes an amino acid sequence of about 5 amino acid residues in length that spans the plasma membrane. More preferably, a transmembrane domain includes about at least 10, 15, 20 or 22 amino acid residues and spans a membrane. Transmembrane domains are rich in hydrophobic residues, and typically have an alpha-helical structure. In a preferred embodiment, at least 50%, 60%, 70%, 80%, 90%, or 95% or more of the amino acids of a transmembrane domain are hydrophobic, e.g., leucines, isoleucines, tyrosines, or tryptophans. Transmembrane domains are described in, for example, htto:// pfam.wustl.edu/cgi-bin/getdesc?name=7tm-1, and Zagotta W. N. et al. (1996, Annu. Rev. Neurosci. 19: 235–263), the contents of which are incorporated herein by reference. Amino acid residues 1 to about 22 of either of SEQ ID NO: 2 or 12 comprise a transmembrane domain in a 46798 protein.

In one embodiment of the invention, a 46798 polypeptide includes at least one peptidase_M10 domain. In another embodiment, the 46798 polypeptide includes at least one peptidase_M10 domain and at least one transmembrane domain. In another embodiment, the 46798 polypeptide comprises at least one peptidase_M10 domain, at least one (and preferably two, three, or four) hemopexin domains.

The 46798 molecules of the present invention can further include one or more of the N-glycosylation, protein kinase C phosphorylation, casein kinase II phosphorylation, N-myristoylation, and amidation sites described herein, and preferably comprises most or all of them.

Because the 46798 polypeptides of the invention can modulate 46798-mediated activities, they can be used to develop novel diagnostic and therapeutic agents for 46798-mediated or related disorders, as described below.

As used herein, a "46798 activity," "biological activity of 46798," or "functional activity of 46798," refers to an activity exerted by a 46798 protein, polypeptide or nucleic acid molecule on, for example, a 46798-responsive cell or on a 46798 substrate (e.g., a protein or extracellular matrix substrate) as determined in vivo or in vitro. In one embodiment, a 46798 activity is a direct activity, such as association with a 46798 target molecule. A "target molecule" or "binding partner" of a 46798 protein is a molecule with which the 46798 protein binds or interacts in nature. In an exemplary embodiment, such a target molecule is a 46798 receptor. A 46798 activity can also be an indirect activity, such as a cellular signaling activity mediated by interaction of the 46798 protein with a 46798 receptor.

The 46798 molecules of the present invention are predicted to have similar biological activities as MMP family members. For example, the 46798 proteins of the present invention can have one or more of the following activities:

(1) catalyzing cleavage of covalent bonds within or between amino acid residues in ECM, cell-surface, and extracellular proteins;

(2) modulating degradation of ECM;

(3) modulating angiogenesis;

(4) modulating neurite growth;

(5) modulating tumor cell invasion or metastasis;

(6) modulating tissue or organ integrity;

(7) modulating wound healing;

(8) modulating endometrial cycling;

(9) modulating hair follicle cycling;

(10) modulating bone remodeling;

(11) modulating ovulation;

(12) modulating embryonic development;

(13) modulating apoptosis;

(14) modulating growth, repair, or replacement of an epithelial tissue; and

(15) modulating growth, repair, or replacement of a neuronal tissue.

Thus, 46798 molecules described herein can act as novel diagnostic targets and therapeutic agents for prognosticating, diagnosing, preventing, inhibiting, alleviating, or curing MMP-related disorders.

The data disclosed herein confirm expression of the 46798 gene in skin, colon, artery, vein, human umbilical vein epithelial cells (HUVEC), nerve, and brain cells, indicating that 46798 protein can function in normal tissues to facilitate growth, repair, replacement, or renewal of endothelial, epithelial, and neuronal tissues, presumably by remodeling or degrading extracellular matrix through or into which new endothelial, epithelial, or neuronal cells must move, grow, or proliferate.

Enhancement of the activity of 46798 protein or expression of the 46798 gene can enhance the regenerative capacity of endothelial and epithelial tissues, and such enhancement can alleviate, inhibit, prevent, or reverse the effects of disorders that are characterized by damage to endothelial, epithelial, and neuronal tissues. By way of example, patients afflicted with atherosclerosis exhibit blood vessel lesions which are characterized by altered endothelial cell layers, upon, within, or under which a variety of materials can accumulate. Enhancing activity or expression of 46798 can promote the rate at which, and the degree to which, damaged vascular endothelium is repaired or replaced, thereby alleviating atherosclerosis in the patient. Similarly, a variety of bacterial and viral infections can afflict endothelial and epithelial cell layers, leading to death of endothelial and epithelial cells. Enhancing 46798 activity or expression can increase the rate at which endothelial and epithelial cells proliferate and the rate at which damage to the endothelial or epithelial cell layer is repaired. Enhancing 46798 activity or expression can also enhance the rate and extent of wound healing, and can reduce scarring by enhancing growth of tissue that subtantially duplicates the original tissue. Similarly, enhancement of activity or expression of 46798 can be used to promote growth, repair, and replacement of substantially any epithelial or endothelial tissue in the body, regardless of whether the damage that necessitates the repair or replacement is normally occurring (e.g., repair of ovarian epithelium following ovulation) or associated with a chronic injury (e.g., a skin burn or broken bone) or an acute disorder (e.g., an autoimmune disorder of the skin). Screening of compounds for the ability to enhance 46798 expression or activity can identify agents useful for enhancing growth, repair, and replacement of epithelial and endothelial tissues.

Enhancement of the activity of 46798 protein or expression of the 46798 gene can enhance neuron growth (including extension), re-growth, and interconnection. Such enhancement can promote neuronal growth or attachment by degrading ECM that would otherwise obstruct the growth or attachment. Such enhancement can also inactivate moieties (e.g., chondroitin sulfates) in ECM that inhibit neuronal growth and uncover moities (e.g., laminin) in ECM that enhance neuronal growth. These characteristics indicate that 46798 molecules disclosed herein can be used to alleviate, inhibit, prevent, or reverse disorders associated with insufficient growth and connection of nerve cells. Examples of such disorders include failure of the innervation of a wounded tissue to be restored during wound repair. Certain neuronal tissues (e.g., brain and spinal cord) are characterized by a substantial inability to re-establish functional neuronal conditions following traumatic, ischemic, or other injury. 46798 molecules described herein can be used to enhance healing of damaged neuronal tissues. Screening of compounds for the ability to enhance 46798 expression or activity can identify agents useful for enhancing neuronal growth, interconnections, and healing.

Inhibiting activity of 46798 protein or expression of the 46798 gene can alleviate, reverse, inhibit, or prevent disorders characterized by hyperproliferation of endothelial or epithelial tissues. Examples of these disorders include tumors of endothelial or epithelial origin, dermal fibroses, and psoriasis. Inhibition of 46798 activity or expression can also reduce neuronal growth or interconnection, and can be used, for example, to inhibit re-growth or re-connection of surgically severed nerves (e.g., vagus nerve severed in order to reduce gastric acid secretion). Screening of compounds for the ability to inhibit 46798 expression or activity can identify agents useful for inhibiting, reducing, or preventing growth, proliferation, and repair of endothelial, epithelial, and neuronal tissues.

As indicated in FIG. 5, long form human 46798 protein exhibits high sequence homology with a protein designated MMP-28 (Lohi et al., 2001, J. Biol. Chem. 276:10134–10144; Marchenko et al., 2001, Gene 265:87–93) and with a protein designated PPIM23 in the PCT application having publication number WO 01/10903. MMP-28 has been tentatively mapped to human chromosomal location 17q11.2. Previously recognized genetic aberrations associated with diseases (e.g., leukemia, colon adenocarcinoma, various myeloproliferative disorders, neurofibrosarcomas {malignant schwannoma}, skin cancer, chondrosarcoma, and follicular lymphoma) have been mapped to this region (Cancer Genome Anatomy Database). However, no gene had previously been identified as being involved in these cancers. The data presented herein indicate that aberrations in the 46798 gene can cause, or at least contribute to, one or more of these diseases, particularly those arising in epithelial and neuronal tissues (e.g., colon adenocarcinoma, skin cancer, malignant schwannoma, and follicular lymphoma).

More broadly, relatively high levels of expression of 46798 protein detected in cancer cells from tumors such as cervical squamous cell carcinomas and colon tumors indicates that 46798 protein is a matrix metalloproteinase which is used by tumor cells to degrade and remodel extracellular matrix in which tumor cells occur. These data indicate that 46798 protein is involved in growth, migration, and metastasis of tumor cells, at least in cervical and colon tumors. 46798 also can facilitate growth, spread, and metastasis of other tumors, particularly those of epithelial, endothelial, or neuronal origin. Taken together, the data presented herein indicate that the 46798 gene and its encoded protein have a significant role in growth and metastasis of tumors. Inhibition of the activity of 46798 protein or expression of the 46798 gene can inhibit or prevent growth, spread, and metastasis of tumors in humans.

Data disclosed herein confirm expression of 46798 protein in lung cells obtained from a patient afflicted with chronic obstructive pulmonary disorder (COPD), indicating an association with that disorder as well. Involvement of 46798 in COPD is an example of how the effects of 46798 protein on extracellular matrix in a tissue can have indirect deleterious effects (e.g., altering the permeability of lung epithelium in a COPD patient) on an organ when 46798 activity or expression occurs at an aberrant level.

Other activities, as described below, include the ability to modulate function, survival, morphology, proliferation and/or differentiation of cells of tissues in which 46798 molecules are expressed. Thus, the 46798 molecules can act as novel diagnostic targets and therapeutic agents for controlling disorders involving aberrant activities of these cells.

The 46798 molecules can also act as novel diagnostic targets and therapeutic agents for controlling cellular proliferative and/or differentiative disorders (e.g., hematopoietic neoplastic disorders, carcinoma, sarcoma, metastatic disorders or hematopoietic neoplastic disorders such as leukemias). A metastatic tumor can arise from a multitude of primary tumor types, including but not limited to those of prostate, colon, lung, breast and liver origin. In particular, 46798 molecules can be used to diagnose, prognosticate, inhibit, or alleviate disorders arising from aberrant epithelial, endothelial, and neuronal tissues.

As used herein, the terms "cancer," "hyperproliferative" and "neoplastic" refer to cells having the capacity for autonomous growth, i.e., an abnormal state or condition characterized by rapidly proliferating cell growth. Hyperproliferative and neoplastic disease states can be categorized as pathologic, i.e., characterizing or constituting a disease state, or can be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. The disorders can arise from poorly differentiated acute leukemias, e.g., erythroblastic leukemia and acute megakaryoblastic leukemia. Exemplary myeloid disorders include, but are not limited to, acute promyeloid leukemia (APML), acute myelogenous leukemia (AML) and chronic myelogenous leukemia (CML; reviewed in Vaickus, 1991, Crit. Rev. Oncol./Hemotol. 11:267–297); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

The 46798 protein, fragments thereof, and derivatives and other variants of the sequence in one of SEQ ID NOs: 2 and 12 thereof are collectively referred to as "polypeptides or proteins of the invention" or "46798 polypeptides or proteins". Nucleic acid molecules encoding such polypeptides or proteins are collectively referred to as "nucleic acids of the invention" or "46798 nucleic acids." 46798 molecules refer to 46798 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules that are separated from other nucleic acid molecules that are present in the natural source of the nucleic acid. For example, with regards to genomic DNA, the term "isolated" includes nucleic acid molecules that are separated from the chromosome with which the genomic DNA is naturally associated. Preferably, an "isolated" nucleic acid is free of sequences that naturally flank the nucleic acid (i.e., sequences located at the 5'- and/or 3'-ends of the nucleic acid) in the genomic DNA of the organism from which the nucleic acid is derived. For example, in various embodiments, the isolated nucleic acid molecule can contain less than about 5 kilobases, 4 kilobases, 3 kilobases, 2 kilobases, 1 kilobase, 0.5 kilobase or 0.1 kilobase of 5'- and/or 3'-nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent conditions are known to those skilled in the art and can be found in available references (e.g., Current Protocols in Molecular Biology, John Wiley & Sons, N.Y., 1989, 6.3.1–6.3.6). Aqueous and non-aqueous methods are described in that reference and either can be used. A preferred example of stringent hybridization conditions are hybridization in 6× sodium chloride/sodium citrate (SSC) at about 45° C., followed by one or more washes in 0.2× SSC, 0.1% (w/v) SDS at 50° C. Another example of stringent hybridization conditions are hybridization in 6× sodium chloride/sodium citrate (SSC) at about 45° C., followed by one or more washes in 0.2× SSC, 0.1% (w/v) SDS at 55° C. A further example of stringent hybridization conditions are hybridization in 6× sodium chloride/sodium citrate (SSC) at about 45° C., followed by one or more washes in 0.2× SSC, 0.1% (w/v) SDS at 60° C. Preferably, stringent hybridization conditions are hybridization in 6× sodium chloride/sodium citrate (SSC) at about 45° C., followed by one or more washes in 0.2× SSC, 0.1% (w/v) SDS at 65° C. Particularly preferred stringency conditions (and the conditions that should be used if the practitioner is uncertain about what conditions should be applied to determine if a molecule is within a hybridization limitation of the invention) are 0.5 molar sodium phosphate, 7% (w/v) SDS at 65° C., followed by one or more washes at 0.2× SSC, 1% (w/v) SDS at 65° C. Preferably, an isolated nucleic acid molecule of the invention that hybridizes under stringent conditions to the sequence of any of SEQ ID NOs: 1, 3, 11, and 13, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 46798 protein, preferably a mammalian 46798 protein, and can further include non-coding regulatory sequences and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 46798 protein having less than about 30%, 20%, 10% and more preferably 5% (by dry weight), of non-46798 protein (also referred to herein as a "contaminating protein"), or of chemical precursors or non-46798 chemicals. When the 46798 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 46798 (e.g., the sequence of any one of SEQ ID NOs: 1, 3, 11, and 13)

without abolishing or, more preferably, without substantially altering a biological activity, whereas an "essential" amino acid residue results in such a change. For example, amino acid residues that are conserved among the polypeptides of the present invention, e.g., those present in the peptidase M10 domain are predicted to be particularly non-amenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 46798 protein is preferably replaced with another amino acid residue from the same side chain family. Alternatively, in another embodiment, mutations can be introduced randomly along all or part of a 46798 coding sequence, such as by saturation mutagenesis, and the resultant mutants can be screened for 46798 biological activity to identify mutants that retain activity. Following mutagenesis of any one of SEQ ID NOs: 1, 3, 11, and 13, the encoded protein can be expressed recombinantly and the activity of the protein can be determined.

As used herein, a "biologically active portion" of a 46798 protein includes a fragment of a 46798 protein that participates in an interaction between a 46798 molecule and a non-46798 molecule. Biologically active portions of a 46798 protein include peptides comprising amino acid sequences sufficiently homologous to or derived from the amino acid sequence of the 46798 protein, e.g., the amino acid sequence shown in SEQ ID NO: 2 or SEQ ID NO: 12, which include less amino acids than the full length 46798 proteins, and exhibit at least one activity of a 46798 protein. Typically, biologically active portions comprise a domain or motif with at least one activity of the 46798 protein, e.g., a domain or motif capable of catalyzing an activity described herein, such as cleavage of a covalent bond between amino acid residues of an ECM protein.

A biologically active portion of a 46798 protein can be a polypeptide that for example, 10, 25, 50, 100, 200, 300, or 400 or more amino acids in length. Biologically active portions of a 46798 protein can be used as targets for developing agents that modulate a 46798-mediated activity, e.g., a biological activity described herein.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 46798 amino acid sequence of SEQ ID NO: 2 having 316 amino acid residues, at least 124, preferably at least 165, more preferably at least 207, even more preferably at least 248, and even more preferably at least 289, 330, 400, 420, 445, 498, or 520 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970, J. Mol. Biol. 48:444–453) algorithm which has been incorporated into the GAP program in the GCG software package (available commercially), using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available commercially), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

The percent identity between two amino acid or nucleotide sequences can be determined using the algorithm of Meyers et al. (1989, CABIOS, 4:11–17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990, J. Mol. Biol. 215:403–410). BLAST nucleotide searches can be performed with the NBLAST program, score=100, wordlength=12 to obtain nucleotide sequences homologous to 46798 nucleic acid molecules of the invention. BLAST protein searches can be performed with the XBLAST program, score=50, wordlength=3 to obtain amino acid sequences homologous to 46798 protein molecules of the invention. To obtain gapped alignments for comparison purposes, gapped BLAST can be utilized as described in Altschul et al. (1997, Nucl. Acids Res. 25:3389–3402). When using BLAST and gapped BLAST programs, the default parameters of the respective programs (e.g., XBLAST and NBLAST) can be used. By way of example, the BLAST server available on line at the National Center for Biotechnology Information (National Library of Medicine, National Institutes of Health) can be used.

"Malexpression or aberrant expression," as used herein, refers to a non-wild-type pattern of gene expression, at the RNA or protein level. It includes: expression at non-wild-type levels, i.e., over- or under-expression; a pattern of expression that differs from wild-type in terms of the time or stage at which the gene is expressed, e.g., increased or decreased expression (as compared with wild-type) at a predetermined developmental period or stage; a pattern of expression that differs from wild-type in terms of decreased expression (as compared with wild-type) in a predetermined cell type or tissue type; a pattern of expression that differs from wild-type in terms of the splicing size, amino acid sequence, post-transitional modification, or biological activity of the expressed polypeptide; a pattern of expression that differs from wild-type in terms of the effect of an environmental stimulus or extracellular stimulus on expression of the gene, e.g., a pattern of increased or decreased expression (as compared with wild-type) in the presence of an increase or decrease in the strength of the stimulus.

"Subject," as used herein, can refer to a mammal, e.g., a human, or to an experimental or animal or disease model. The subject can also be a non-human animal, e.g., a horse, cow, goat, or other domestic animal.

A "purified preparation of cells," as used herein, refers to, in the case of plant or animal cells, an in vitro preparation of cells and not an entire intact plant or animal. In the case of cultured cells or microbial cells, it consists of a preparation of at least 10%, and more preferably, 50% of the subject cells.

Various aspects of the invention are described in further detail below.

Isolated Nucleic Acid Molecules

In one aspect, the invention provides, an isolated or purified, nucleic acid molecule that encodes a 46798 polypeptide described herein, e.g., a full-length 46798 protein or a fragment thereof, e.g., a biologically active portion of 46798 protein. Also included is a nucleic acid fragment suitable for use as a hybridization probe, which can be used, e.g., to a identify nucleic acid molecule encoding a polypeptide of the invention, 46798 mRNA, and fragments suitable for use as primers, e.g., PCR primers for the amplification or mutation of nucleic acid molecules.

In one embodiment, an isolated nucleic acid molecule of the invention includes the nucleotide sequence shown in one of SEQ ID NOs: 1 and 11, or a portion of either of these nucleotide sequences. In one embodiment, the nucleic acid molecule includes sequences encoding the human 46798 protein (i.e., "the coding region," from nucleotides 300–1859 of SEQ ID NO: 1 or from nucleotides 317–1652 of SEQ ID NO: 11), as well as 5'-non-translated sequences (i.e, nucleotides 1–299 of SEQ ID NO: 1 or nucleotides 1–316 of SEQ ID NO: 11) or 3'-non-translated sequences (i.e., nucleotides 1860–2527 of SEQ ID NO: 1 or nucleotides 1563–2310 of SEQ ID NO: 11). Alternatively, the nucleic acid molecule can include only the coding region of one of SEQ ID NOs: 1 and 11 (e.g., nucleotides 300–1859, corresponding to SEQ ID NO: 3 or nucleotides 317–1652 corresponding to SEQ ID NO: 13) and, e.g., no flanking sequences which normally accompany the subject sequence. In another embodiment, the nucleic acid molecule encodes a sequence corresponding to the 520 amino acid residue immature protein of SEQ ID NO: 2, the 498 amino acid residue mature protein of SEQ ID NO: 2, the 445 amino acid residue immature protein of SEQ ID NO: 12, or the 423 amino acid residue mature protein of SEQ ID NO: 12.

In another embodiment, an isolated nucleic acid molecule of the invention includes a nucleic acid molecule which is a complement of the nucleotide sequence shown in one of SEQ ID NOs: 1, 3, 11, and 13, and a portion of any of these sequences. In other embodiments, the nucleic acid molecule of the invention is sufficiently complementary to the nucleotide sequence shown in one of SEQ ID NOs: 1, 3, 11, and 13 that it can hybridize with a nucleic acid having that sequence, thereby forming a stable duplex.

In one embodiment, an isolated nucleic acid molecule of the invention includes a nucleotide sequence which is at least about 60%, 65%, 70%, 75%, 80%, 85%, 90%, 91%, 92%, 93%, 94%, 95%, 96%, 97%, 98%, or 99% or more homologous to the entire length of the nucleotide sequence shown in one of SEQ ID NOs: 1, 3, 11, and 13, and a portion, preferably of the same length, of any of these nucleotide sequences. In another embodiment, the isolated nucleic acid molecule is completely homologous with, or completely complementary to, at least 500, 1000, 1224, 1250, 1500, 1588, 1750, 2000, or 2500 consecutive nucleotide residues of one of SEQ ID NOs: 1, 3, 11, and 13.

In one embodiment, the isolated nucleic acid does not include residues 680–904 of SEQ ID NO: 1 (i.e., it encodes the short form of 46798).

46798 Nucleic Acid Fragments

A nucleic acid molecule of the invention can include only a portion of the nucleic acid sequence of one of SEQ ID NOs: 1, 3, 11, and 13. For example, such a nucleic acid molecule can include a fragment that can be used as a probe or primer or a fragment encoding a portion of a 46798 protein, e.g., an immunogenic or biologically active portion of a 46798 protein. A fragment can comprise nucleotides corresponding to residues 39–225 of SEQ ID NO: 2 or residues 39–150 of SEQ ID NO: 12, which encodes a peptidase_M10 domain of human 46798. The nucleotide sequence determined from the cloning of the 46798 gene facilitates generation of probes and primers for use in identifying and/or cloning other 46798 family members, or fragments thereof, as well as 46798 homologues, or fragments thereof, from other species.

In another embodiment, a nucleic acid includes a nucleotide sequence that includes part, or all, of the coding region and extends into either (or both) the 5'- or 3'-non-coding region. Other embodiments include a fragment that includes a nucleotide sequence encoding an amino acid fragment described herein. Nucleic acid fragments can encode a specific domain or site described herein or fragments thereof, particularly fragments thereof that are at least about 250 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein.

46798 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of one of SEQ ID NOs: 1, 3, 11, and 13, and a naturally occurring allelic variant or mutant of one of SEQ ID NOs: 1, 3, 11, and 13.

In a preferred embodiment the nucleic acid is a probe which is at least 5 or 10, and less than 200, more preferably less than 100, or less than 50, base pairs in length. It should be identical, or differ by 1, or fewer than 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid that encodes: a peptidase_M10 domain at about amino acid residues 39 to 225 of SEQ ID NO: 2 or at about amino acid residues 39–150 of SEQ ID NO: 12; a hemopexin domain at about amino acid residues 328 to 371, 373 to 416, 418 to 464, or 466 to 510 of SEQ ID NO: 2 or at about amino acid residues 253 to 296, 298 to 341, 343 to 389, or 391 to 435 of SEQ ID NO: 12; the transmembrane domain at about amino acid residues 1 to 22 of one of SEQ ID NOs: 2 and 12.

In another embodiment a set of primers is provided, e.g., primers suitable for use in a PCR, which can be used to amplify a selected region of a 46798 sequence. The primers should be at least 5, 10, or 50 base pairs in length and less than 100, or less than 200, base pairs in length. The primers should be identical, or differs by one base from a sequence disclosed herein or from a naturally occurring variant. Primers suitable for amplifying all or a portion of any of the following regions are provided: e.g., one or more a peptidase_M10 domain, a hemopexin domain, and a transmembrane domain, all as defined above relative to one of SEQ ID NOs: 2 and 12.

A nucleic acid fragment can encode an epitope bearing region of a polypeptide described herein.

A nucleic acid fragment encoding a "biologically active portion of a 46798 polypeptide" can be prepared by isolating a portion of the nucleotide sequence of one of SEQ ID NOs: 1, 3, 11, and 13 which encodes a polypeptide having a 46798 biological activity (e.g., the biological activities of the 46798 proteins are described herein), expressing the encoded portion of the 46798 protein (e.g., by recombinant expression in vitro) and assessing the activity of the encoded portion of the 46798 protein. For example, a nucleic acid fragment encoding a biologically active portion of 46798 includes a peptidase_M10 domain, e.g., amino acid residues 39 to 225 of SEQ ID NO: 2 or amino acid residues 39 to 150 of SEQ ID NO: 12. A nucleic acid fragment encoding a biologically active portion of a 46798 polypeptide can comprise a nucleotide sequence that is greater than 25 or more nucleotides in length.

In one embodiment, a nucleic acid includes one that has a nucleotide sequence which is greater than 260, 300, 400, 500, 600, 700, 800, 900, 1000, 1100, 1200, 1300, 1400, 1500, 2000, or 2500 or more nucleotides in length and that hybridizes under stringent hybridization conditions with a nucleic acid molecule having the sequence of one of SEQ ID NOs: 1, 3, 11, and 13.

46798 Nucleic Acid Variants

The invention further encompasses nucleic acid molecules having a sequence that differs from the nucleotide sequence shown in one of SEQ ID NOs: 1, 3, 11, and 13. Such differences can be attributable to degeneracy of the genetic code (i.e., differences which result in a nucleic acid that encodes the same 46798 proteins as those encoded by the nucleotide sequence disclosed herein). In another embodiment, an isolated nucleic acid molecule of the invention encodes a protein having an amino acid sequence which differs by at least 1, but by fewer than 5, 10, 20, 50, or 100, amino acid residues from one of SEQ ID NOs: 2 and 12. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. For example, the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid has a sequence that differs from that of one of SEQ ID NO: 1, 3, 11, and 13, e.g., as follows: by at least one, but by fewer than 10, 20, 30, or 40, nucleotide residues; or by at least one but by fewer than 1%, 5%, 10% or 20% of the nucleotide residues in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the nucleotide sequence shown in one of SEQ ID NOs: 1, 3, 11, and 13, or a fragment of one of these sequences. Such nucleic acid molecules can readily be identified as being able to hybridize under stringent conditions, to the nucleotide sequence shown in one of SEQ ID NOs: 1, 3, 11, and 13, or a fragment of one of these sequences. Nucleic acid molecules corresponding to orthologs, homologs, and allelic variants of the 46798 cDNAs of the invention can further be isolated by mapping to the same chromosome or locus as the 46798 gene.

Preferred variants include those that are correlated with any of the 46798 biological activities described herein, e.g., catalyzing cleavage of a covalent bond between amino acid residues of an ECM protein.

Allelic variants of 46798 (e.g., human 46798) include both functional and non-functional proteins. Functional allelic variants are naturally occurring amino acid sequence variants of the 46798 protein within a population that maintain the ability to mediate any of the 46798 biological activities described herein.

Functional allelic variants will typically contain only conservative substitution of one or more amino acids of one of SEQ ID NOs: 2 and 12, or substitution, deletion or insertion of non-critical residues in non-critical regions of the protein. Non-functional allelic variants are naturally-occurring amino acid sequence variants of the 46798 (e.g., human 46798) protein within a population that do not have the ability to mediate any of the 46798 biological activities described herein. Non-functional allelic variants will typically contain a non-conservative substitution, a deletion, or insertion, or premature truncation of the amino acid sequence of one of SEQ ID NOs: 2 and 12, or a substitution, insertion, or deletion in critical residues or critical regions of the protein.

Moreover, nucleic acid molecules encoding other 46798 family members and, thus, which have a nucleotide sequence which differs from the 46798 sequences of one of SEQ ID NO: 1, 3, 11, and 13 are within the scope of the invention.

Antisense Nucleic Acid Molecules, Ribozymes and Modified 46798 Nucleic Acid Molecules In another aspect, the invention features, an isolated nucleic acid molecule that is antisense to 46798. An "antisense" nucleic acid can include a nucleotide sequence that is complementary to a "sense" nucleic acid encoding a protein, e.g., complementary to the coding strand of a double-stranded cDNA molecule or complementary to an mRNA sequence. The antisense nucleic acid can be complementary to an entire 46798 coding strand, or to only a portion thereof (e.g., the coding region of human 46798 corresponding to one of SEQ ID NOs: 3 and 13). In another embodiment, the antisense nucleic acid molecule is antisense to a "non-coding region" of the coding strand of a nucleotide sequence encoding 46798 (e.g., the 5'- and 3'-non-translated regions).

An antisense nucleic acid can be designed such that it is complementary to the entire coding region of 46798 mRNA, but more preferably is an oligonucleotide that is antisense to only a portion of the coding or non-coding region of 46798 mRNA. For example, the antisense oligonucleotide can be complementary to the region surrounding the translation start site of 46798 mRNA, e.g., between the –10 and +10 regions of the target gene nucleotide sequence of interest. An antisense oligonucleotide can be, for example, about 7, 10, 15, 20, 25, 30, 35, 40, 45, 50, 55, 60, 65, 70, 75, or 80 or more nucleotide residues in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 46798 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an alpha-anomeric nucleic acid molecule. An alpha-anomeric nucleic acid molecule forms specific double-stranded hybrids with complementary RNA in which, contrary to the usual beta-units, the strands run parallel to each other (Gaultier et al., 1987, Nucl. Acids. Res. 15:6625–6641). The antisense nucleic acid molecule can also comprise a 2'-o-methylribonucleotide (Inoue et al., 1987, Nucl. Acids Res. 15:6131–6148) or a chimeric RNA-DNA analogue (Inoue et al., 1987, FEBS Lett. 215:327–330).

In still another embodiment, an antisense nucleic acid of the invention is a ribozyme. A ribozyme having specificity for a 46798-encoding nucleic acid can include one or more sequences complementary to the nucleotide sequence of a 46798 cDNA disclosed herein (i.e., one of SEQ ID NOs: 1, 11, 3, or 13), and a sequence having known catalytic sequence responsible for mRNA cleavage (see, for example, U.S. Pat. No. 5,093,246 or Haselhoff et al. (1988, Nature 334:585–591). For example, a derivative of a Tetrahymena L-19 IVS RNA can be constructed in which the nucleotide sequence of the active site is complementary to the nucleotide sequence to be cleaved in a 46798-encoding mRNA (e.g., U.S. Pat. No. 4,987,071; and U.S. Pat. No. 5,116,742). Alternatively, 46798 mRNA can be used to select a catalytic RNA having a specific ribonuclease activity from a pool of RNA molecules (e.g., Bartel et al., 1993, Science 261:1411–1418).

46798 gene expression can be inhibited by targeting nucleotide sequences complementary to the regulatory region of the 46798 (e.g., the 46798 promoter and/or enhancers) to form triple helical structures that prevent transcription of the 46798 gene in target cells (Helene, 1991, Anticancer Drug Des. 6:569–584; Helene, et al., 1992, Ann. N.Y. Acad. Sci. 660:27–36; Maher, 1992, Bioassays 14:807–815). The potential sequences that can be targeted for triple helix formation can be increased by creating a so-called "switchback" nucleic acid molecule. Switchback molecules are synthesized in an alternating 5' to 3', 3' to 5' manner, such that they hybridize with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 46798 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (Hyrup et al., 1996, Bioorg. Med. Chem. 4:5–23). As used herein, the terms "peptide nucleic acid" (PNA) refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup et al. (1996, supra; Perry-O'Keefe et al., Proc. Natl. Acad. Sci. USA 93:14670–14675).

PNAs of 46798 nucleic acid molecules can be used in therapeutic and diagnostic applications. For example, PNAs can be used as antisense or anti-gene agents for sequence-specific modulation of gene expression by, for example, inducing transcription or translation arrest or inhibiting replication. PNAs of 46798 nucleic acid molecules can also be used in the analysis of single base pair mutations in a gene, (e.g., by PNA-directed PCR clamping); as 'artificial restriction enzymes' when used in combination with other enzymes, (e.g., S1 nucleases, as described in Hyrup et al., 1996, supra); or as probes or primers for DNA sequencing or hybridization (Hyrup et al., 1996, supra; Perry-O'Keefe, supra).

In other embodiments, the oligonucleotide can include other appended groups such as peptides (e.g., for targeting host cell receptors in vivo), or agents facilitating transport across the cell membrane (e.g., Letsinger et al., 1989, Proc. Natl. Acad. Sci. USA 86:6553–6556; Lemaitre et al., 1987, Proc. Natl. Acad. Sci. USA 84:648–652; PCT publication number WO 88/09810) or the blood-brain barrier (see, e.g., PCT publication number WO 89/10134). In addition, oligonucleotides can be modified with hybridization-triggered cleavage agents (e.g., Krol et al., 1988, Bio-Techniques 6:958–976) or intercalating agents (e.g., Zon, 1988, Pharm. Res. 5:539–549). To this end, the oligonucleotide can be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 46798 nucleic acid of the invention, two complementary regions, one having a fluorophore and the other having a quencher, such that the molecular beacon is useful for quantitating the presence of the 46798 nucleic acid of the invention in a sample. Molecular beacon nucleic acids are described, for example, in U.S. Pat. Nos. 5,854,033, 5,866,336, and 5,876,930.

Isolated 46798 Polypeptides

In another aspect, the invention features, an isolated 46798 protein, or fragment, e.g., a biologically active portion, for use as immunogens or antigens to raise or test (or more generally to bind) anti-46798 antibodies. 46798 protein can be isolated from cells or tissue sources using standard protein purification techniques. 46798 protein or fragments thereof can be produced by recombinant DNA techniques or synthesized chemically.

Polypeptides of the invention include those that arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when the polypeptide is expressed in a native cell, or in systems which result in the alteration or omission of post-translational modifications, e.g., glycosylation or cleavage, present when expressed in a native cell.

In one embodiment, the 46798 polypeptide does not include residues 128 to 202 of SEQ ID NO: 2 (i.e., it is derived from the short form of 46798).

In a preferred embodiment, a 46798 polypeptide has one or more of the following characteristics:

(1) it catalyzes cleavage of covalent bonds within or between amino acid residues in ECM, cell-surface, and extracellular proteins;

(2) it modulates degradation of ECM;

(3) it modulates angiogenesis;

(4) it modulates neurite growth;

(5) it modulates tumor cell invasion or metastasis;

(6) it modulates tissue or organ integrity;

(7) it modulates wound healing;

(8) it modulates endometrial cycling;

(9) it modulates hair follicle cycling;

(10) it modulates bone remodeling;

(11) it modulates ovulation;

(12) it modulates embryonic development;

(13) it modulates apoptosis;

(14) it modulates growth, repair, or replacement of an epithelial tissue;

(15) it modulates growth, repair, or replacement of a neuronal tissue;

(16) it has a molecular weight, amino acid composition or other physical characteristic of a 46798 protein of one of SEQ ID NOs: 2 and 12;

(17) it has an overall sequence similarity (identity) of at least 60–65%, preferably at least 70%, more preferably at least 75, 80, 85, 86, 87, 88, 89, 90, 91, 92, 93, 94, 95, 96, 97, 98, or 99% or more, with a portion of one of SEQ ID NOs: 2 and 12;

(18) it has an N-terminal transmembrane domain which is preferably about 70%, 80%, 90%, 95%, 96%, 97%, 98%, or 99% or more, identical with amino acid residues 1–22 of one of SEQ ID NOs: 2 and 12;

(19) it has at least one non-transmembrane domain which is preferably about 70%, 80%, 90%, 95%, 96%, 97%, 98%, or 99% or more, identical with amino acid residues 23–520 of one of SEQ ID NOs: 2 and 12; or

(20) it has a peptidase_M10 domain which is preferably about 70%, 80%, 90%, 95%, 96%, 97%, 98%, 99% or higher, identical with amino acid residues 39–225 of one of SEQ ID NOs: 2 and 12.

In a preferred embodiment, the 46798 protein or fragment thereof differs only insubstantially, if at all, from the corresponding sequence in one of SEQ ID NOs: 2 and 12. In one embodiment, it differs by at least one, but by fewer than 15, 10 or 5 amino acid residues. In another, it differs from the corresponding sequence in one of SEQ ID NOs: 2 and 12 by at least one residue but fewer than 20%, 15%, 10% or 5% of the residues differ from the corresponding sequence in one of SEQ ID NOs: 2 and 12 (if this comparison requires alignment the sequences should be aligned for maximum homology. "Looped" out sequences from deletions or insertions, or mismatches, are considered differences). The differences are, preferably, differences or changes at a non-essential amino acid residues or involve a conservative substitution of one residue for another. In a preferred embodiment the differences are not in residues 39 to 225 of SEQ ID NO: 2 or in residues 39 to 150 of SEQ ID NO: 12.

Other embodiments include a protein that has one or more changes in amino acid sequence, relative to one of SEQ ID NOs: 2 and 12 (e.g., a change in an amino acid residue which is not essential for activity). Such 46798 proteins differ in amino acid sequence from one of SEQ ID NOs: 2 and 12, yet retain biological activity.

In one embodiment, the protein includes an amino acid sequence at least about 60%, 65%, 70%, 75%, 80%, 85%, 90%, 95%, 98% or more homologous to one of SEQ ID NOs: 2 and 12.

A 46798 protein or fragment is provided which has an amino acid sequence which varies from one of SEQ ID NOs: 2 and 12 in one or both of the regions corresponding to residues 1–38 and 226–520 of SEQ ID NO: 2 or residues 1–38 and 151–445 of SEQ ID NO: 12 by at least one, but by fewer than 15, 10 or 5 amino acid residues, but which does not differ from SEQ ID NO: 2 in the region corresponding to residues 39–225 of SEQ ID NO: 2 or residues 39–150 of SEQ ID NO: 12 (if this comparison requires alignment the sequences should be aligned for maximum homology. "Looped" out sequences from deletions or insertions, or mismatches, are considered differences). In some embodiments the difference is at a non-essential residue or is a conservative substitution, while in others the difference is at an essential residue or is a non-conservative substitution.

A biologically active portion of a 46798 protein should include at least the 46798 peptidase_M10 domain. Moreover, other biologically active portions, in which other regions of the protein are deleted, can be prepared by recombinant techniques and evaluated for one or more of the functional activities of a native 46798 protein.

In a preferred embodiment, the 46798 protein has the amino acid sequence of one of SEQ ID NOs: 2 and 12. In other embodiments, the 46798 protein is substantially identical to one of SEQ ID NOs: 2 and 12. In yet another embodiment, the 46798 protein is substantially identical to one of SEQ ID NOs: 2 and 12 and retains the functional activity of the protein of one of SEQ ID NOs: 2 and 12.

46798 Chimeric or Fusion Proteins

In another aspect, the invention provides 46798 chimeric or fusion proteins. As used herein, a 46798 "chimeric protein" or "fusion protein" includes a 46798 polypeptide linked to a non-46798 polypeptide. A "non-46798 polypeptide" refers to a polypeptide having an amino acid sequence corresponding to a protein which is not substantially homologous to the 46798 protein, e.g., a protein which is different from the 46798 protein and which is derived from the same or a different organism. The 46798 polypeptide of the fusion protein can correspond to all or a portion e.g., a fragment described herein of a 46798 amino acid sequence. In a preferred embodiment, a 46798 fusion protein includes at least one or more biologically active portions of a 46798 protein. The non-46798 polypeptide can be fused to the amino or carboxyl terminus of the 46798 polypeptide.

The fusion protein can include a moiety that has a high affinity for a ligand. For example, the fusion protein can be a GST-46798 fusion protein in which the 46798 sequences are fused to the carboxyl terminus of the GST sequences. Such fusion proteins can facilitate the purification of recombinant 46798. Alternatively, the fusion protein can be a 46798 protein containing a heterologous signal sequence at its amino terminus. In certain host cells (e.g., mammalian host cells), expression and/or secretion of 46798 can be increased through use of a heterologous signal sequence.

Fusion proteins can include all or a part of a serum protein, e.g., an IgG constant region, or human serum albumin.

The 46798 fusion proteins of the invention can be incorporated into pharmaceutical compositions and administered to a subject in vivo. The 46798 fusion proteins can be used to affect the bioavailability of a 46798 substrate. 46798 fusion proteins can be useful therapeutically for the treatment of disorders caused by, for example, (i) aberrant modification or mutation of a gene encoding a 46798 protein; (ii) mis-regulation of the 46798 gene; and (iii) aberrant post-translational modification of a 46798 protein.

Moreover, the 46798-fusion proteins of the invention can be used as immunogens to produce anti-46798 antibodies in a subject, to purify 46798 ligands and in screening assays to identify molecules that inhibit the interaction of 46798 with a 46798 substrate.

Expression vectors are commercially available that already encode a fusion moiety (e.g., a GST polypeptide). A 46798-encoding nucleic acid can be cloned into such an expression vector such that the fusion moiety is linked in-frame to the 46798 protein.

Variants of 46798 Proteins

In another aspect, the invention also features a variant of a 46798 polypeptide, e.g., which functions as an agonist (mimetics) or as an antagonist. Variants of the 46798 proteins can be generated by mutagenesis, e.g., discrete point mutation, the insertion or deletion of sequences or the truncation of a 46798 protein. An agonist of the 46798 proteins can retain substantially the same, or a subset, of the biological activities of the naturally occurring form of a 46798 protein. An antagonist of a 46798 protein can inhibit one or more of the activities of the naturally occurring form of the 46798 protein by, for example, competitively modulating a 46798-mediated activity of a 46798 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 46798 protein.

Variants of a 46798 protein can be identified by screening combinatorial libraries of mutants, e.g., truncation mutants, of a 46798 protein for agonist or antagonist activity.

Libraries of fragments e.g., amino-terminal, carboxyl-terminal, or internal fragments, of a 46798 protein coding sequence can be used to generate a variegated population of fragments for screening and subsequent selection of variants of a 46798 protein.

Variants in which a cysteine residue is added or deleted or in which a residue that is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a technique which enhances the frequency of functional mutants in the libraries, can be used in combination with the screening assays to identify 46798 variants (Arkin et al., 1992, Proc. Natl. Acad. Sci. USA 89:7811–7815; Delgrave et al., 1993, Protein Engr. 6:327–331).

Cell based assays can be exploited to analyze a variegated 46798 library. For example, a library of expression vectors can be transfected into a cell line, e.g., a cell line, which ordinarily responds to 46798 in a substrate-dependent manner. The transfected cells are then contacted with 46798 and the effect of the expression of the mutant on signaling by the 46798 substrate can be detected, e.g., by measuring changes in cell growth and/or enzymatic activity. Plasmid DNA can then be recovered from the cells that score for inhibition, or alternatively, potentiation of signaling by the 46798 substrate, and the individual clones further characterized.

In another aspect, the invention features a method of making a 46798 polypeptide, e.g., a peptide having a non-wild-type activity, e.g., an antagonist, agonist, or super agonist of a naturally-occurring 46798 polypeptide, e.g., a naturally-occurring 46798 polypeptide. The method includes: altering the sequence of a 46798 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 46798 polypeptide a biological activity of a naturally occurring 46798 polypeptide. The method includes: altering the sequence, e.g., by substitution or deletion of one or more residues, of a 46798 polypeptide, e.g., altering the sequence of a non-conserved region, or a domain or residue described herein, and testing the altered polypeptide for the desired activity.

Anti-46798 Antibodies

In another aspect, the invention provides an anti-46798 antibody. The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments which can be generated by treating the antibody with an enzyme such as pepsin.

The antibody can be a polyclonal, monoclonal, recombinant, e.g., a chimeric or humanized, fully-human, non-human, e.g., murine, or single chain antibody. In a preferred embodiment, it has effector function and can fix complement. The antibody can be coupled to a toxin or imaging agent.

A full-length 46798 protein or, antigenic peptide fragment of 46798 can be used as an immunogen or can be used to identify anti-46798 antibodies made with other immunogens, e.g., cells, membrane preparations, and the like. The antigenic peptide of 46798 should include at least 8 amino acid residues of the amino acid sequence shown in one of SEQ ID NOs: 2 and 12 and encompasses an epitope of 46798. Preferably, the antigenic peptide includes at least 10 amino acid residues, more preferably at least 15 amino acid residues, even more preferably at least 20 amino acid residues, and most preferably at least 30 amino acid residues.

Fragments of 46798 which include about residues 39–225 of SEQ ID NO: 2 or about residues 39–150 of SEQ ID NO: 12 can be used to make antibodies, e.g., for use as immunogens or to characterize the specificity of an antibody, against hydrophobic regions of the 46798 protein. Similarly, a fragment of 46798 which include about residues 210–230 or 300–320 of SEQ ID NO: 2 or about residues 135–155 or 225–245 of SEQ ID NO: 12 can be used to make an antibody against a hydrophilic region of the 46798 protein.

Antibodies reactive with, or specific for, any of these regions, or other regions or domains described herein are provided.

Preferred epitopes encompassed by the antigenic peptide are regions of 46798 are located on the surface of the protein, e.g., hydrophilic regions, as well as regions with high antigenicity. For example, an Emini surface probability analysis of the human 46798 protein sequence can be used to indicate the regions that have a particularly high probability of being localized to the surface of the 46798 protein and are thus likely to constitute surface residues useful for targeting antibody production.

In a preferred embodiment the antibody binds an epitope on any domain or region on 46798 proteins described herein.

Chimeric, humanized, but most preferably, completely human antibodies are desirable for applications which include repeated administration, e.g., therapeutic treatment (and some diagnostic applications) of human patients.

The anti-46798 antibody can be a single chain antibody. A single-chain antibody (scFV) can be engineered (e.g., Colcher et al., 1999, Ann. N.Y. Acad. Sci. 880:263–280; Reiter, 1996, Clin. Cancer Res. 2:245–252). The single chain antibody can be dimerized or multimerized to generate multivalent antibodies having specificities for different epitopes of the same target 46798 protein.

In a preferred embodiment, the antibody has reduced or no ability to bind an Fc receptor. For example, it can be an isotype, subtype, fragment or other mutant, which does not support binding to an Fc receptor, e.g., it can have a mutated or deleted Fc receptor binding region.

An anti-46798 antibody (e.g., monoclonal antibody) can be used to isolate 46798 by standard techniques, such as affinity chromatography or immunoprecipitation. Moreover, an anti-46798 antibody can be used to detect 46798 protein (e.g., in a cellular lysate or cell supernatant) in order to evaluate the abundance and pattern of expression of the protein. Anti-46798 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 46798 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 46798 proteins, mutant forms of 46798 proteins, fusion proteins, and the like).

The recombinant expression vectors of the invention can be designed for expression of 46798 proteins in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel (1990, Gene Expression Technology: Methods in Enzymology 185, Academic Press, San Diego). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith et al., 1988, Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 46798 activity assays, (e.g., direct assays or competitive assays described in detail below), or to generate antibodies specific for 46798 proteins. In a preferred embodiment, a fusion protein expressed in a retroviral expression vector of the present invention can be used to infect bone marrow cells that are subsequently transplanted into irradiated recipients. The pathology of the subject recipient is then examined after sufficient time has passed (e.g., six weeks).

To maximize recombinant protein expression in *E. coli*, the protein is expressed in a host bacterial strain with an impaired capacity to proteolytically cleave the recombinant protein (Gottesman, 1990, Gene Expression Technology: Methods in Enzymology 185, Academic Press, San Diego, 119–128). Another strategy is to alter the nucleic acid sequence of the nucleic acid to be inserted into an expression vector so that the individual codons for each amino acid are those preferentially utilized in *E. coli* (Wada et al., 1992, Nucl. Acids Res. 20:2111–2118). Such alteration of nucleic acid sequences of the invention can be carried out by standard DNA synthesis techniques.

The 46798 expression vector can be a yeast expression vector, a vector for expression in insect cells, e.g., a baculovirus expression vector, or a vector suitable for expression in mammalian cells.

When used in mammalian cells, the expression vector's control functions are often provided by viral regulatory elements. For example, commonly used viral promoters are derived from polyoma, adenovirus 2, cytomegalovirus and simian virus 40 (SV40).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al., 1987, Genes Dev. 1:268–277), lymphoid-specific promoters (Calame et al., 1988, Adv. Immunol. 43:235–275), in particular promoters of T cell receptors (Winoto et al., 1989, EMBO J. 8:729–733) and immunoglobulins (Baneji et al., 1983, Cell 33:729–740; Queen et al., 1983, Cell 33:741–748), neuron-specific promoters (e.g., the neurofilament promoter; Byrne et al., 1989, Proc. Natl. Acad. Sci. USA 86:5473–5477), pancreas-specific promoters (Edlund et al., 1985, Science 230:912–916), and mammary gland-specific promoters (e.g., milk whey promoter; U.S. Pat. No. 4,873,316 and European Patent Application publication number 264,166).

Developmentally-regulated promoters are also encompassed, for example, the murine hox promoters (Kessel et al., 1990, Science 249:374–379) and the alpha-fetoprotein promoter (Campes et al., 1989, Genes Dev. 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes, see Weintraub, H. et al. (1986, Trends Genet. 1:Review).

Another aspect the invention provides a host cell which includes a nucleic acid molecule described herein, e.g., a 46798 nucleic acid molecule within a recombinant expression vector or a 46798 nucleic acid molecule containing sequences which allow it to homologously recombine into a specific site of the host cell's genome. The terms "host cell" and "recombinant host cell" are used interchangeably herein. Such terms refer not only to the particular subject cell, but also to the progeny or potential progeny of such a cell. Because certain modifications can occur in succeeding generations due to either mutation or environmental influences, such progeny may not, in fact, be identical to the parent cell, but are included within the scope of the term as used herein.

A host cell can be any prokaryotic or eukaryotic cell. For example, a 46798 protein can be expressed in bacterial cells such as *E. coli*, insect cells, yeast or mammalian cells (such as Chinese hamster ovary (CHO) cells) or COS cells. Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 46798 protein. Accordingly, the invention further provides methods for producing a 46798 protein using the host cells of the invention. In one embodiment, the method includes culturing the host cell of the invention (into which a recombinant expression vector encoding a 46798 protein has been introduced) in a suitable medium such that a 46798 protein is produced. In another embodiment, the method further includes isolating a 46798 protein from the medium or the host cell.

In another aspect, the invention features, a cell or purified preparation of cells which include a 46798 transgene, or which otherwise mal-express 46798. The cell preparation can consist of human or non-human cells, e.g., rodent cells, e.g., mouse or rat cells, rabbit cells, or pig cells. In preferred embodiments, the cell or cells include a 46798 transgene, e.g., a heterologous form of a 46798, e.g., a gene derived from humans (in the case of a non-human cell). The 46798 transgene can be mal-expressed, e.g., over-expressed or under-expressed. In other preferred embodiments, the cell or cells include a gene that mal-expresses an endogenous 46798, e.g., a gene the expression of which is disrupted, e.g., a knockout. Such cells can serve as a model for studying disorders that are related to mutated or mal-expressed 46798 alleles or for use in drug screening.

In another aspect, the invention includes, a human cell, e.g., a hematopoietic stem cell, transformed with nucleic acid that encodes a subject 46798 polypeptide.

Also provided are cells, preferably human cells, e.g., human hematopoietic or fibroblast cells, in which an endogenous 46798 is under the control of a regulatory sequence that does not normally control expression of the endogenous 46798 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 46798 gene. For example, an endogenous 46798 gene that is "transcriptionally silent," e.g., not normally expressed, or expressed only at very low levels, can be activated by inserting a regulatory element that is capable of promoting the expression of a normally expressed gene product in that cell. Techniques such as targeted homologous recombination, can be used to insert the heterologous DNA as described (e.g., U.S. Pat. No. 5,272,071; PCT publication number WO 91/06667).

Transgenic Animals

The invention provides non-human transgenic animals. Such animals are useful for studying the function and/or activity of a 46798 protein and for identifying and/or evaluating modulators of 46798 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 46798 gene has been altered, e.g., by homologous recombination between the endogenous gene and an exogenous DNA molecule introduced into a cell of the animal (e.g., an embryonic cell of the animal, prior to development of the animal).

Intronic sequences and polyadenylation signals can also be included in the transgene to increase the efficiency of expression of the transgene. A tissue-specific regulatory sequence(s) can be operably linked to a transgene of the invention to direct expression of a 46798 protein to particular cells. A transgenic founder animal can be identified based upon the presence of a 46798 transgene in its genome and/or expression of 46798 mRNA in tissues or cells of the animals. A transgenic founder animal can then be used to breed additional animals carrying the transgene. Moreover, transgenic animals carrying a transgene encoding a 46798 protein can further be bred to other transgenic animals carrying other transgenes.

46798 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk- or egg-specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). The isolated nucleic acid molecules of the invention can be used, for example, to express a 46798 protein (e.g., via a recombinant expression vector in a host cell in gene therapy applications), to detect a 46798 mRNA (e.g., in a biological sample), to detect a genetic alteration in a 46798 gene and to modulate 46798 activity, as described further below. The 46798 proteins can be used to treat disorders characterized by insufficient or excessive production of a 46798 substrate or production of 46798 inhibitors. In addition, the 46798 proteins can be used to screen for naturally occurring 46798 substrates, to screen for drugs or compounds which modulate 46798 activity, as well as to treat disorders characterized by insufficient or excessive production of 46798 protein or production of 46798 protein forms which have decreased, aberrant or unwanted activity compared to 46798 wild-type protein. Exemplary disorders include those in which degradation of ECM proteins is aberrant (e.g., cancer, arthritis, disorders involving aberrant angiogenesis, and cardiovascular diseases such as heart failure). Moreover, the anti-46798 antibodies of the invention can be used to detect and isolate 46798 proteins, regulate the bioavailability of 46798 proteins, and modulate 46798 activity.

A method of evaluating a compound for the ability to interact with, e.g., bind to, a subject 46798 polypeptide is provided. The method includes: contacting the compound with the subject 46798 polypeptide; and evaluating the ability of the compound to interact with, e.g., to bind or form a complex with, the subject 46798 polypeptide. This method can be performed in vitro, e.g., in a cell free system, or in vivo, e.g., in a two-hybrid interaction trap assay. This method can be used to identify naturally-occurring molecules that interact with a subject 46798 polypeptide. It can also be used to find natural or synthetic inhibitors of a subject 46798 polypeptide. Screening methods are discussed in more detail below.

Screening Assays

The invention provides screening methods (also referred to herein as "assays") for identifying modulators, i.e., candidate or test compounds or agents (e.g., proteins, peptides, peptidomimetics, peptoids, small molecules or other drugs) which bind with 46798 proteins, have a stimulatory or inhibitory effect on, for example, 46798 expression or 46798 activity, or have a stimulatory or inhibitory effect on, for example, the expression or activity of a 46798 substrate. Compounds thus identified can be used to modulate the activity of target gene products (e.g., 46798 genes) in a therapeutic protocol, to elaborate the biological function of the target gene product, or to identify compounds that disrupt normal target gene interactions.

In one embodiment, the invention provides assays for screening candidate or test compounds that are substrates of a 46798 protein or polypeptide or a biologically active portion thereof. In another embodiment, the invention provides assays for screening candidate or test compounds that bind to or modulate the activity of a 46798 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; e.g., Zuckermann et al., 1994, J. Med. Chem. 37:2678–2685); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries have been described (e.g., DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233).

Libraries of compounds can be presented in solution (e.g., Houghten, 1992, Biotechniques 13:412–421), or on beads (Lam, 1991, Nature 354:82–84), chips (Fodor, 1993, Nature 364:555–556), bacteria (U.S. Pat. No. 5,223,409), spores (U.S. Pat. No. 5,223,409), plasmids (Cull et al., 1992, Proc. Natl. Acad. Sci. USA 89:1865–1869), or on phage (Scott et al., 1990, Science 249:386–390; Devlin, 1990, Science 249:404–406; Cwirla et al., 1990, Proc. Natl. Acad. Sci. USA 87:6378–6382; Felici, 1991, J. Mol. Biol. 222:301–310; U.S. Pat. No. 5,223,409).

In one embodiment, an assay is a cell-based assay in which a cell which expresses a 46798 protein or biologically active portion thereof is contacted with a test compound, and the ability of the test compound to modulate 46798 activity is determined. Determining the ability of the test compound to modulate 46798 activity can be accomplished by monitoring, for example, changes in enzymatic activity. The cell, for example, can be of mammalian origin.

The ability of the test compound to modulate 46798 binding to a compound, e.g., a 46798 substrate, or to bind to 46798 can also be evaluated. This can be accomplished, for example, by coupling the compound, e.g., the substrate, with a radioisotope or enzymatic label such that binding of the compound, e.g., the substrate, to 46798 can be determined by detecting the labeled compound, e.g., substrate, in a complex. Alternatively, 46798 could be coupled with a radioisotope or enzymatic label to monitor the ability of a test compound to modulate 46798 binding to a 46798 substrate in a complex. For example, compounds (e.g., 46798 substrates) can be labeled with $^{125}$I, $^{35}$S, $^{14}$C, or $^{3}$H, either directly or indirectly, and the radioisotope detected by direct counting of radio-emission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 46798 substrate) to interact with 46798 with or without the labeling of any of the interactants can be evaluated. For example, a microphysiometer can be used to detect the interaction of a compound with 46798 without the labeling of either the compound or the 46798 (McConnell et al., 1992, Science 257:1906–1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 46798.

In yet another embodiment, a cell-free assay is provided in which a 46798 protein or biologically active portion thereof is contacted with a test compound and the ability of the test compound to bind to the 46798 protein or biologically active portion thereof is evaluated. Preferred biologically active portions of the 46798 proteins to be used in assays of the present invention include fragments that participate in interactions with non-46798 molecules, e.g., fragments with high surface probability scores.

Soluble and/or membrane-bound forms of isolated proteins (e.g., 46798 proteins or biologically active portions thereof) can be used in the cell-free assays of the invention. When membrane-bound forms of the protein are used, it can be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-{(3-cholamidopropyl) dimethylamminio}-1-propane sulfonate (CHAPS), 3-{(3-cholamidopropyl) dimethylamminio}-2-hydroxy-1-propane sulfonate (CHAPSO), or N-dodecyl-N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET; e.g., U.S. Pat. No. 5,631,169; U.S. Pat. No. 4,868,103). A fluorophore label is selected such that a first donor molecule's emitted fluorescent energy will be absorbed by a fluorescent label on a second, 'acceptor' molecule, which in turn is able to fluoresce due to the absorbed energy. Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 46798 protein to bind to a target molecule can be accomplished using real-time biomolecular interaction analysis (BIA; e.g., Sjolander et al., 1991, Anal. Chem. 63:2338–2345; Szabo et al., 1995, Curr. Opin. Struct. Biol. 5:699–705). "Surface plasmon resonance" (SPR) or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of SPR), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It can be desirable to immobilize either 46798, an anti-46798 antibody or its target molecule to facilitate separation of complexed from non-complexed forms of one or both of the proteins, as well as to accommodate automation of the assay. Binding of a test compound to a 46798 protein, or interaction of a 46798 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/46798 fusion proteins or glutathione-S-transferase/target fusion proteins can be adsorbed onto glutathione Sepharose™ beads (Sigma Chemical, St. Louis, Mo.) or glutathione-derivatized microtiter plates, which are then combined with the test compound or the test compound and either the non-adsorbed target protein or 46798 protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 46798 binding or activity determined using standard techniques.

Other techniques for immobilizing either a 46798 protein or a target molecule on matrices include using conjugation of biotin and streptavidin. Biotinylated 46798 protein or target molecules can be prepared from biotin-N-hydroxy-succinimide using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, non-reacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 46798 protein or target molecules but which do not interfere with binding of the 46798 protein to its target molecule. Such antibodies can be derivatized to the wells of the plate, and unbound target or 46798 protein trapped in the wells by antibody conjugation. Methods for detecting such complexes, in addition to those described above for the GST-immobilized complexes, include immunodetection of complexes using antibodies reactive with the 46798 protein or target molecule, as well as enzyme-linked assays which rely on detecting an enzymatic activity associated with the 46798 protein or target molecule.

Alternatively, cell free assays can be conducted in a liquid phase. In such an assay, the reaction products are separated from non-reacted components, by any of a number of standard techniques, including, but not limited to: differential centrifugation (e.g., Rivas et al., 1993, Trends Biochem. Sci. 18:284–287); chromatography (e.g., gel filtration chromatography or ion-exchange chromatography); electrophoresis (e.g., Ausubel et al., eds., 1999, Current Protocols in Molecular Biology, J. Wiley, New York); and immunoprecipitation (e.g., Ausubel, supra). Such resins and chromatographic techniques are known to one skilled in the art (e.g., Heegaard, 1998, J. Mol. Recognit. 11:141–148; Hage et al., 1997, J. Chromatogr. B Biomed. Sci. Appl. 699:499–525). Further, fluorescence energy transfer can also be conveniently utilized, as described herein, to detect binding without further purification of the complex from solution.

In a preferred embodiment, the assay includes contacting the 46798 protein or biologically active portion thereof with a known compound which binds 46798 to form an assay mixture, contacting the assay mixture with a test compound, and determining the ability of the test compound to interact with a 46798 protein, wherein determining the ability of the test compound to interact with a 46798 protein includes determining the ability of the test compound to preferentially bind to 46798 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 46798 genes herein identified. In an alternative embodiment, the invention provides methods for determining the ability of the test compound to modulate the activity of a 46798 protein through modulation of the activity of a downstream effector of a 46798 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, non-reacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from non-reacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 46798 proteins can be used as "bait proteins" in a two-hybrid assay or three-hybrid assay (e.g., U.S. Pat. No. 5,283,317; Zervos et al., 1993, Cell 72:223–232; Madura et al., 1993, J. Biol. Chem. 268:12046–12054; Bartel et al., 1993, Biotechniques 14:920–924; Iwabuchi et al., 1993, Oncogene 8:1693–1696; PCT publication number WO 94/10300), to identify other proteins, which bind to or interact with 46798 ("46798-binding proteins" or "46798-bp") and are involved in 46798 activity. Such 46798-bps can be activators or inhibitors of signals by the 46798 proteins or 46798 targets as, for example, downstream elements of a 46798-mediated signaling pathway.

The two-hybrid system is based on the modular nature of most transcription factors, which consist of separable DNA-binding and activation domains. Briefly, the assay utilizes two different DNA constructs. In one construct, the gene that codes for a 46798 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively, the 46798 protein can be fused to the activator domain). If the "bait" and the "prey" proteins are able to interact in vivo forming a 46798-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein that interacts with the 46798 protein.

In another embodiment, modulators of 46798 expression are identified. For example, a cell or cell free mixture is contacted with a candidate compound and the expression of 46798 mRNA or protein evaluated relative to the level of expression of 46798 mRNA or protein in the absence of the candidate compound. When expression of 46798 mRNA or protein is greater in the presence of the candidate compound than in its absence, the candidate compound is identified as a stimulator of 46798 mRNA or protein expression. Alternatively, when expression of 46798 mRNA or protein is less (i.e., statistically significantly less) in the presence of the candidate compound than in its absence, the candidate compound is identified as an inhibitor of 46798 mRNA or protein expression. The level of 46798 mRNA or protein expression can be determined by methods described herein for detecting 46798 mRNA or protein.

In another aspect, the invention pertains to a combination of two or more of the assays described herein. For example, a modulating agent can be identified using a cell-based or a cell free assay, and the ability of the agent to modulate the activity of a 46798 protein can be confirmed in vivo, e.g., in an animal such as an animal model for a disease.

This invention further pertains to novel agents identified by the above-described screening assays. Accordingly, it is within the scope of this invention to further use an agent identified as described herein (e.g., a 46798 modulating agent, an antisense 46798 nucleic acid molecule, a 46798-specific antibody, or a 46798-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome, e.g., to locate gene regions associated with genetic disease or to associate 46798 with a disease; (ii) identify an individual from a minute biological sample (tissue typing); and (iii) aid in forensic identification of a biological sample. These applications are described in the subsections below.

Chromosome Mapping

The 46798 nucleotide sequences or portions thereof can be used to map the location of the 46798 genes on a chromosome. This process is called chromosome mapping. Chromosome mapping is useful in correlating the 46798 sequences with genes associated with disease.

Briefly, 46798 genes can be mapped to chromosomes by preparing PCR primers (preferably 15–25 base pairs in length) from the 46798 nucleotide sequence (e.g., one of SEQ ID NOs: 1, 3, 11, and 13). These primers can then be used for PCR screening of somatic cell hybrids containing individual human chromosomes. Only those hybrids containing the human gene corresponding to the 46798 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes (D'Eustachio et al., 1983, Science 220:919–924).

Other mapping strategies e.g., in situ hybridization as described (Fan et al., 1990, Proc. Natl. Acad. Sci. USA 87:6223–6227), pre-screening with labeled flow-sorted chromosomes, and pre-selection by hybridization to chromosome specific cDNA libraries can be used to map 46798 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of FISH, see Verma et al. (1988, Human Chromosomes: A Manual of Basic Techniques, Pergamon Press, New York).

Reagents for chromosome mapping can be used individually to mark a single chromosome or a single site on that chromosome, or panels of reagents can be used for marking multiple sites and/or multiple chromosomes. Reagents corresponding to non-coding regions of the genes are typically preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data (such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), as described (e.g., Egeland et al., 1987, Nature, 325:783–787).

Moreover, differences in the DNA sequences between individuals affected and unaffected with a disease associated with the 46798 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 46798 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 46798 nucleotide sequence described herein can be used to prepare PCR primers homologous to the 5'- and 3'-ends of the sequence. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the non-coding regions. Each of the sequences described herein can, to some degree, be used as a standard against which DNA from an individual can be compared for identification purposes. Because greater numbers of polymorphisms occur in the non-coding regions, fewer sequences are necessary to differentiate individuals. The non-coding sequences of one of SEQ ID NOs: 1 and 11 can provide positive individual identification with a panel of perhaps 10 to 1,000 primers which each yield a non-coding amplified sequence of 100 bases. If predicted coding sequences are used, such as those in one of SEQ ID NOs: 3 and 13, a more appropriate number of primers for positive individual identification would be 500–2,000.

If a panel of reagents from 46798 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 46798 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual nucleotide sequence information can be used for identification as an accurate alternative to patterns formed by restriction enzyme generated fragments. Sequences targeted to non-coding regions of one of SEQ ID NOs: 1 and 11 (e.g., fragments having a length of at least 20 nucleotide residues, preferably at least 30 nucleotide residues) are particularly appropriate for this use.

The 46798 nucleotide sequences described herein can further be used to provide polynucleotide reagents, e.g., labeled or label-able probes which can be used in, for example, an in situ hybridization technique, to identify a specific tissue, e.g., a tissue containing hematopoietic cells. This can be very useful in cases where a forensic pathologist is presented with a tissue of unknown origin. Panels of such 46798 probes can be used to identify tissue by species and/or by organ type.

In a similar fashion, these reagents, e.g., 46798 primers or probes can be used to screen tissue culture for contamination (i.e., to screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides a method of determining if a subject is at risk for a disorder related to a lesion in, or the malexpression of, a gene that encodes a 46798 polypeptide.

Such disorders include, e.g., a disorder associated with the malexpression of a 46798 polypeptide, e.g., an immune disorder or a neoplastic disorder.

The method includes one or more of the following:

(i) detecting, in a tissue of the subject, the presence or absence of a mutation which affects the expression of the 46798 gene, or detecting the presence or absence of a mutation in a region which controls the expression of the gene, e.g., a mutation in the 5'-control region;

(ii) detecting, in a tissue of the subject, the presence or absence of a mutation which alters the structure of the 46798 gene;

(iii) detecting, in a tissue of the subject, the malexpression of the 46798 gene at the mRNA level, e.g., detecting a non-wild-type level of a mRNA; and (iv) detecting, in a tissue of the subject, the malexpression of the gene at the protein level, e.g., detecting a non-wild-type level of a 46798 polypeptide.

In preferred embodiments the method includes: ascertaining the existence of at least one of: a deletion of one or more nucleotides from the 46798 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO: 1, SEQ ID NO: 11, or naturally occurring mutants thereof, or 5'- or 3'-flanking sequences naturally associated with the 46798 gene; (ii) exposing the probe/primer to nucleic acid of the tissue; and detecting the presence or absence of the genetic lesion by hybridization of the probe/primer to the nucleic acid, e.g., by in situ hybridization.

In preferred embodiments, detecting the malexpression includes ascertaining the existence of at least one of: an alteration in the level of a messenger RNA transcript of the 46798 gene; the presence of a non-wild-type splicing pattern of a messenger RNA transcript of the gene; or a non-wild-type level of 46798 RNA or protein.

Methods of the invention can be used for prenatal screening or to determine if a subject's offspring will be at risk for a disorder.

In preferred embodiments the method includes determining the structure of a 46798 gene, an abnormal structure being indicative of risk for the disorder.

In preferred embodiments the method includes contacting a sample form the subject with an antibody to the 46798 protein or a nucleic acid, which hybridizes specifically with the gene. These and other embodiments are discussed below.

Diagnostic and Prognostic Assays

The presence, level, or absence of 46798 protein or nucleic acid in a biological sample can be evaluated by obtaining a biological sample from a test subject and contacting the biological sample with a compound or an agent capable of detecting 46798 protein or nucleic acid (e.g., mRNA, genomic DNA) that encodes 46798 protein such that the presence of 46798 protein or nucleic acid is detected in the biological sample. The term "biological sample" includes tissues, cells and biological fluids isolated from a subject, as well as tissues, cells and fluids present within a subject. A preferred biological sample is serum. The level of expression of the 46798 gene can be measured in a number of ways, including, but not limited to: measuring the mRNA encoded by the 46798 genes; measuring the amount of protein encoded by the 46798 genes; or measuring the activity of the protein encoded by the 46798 genes.

The level of mRNA corresponding to the 46798 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 46798 nucleic acid, such as the nucleic acid of SEQ ID NO: 1, or a portion thereof, such as an oligonucleotide of at least 7, 15, 30, 50, 100, 250 or 500 nucleotides in length and sufficient to specifically hybridize under stringent conditions to 46798 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 46798 genes.

The level of mRNA in a sample that is encoded by 46798 can be evaluated with nucleic acid amplification, e.g., by RT-PCR (U.S. Pat. No. 4,683,202), ligase chain reaction (Barany, 1991, Proc. Natl. Acad. Sci. USA 88:189–193), self-sustained sequence replication (Guatelli et al., 1990, Proc. Natl. Acad. Sci. USA 87:1874–1878), transcriptional amplification system (Kwoh et al., 1989, Proc. Natl. Acad. Sci. USA 86:1173–1177), Q-Beta Replicase (Lizardi et al., 1988, Bio/Technology 6:1197), rolling circle replication (U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5'- or 3'-regions of a 46798 gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence between the primers.

For in situ methods, a cell or tissue sample can be prepared/processed and immobilized on a support, typically a glass slide, and then contacted with a probe that can hybridize to mRNA that encodes the 46798 gene being analyzed.

In another embodiment, the methods include further contacting a control sample with a compound or agent capable of detecting 46798 mRNA, or genomic DNA, and comparing the presence of 46798 mRNA or genomic DNA in the control sample with the presence of 46798 mRNA or genomic DNA in the test sample.

A variety of methods can be used to determine the level of protein encoded by 46798. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 46798 protein in a biological sample in vitro as well as in vivo. In vitro techniques for detection of 46798 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 46798 protein include introducing into a subject a labeled anti-46798 antibody. For example, the antibody can be labeled with a radioactive marker whose presence and location in a subject can be detected by standard imaging techniques.

In another embodiment, the methods further include contacting the control sample with a compound or agent capable of detecting 46798 protein, and comparing the presence of 46798 protein in the control sample with the presence of 46798 protein in the test sample.

The invention also includes kits for detecting the presence of 46798 in a biological sample. For example, the kit can include a compound or agent capable of detecting 46798 protein or mRNA in a biological sample, and a standard. The compound or agent can be packaged in a suitable container. The kit can further comprise instructions for using the kit to detect 46798 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably-labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein-stabilizing agent. The kit can also includes components necessary for detecting the detectable agent (e.g., an enzyme or a substrate). The kit can also contain a control sample or a series of control samples that can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with malexpressed, aberrant or unwanted 46798 expression or activity. As used herein, the term "unwanted" includes an unwanted phenomenon involved in a biological response such as pain or deregulated cell proliferation.

In one embodiment, a disease or disorder associated with aberrant or unwanted 46798 expression or activity is identified. A test sample is obtained from a subject and 46798 protein or nucleic acid (e.g., mRNA or genomic DNA) is evaluated, wherein the level, e.g., the presence or absence, of 46798 protein or nucleic acid is diagnostic for a subject having or at risk of developing a disease or disorder associated with aberrant or unwanted 46798 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 46798 expression or activity. For example, such methods can be used to determine whether a subject can be effectively treated with an agent that modulates 46798 expression or activity.

The methods of the invention can also be used to detect genetic alterations in a 46798 gene, thereby determining if a subject with the altered gene is at risk for a disorder characterized by misregulation in 46798 protein activity or nucleic acid expression, such as a disorder associated with hematopoiesis or an immune disorder. In preferred embodiments, the methods include detecting, in a sample from the subject, the presence or absence of a genetic alteration characterized by at least one of an alteration affecting the integrity of a gene encoding a 46798 protein, or the malexpression of the 46798 gene. For example, such genetic alterations can be detected by ascertaining the existence of at least one of 1) a deletion of one or more nucleotides from a 46798 gene; 2) an addition of one or more nucleotides to a 46798 gene; 3) a substitution of one or more nucleotides of a 46798 gene, 4) a chromosomal rearrangement of a 46798 gene; 5) an alteration in the level of a messenger RNA transcript of a 46798 gene, 6) aberrant modification of a 46798 gene, such as of the methylation pattern of the genomic DNA, 7) the presence of a non-wild-type splicing pattern of a messenger RNA transcript of a 46798 gene, 8) a non-wild-type level of a 46798 protein, 9) allelic loss of a 46798 gene, and 10) inappropriate post-translational modification of a 46798 protein.

An alteration can be detected without a probe/primer in a polymerase chain reaction, such as anchor PCR or RACE-PCR, or, alternatively, in a ligation chain reaction (LCR), the latter of which can be particularly useful for detecting point mutations in the 46798 gene. This method can include the steps of collecting a sample of cells from a subject, isolating nucleic acid (e.g., genomic, mRNA or both) from the sample, contacting the nucleic acid sample with one or more primers which specifically hybridize to a 46798 gene under conditions such that hybridization and amplification of the 46798 gene occurs (if present), and detecting the presence or absence of an amplification product, or detecting the size of the amplification product and comparing the length to a control sample. It is anticipated that PCR and/or LCR can be desirable to use as a preliminary amplification step in conjunction with any of the techniques used for detecting mutations described herein.

Alternative amplification methods include: self sustained sequence replication (Guatelli et al., 1990, Proc. Natl. Acad. Sci. USA 87:1874–1878), transcriptional amplification system (Kwoh et al., 1989, Proc. Natl. Acad. Sci. USA 86:1173–1177), Q-Beta Replicase (Lizardi et al., 1988, Bio/Technology 6:1197), or other nucleic acid amplification methods, followed by the detection of the amplified molecules using techniques known to those of skill in the art.

In another embodiment, mutations in a 46798 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis, and compared. Differences in fragment length sizes between sample and control DNA indicates mutations in the sample DNA. Moreover, the use of sequence specific ribozymes (e.g., U.S. Pat. No. 5,498,531) can be used to score for the presence of specific mutations by development or loss of a ribozyme cleavage site.

In other embodiments, genetic mutations in 46798 can be identified by hybridizing a sample to control nucleic acids, e.g., DNA or RNA, by, e.g., two-dimensional arrays, or, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin et al., 1996, Hum. Mutat. 7:244–255; Kozal et al., 1996, Nature Med. 2:753–759). For example, genetic mutations in 46798 can be identified in two-dimensional arrays containing light-generated DNA probes as described (Cronin et al., supra). Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 46798 gene and detect mutations by comparing the sequence of the sample 46798 with the corresponding wild-type (control) sequence. Automated sequencing procedures can be utilized when performing the diagnostic assays (1995, Biotechniques 19:448), including sequencing by mass spectrometry.

Other methods for detecting mutations in the 46798 gene include methods in which protection from cleavage agents is used to detect mismatched bases in RNA/RNA or RNA/DNA heteroduplexes (Myers et al., 1985, Science 230:1242; Cotton et al., 1988, Proc. Natl. Acad. Sci. USA 85:4397; Saleeba et al., 1992, Meth. Enzymol. 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 46798 cDNAs obtained from samples of cells. For example, the mutY enzyme of *E. coli* cleaves A at G/A mismatches and the thymidine DNA glycosylase from HeLa cells cleaves T at G/T mismatches (Hsu et al., 1994, Carcinogenesis 15:1657–1662; U.S. Pat. No. 5,459,039).

In other embodiments, alterations in electrophoretic mobility will be used to identify mutations in 46798 genes. For example, single strand conformation polymorphism (SSCP) can be used to detect differences in electrophoretic mobility between mutant and wild-type nucleic acids (Orita et al., 1989, Proc. Natl. Acad. Sci. USA 86:2766; Cotton, 1993, Mutat. Res. 285:125–144; Hayashi, 1992, Genet. Anal. Tech. Appl. 9:73–79). Single-stranded DNA fragments of sample and control 46798 nucleic acids will be denatured and allowed to re-nature. The secondary structure of single-stranded nucleic acids varies according to sequence, the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al., 1991, Trends Genet 7:5).

In yet another embodiment, the movement of mutant or wild-type fragments in polyacrylamide gels containing a gradient of denaturant is assayed using denaturing gradient gel electrophoresis (DGGE) (Myers et al., 1985, Nature 313:495). When DGGE is used as the method of analysis, DNA will be modified to insure that it does not completely denature, for example by adding a GC clamp of approximately 40 base pairs of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension (Saiki et al., 1986, Nature 324:163; Saiki et al., 1989, Proc. Natl. Acad. Sci. USA 86:6230).

Alternatively, allele specific amplification technology that depends on selective PCR amplification can be used in conjunction with the instant invention. Oligonucleotides used as primers for specific amplification can carry the mutation of interest in the center of the molecule (so that amplification depends on differential hybridization; Gibbs et al., 1989, Nucl. Acids Res. 17:2437–2448) or at the extreme 3'-end of one primer where, under appropriate conditions, mismatch can prevent, or reduce polymerase extension (Prossner, 1993, Tibtech 11:238). In addition, it can be desirable to introduce a novel restriction site in the region of the mutation to create cleavage-based detection (Gasparini et al., 1992, Mol. Cell Probes 6:1). It is anticipated that in certain embodiments, amplification can also be performed using Taq ligase for amplification (Barany, 1991, Proc. Natl. Acad. Sci. USA 88:189). In such cases, ligation will occur only if there is a perfect match at the 3'-end of the 5'-sequence making it possible to detect the presence of a known mutation at a specific site by looking for the presence or absence of amplification.

The methods described herein can be performed, for example, using pre-packaged diagnostic kits comprising at least one probe nucleic acid or antibody reagent described herein, which can be conveniently used, e.g., in clinical settings to diagnose patients exhibiting symptoms or family history of a disease or illness involving a 46798 gene.

Use of 46798 Molecules as Surrogate Markers

The 46798 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 46798 molecules of the invention can be detected, and can be correlated with one or more biological states in vivo. For example, the 46798 molecules of the invention can serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers can serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease can be made using cholesterol levels as a surrogate marker, and an analysis of HIV infection can be made using HIV RNA levels as a surrogate marker, well in advance of the undesirable clinical outcomes of myocardial infarction or fully-developed AIDS). Examples of the use of surrogate markers have been described (e.g., Koomen et al., 2000, J. Mass. Spectrom. 35:258–264; James, 1994, AIDS Treat. News Arch. 209).

The 46798 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker can be indicative of the concentration of the drug in a biological tissue, in that the marker is either expressed or transcribed or not expressed or transcribed in that tissue in relationship to the level of the drug. In this fashion, the distribution or uptake of the drug can be monitored by the pharmacodynamic marker. Similarly, the presence or quantity of the pharmacodynamic marker can be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug can be sufficient to activate multiple rounds of marker (e.g., a 46798 marker) transcription or expression, the amplified marker can be in a quantity which is more readily detectable than the drug itself. Also, the marker can be more easily detected due to the nature of the marker itself; for example, using the methods described herein, anti-46798 antibodies can be employed in an immune-based detection system for a 46798 protein marker, or 46798-specific radiolabeled probes can be used to detect a 46798 mRNA marker. Furthermore, the use of a pharmacodynamic marker can offer mechanism-based prediction of risk due to drug treatment beyond the range of possible direct observations. Examples of the use of pharmacodynamic markers have been described (e.g., U.S. Pat. No. 6,033,862; Hattis et al., 1991, Env. Health Perspect. 90: 229–238; Schentag, 1999, Am. J. Health-Syst. Pharm. 56 Suppl. 3: S21–S24; Nicolau, 1999, Am, J. Health-Syst. Pharm. 56 Suppl. 3: S16–S20).

The 46798 molecules of the invention are also useful as pharmacogenomic markers. As used herein, a "pharmacogenomic marker" is an objective biochemical marker which correlates with a specific clinical drug response or susceptibility in a subject (e.g., McLeod et al., 1999, Eur. J. Cancer 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, can be selected. For example, based on the presence or quantity of RNA, or protein (e.g., 46798 protein or RNA) for specific tumor markers in a subject, a drug or course of treatment can be selected that is optimized for the treatment of the specific tumor likely to be present in the subject. Similarly, the presence or absence of a specific sequence mutation in 46798 DNA can correlate to 46798 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-46798 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including an agent in the composition that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents and/or adjuvant materials can be included as part of the composition. The tablets, pills, capsules, troches and the like can contain any of the following ingredients, or compounds of a similar nature: a binder, such as microcrystalline cellulose, gum tragacanth or gelatin; an excipient, such as starch or lactose; a disintegrating agent, such as alginic acid, Primogel™, or corn starch; a lubricant, such as magnesium stearate or Sterotes™; a glidant, such as colloidal silicon dioxide; a sweetening agent, such as sucrose or saccharin; or a flavoring agent, such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells using monoclonal antibodies directed towards viral antigens) can also be used as pharmaceutically acceptable carriers. These can be prepared according to described methods (e.g., U.S. Pat. No. 4,522,811).

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 milligrams per kilogram body weight, preferably about 0.01 to 25 milligrams per kilogram body weight, more preferably about 0.1 to 20 milligrams per kilogram body weight, and even more preferably about 1 to 10 milligrams per kilogram, 2 to 9 milligrams per kilogram, 3 to 8 milligrams per kilogram, 4 to 7 milligrams per kilogram, or 5 to 6 milligrams per kilogram body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 milligrams per kilogram of body weight (generally 10 to 20 milligrams per kilogram). If the antibody is to act in the brain, a dosage of 50 to 100 milligrams per kilogram is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for the lipidation of antibodies is described by Cruikshank et al. (1997, J. AIDS Hum. Retrovir. 14:193).

The present invention encompasses agents that modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including hetero-organic and organo-metallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) can be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, and the drug moiety is not to be construed as limited to classical chemical therapeutic agents. For example, the drug moiety can be a protein or polypeptide possessing a desired biological activity. Such proteins can include, for example, a toxin such as abrin, ricin A, gelonin, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukins-1, -2, and -6, granulocyte macrophage colony stimulating factor, granulocyte colony stimulating factor, or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No.

5,328,470) or by stereotactic injection (e.g., Chen et al., 1994, Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 46798 expression or activity. With regards to both prophylactic and therapeutic methods of treatment, such treatments can be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype," or "drug response genotype".) Thus, another aspect of the invention provides methods for tailoring an individual's prophylactic or therapeutic treatment with either the 46798 molecules of the present invention or 46798 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing a disease or condition in a subject associated with an aberrant or unwanted 46798 expression or activity, by administering to the subject a 46798 or an agent which modulates 46798 expression, or at least one 46798 activity. Subjects at risk for a disease which is caused or contributed to by aberrant or unwanted 46798 expression or activity can be identified by, for example, any or a combination of diagnostic or prognostic assays as described herein. Administration of a prophylactic agent can occur prior to the manifestation of symptoms characteristic of the 46798 aberrance, such that a disease or disorder is prevented or, alternatively, delayed in its progression. Depending on the type of 46798 aberrance, for example, a 46798, 46798 agonist or 46798 antagonist agent can be used for treating the subject. The appropriate agent can be determined based on screening assays described herein.

It is possible that some 46798 disorders can be caused, at least in part, by an abnormal level of gene product, or by the presence of a gene product exhibiting abnormal activity. As such, the reduction in the level and/or activity of such gene products would bring about the amelioration of disorder symptoms.

As discussed, successful treatment of 46798 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 46798 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules can be utilized in treating or preventing a disease characterized by 46798 expression is through the use of aptamer molecules specific for 46798 protein. Aptamers are nucleic acid molecules having a tertiary structure that permits them to specifically bind to protein ligands (e.g., Osborne et al., 1997, Curr. Opin. Chem. Biol. 1:5–9; Patel, 1997, Curr. Opin. Chem. Biol. 1:32–46). Since nucleic acid molecules can in many cases be more conveniently introduced into target cells than therapeutic protein molecules can be, aptamers offer a method by which 46798 protein activity can be specifically decreased without the introduction of drugs or other molecules which can have pluripotent effects.

Antibodies can be generated that are both specific for target gene product and that reduce target gene product activity. Such antibodies may, therefore, by administered in instances whereby negative modulatory techniques are appropriate for the treatment of 46798 disorders.

In circumstances wherein injection of an animal or a human subject with a 46798 protein or epitope for stimulating antibody production is harmful to the subject, it is possible to generate an immune response against 46798 through the use of anti-idiotypic antibodies (e.g., Herlyn, 1999, Ann. Med. 31:66–78; Bhattacharya-Chatterjee et al., 1998, Cancer Treat. Res. 94:51–68). If an anti-idiotypic antibody is introduced into a mammal or human subject, it should stimulate the production of anti-anti-idiotypic antibodies, which should be specific to the 46798 protein. Vaccines directed to a disease characterized by 46798 expression can also be generated in this fashion.

In instances where the target antigen is intracellular and whole antibodies are used, internalizing antibodies can be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (e.g., Marasco et al., 1993, Proc. Natl. Acad. Sci. USA 90:7889–7893).

The identified compounds that inhibit target gene expression, synthesis and/or activity can be administered to a patient at therapeutically effective doses to prevent, treat or ameliorate 46798 disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays can utilize antibody mimics and/or "biosensors" that have been created through molecular imprinting techniques. The compound which is able to modulate 46798 activity is used as a template, or "imprinting molecule," to spatially organize polymerizable monomers prior to their polymerization with catalytic reagents. The subsequent removal of the imprinted molecule leaves a polymer matrix that contains a repeated "negative image" of the compound and is able to selectively rebind the molecule under biological assay conditions. Detailed reviews of this technique appear in the art (Ansell et al., 1996, Curr. Opin. Biotechnol. 7:89–94; Shea, 1994, Trends Polymer Sci. 2:166–173). Such "imprinted" affinity matrixes are amenable to ligand-binding assays, whereby the immobilized monoclonal antibody component is replaced by an appropriately imprinted matrix (e.g., a matrix described in Vlatakis et al., 1993, Nature 361:645–647. Through the use of isotope-labeling, the "free" concentration of compound which modulates the expression or activity of 46798 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiber optic devices, in turn allowing the dose in a test subject to be quickly optimized based on its individual $IC_{50}$. A rudimentary example of such a "biosensor" is discussed in Kriz et al. (1995, Anal. Chem. 67:2142–2144).

Another aspect of the invention pertains to methods of modulating 46798 expression or activity for therapeutic purposes. Accordingly, in an exemplary embodiment, the modulatory method of the invention involves contacting a cell with a 46798 or agent that modulates one or more of the activities of 46798 protein activity associated with the cell. An agent that modulates 46798 protein activity can be an agent as described herein, such as a nucleic acid or a protein, a naturally-occurring target molecule of a 46798 protein (e.g., a 46798 substrate or receptor), a 46798 antibody, a 46798 agonist or antagonist, a peptidomimetic of a 46798 agonist or antagonist, or other small molecule.

In one embodiment, the agent stimulates one or 46798 activities. Examples of such stimulatory agents include active 46798 protein and a nucleic acid molecule encoding 46798. In another embodiment, the agent inhibits one or more 46798 activities. Examples of such inhibitory agents include antisense 46798 nucleic acid molecules, anti-46798 antibodies, and 46798 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 46798 protein or nucleic acid molecule. In one embodiment, the method involves administering an agent (e.g., an agent identified by a screening assay described herein), or combination of agents that modulates (e.g., up-regulates or down-regulates) 46798 expression or activity. In another embodiment, the method involves administering a 46798 protein or nucleic acid molecule as therapy to compensate for reduced, aberrant, or unwanted 46798 expression or activity.

Stimulation of 46798 activity is desirable in situations in which 46798 is abnormally down-regulated and/or in which increased 46798 activity is likely to have a beneficial effect. For example, stimulation of 46798 activity is desirable in situations in which a 46798 is down-regulated and/or in which increased 46798 activity is likely to have a beneficial effect. Likewise, inhibition of 46798 activity is desirable in situations in which 46798 is abnormally up-regulated and/or in which decreased 46798 activity is likely to have a beneficial effect.

Pharmacogenomics

The 46798 molecules of the present invention, as well as agents, or modulators which have a stimulatory or inhibitory effect on 46798 activity (e.g., 46798 gene expression) as identified by a screening assay described herein can be administered to individuals to treat (prophylactically or therapeutically) 46798-associated disorders associated with aberrant or unwanted 46798 activity (e.g., disorders associated with hematopoiesis and immune disorders). In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a 46798 molecule or 46798 modulator as well as tailoring the dosage and/or therapeutic regimen of treatment with a 46798 molecule or 46798 modulator.

Pharmacogenomics deals with clinically significant hereditary variations in the response to drugs due to altered drug disposition and abnormal action in affected persons (e.g., Eichelbaum et al., 1996, Clin. Exp. Pharmacol. Physiol. 23:983–985; Linder et al., 1997, Clin. Chem. 43:254–266). In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is hemolysis after ingestion of oxidant drugs (anti-malarials, sulfonamides, analgesics, nitrofurans) and consumption of fava beans.

One pharmacogenomics approach to identifying genes that predict drug response, known as "a genome-wide association," relies primarily on a high-resolution map of the human genome consisting of already known gene-related markers (e.g., a "bi-allelic" gene marker map which consists of 60,000–100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high-resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP can be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that can be common among such genetically similar individuals.

Alternatively, a method termed the "candidate gene approach" can be utilized to identify genes that predict drug response. According to this method, if a gene that encodes a drug's target is known (e.g., a 46798 protein of the present invention), all common variants of that gene can be fairly easily identified in the population and it can be determined if having one version of the gene versus another is associated with a particular drug response.

Alternatively, a method termed "gene expression profiling," can be utilized to identify genes that predict drug response. For example, the gene expression of an animal dosed with a drug (e.g., a 46798 molecule or 46798 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 46798 molecule or 46798 modulator, such as a modulator identified by one of the exemplary screening assays described herein.

The present invention further provides methods for identifying new agents, or combinations, that are based on identifying agents that modulate the activity of one or more of the gene products encoded by one or more of the 46798 genes of the present invention, wherein these products can be associated with resistance of the cells to a therapeutic agent. Specifically, the activity of the proteins encoded by the 46798 genes of the present invention can be used as a basis for identifying agents for overcoming agent resistance. By blocking the activity of one or more of the resistance proteins, target cells, e.g., hematopoietic cells, will become sensitive to treatment with an agent that the unmodified target cells were resistant to.

Monitoring the influence of agents (e.g., drugs) on the expression or activity of a 46798 protein can be applied in clinical trials. For example, the effectiveness of an agent determined by a screening assay as described herein to increase 46798 gene expression, protein levels, or up-regulate 46798 activity, can be monitored in clinical trials of subjects exhibiting decreased 46798 gene expression, protein levels, or down-regulated 46798 activity. Alternatively, the effectiveness of an agent determined by a screening assay to decrease 46798 gene expression, protein levels, or down-regulate 46798 activity, can be monitored in clinical trials of subjects exhibiting increased 46798 gene expression, protein levels, or up-regulated 46798 activity. In such clinical trials, the expression or activity of a 46798 gene, and preferably, other genes that have been implicated in, for example, a 46798-associated disorder can be used as a "read out" or markers of the phenotype of a particular cell.

Other Embodiments

In another aspect, the invention features, a method of analyzing a plurality of capture probes. The method can be used, e.g., to analyze gene expression. The method includes: providing a two-dimensional array having a plurality of addresses, each address of the plurality being positionally distinguishable from each other address of the plurality, and each address of the plurality having a unique capture probe, e.g., a nucleic acid or peptide sequence; contacting the array with a 46798, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 46798 nucleic acid, polypeptide, or antibody.

The capture probes can be a set of nucleic acids from a selected sample, e.g., a sample of nucleic acids derived from a control or non-stimulated tissue or cell.

The method can include contacting the 46798 nucleic acid, polypeptide, or antibody with a first array having a plurality of capture probes and a second array having a different plurality of capture probes. The results of hybridization can be compared, e.g., to analyze differences in expression between a first and second sample. The first plurality of capture probes can be from a control sample, e.g., a wild-type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 46798. Such methods can be used to diagnose a subject, e.g., to evaluate risk for a disease or disorder, to evaluate suitability of a selected treatment for a subject, to evaluate whether a subject has a disease or disorder. 46798 is associated with hematopoiesis, thus it is useful for evaluating disorders relating to hematopoiesis.

The method can be used to detect SNPs, as described above.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 46798 or from a cell or subject in which a 46798 mediated response has been elicited, e.g., by contact of the cell with 46798 nucleic acid or protein, or administration to the cell or subject 46798 nucleic acid or protein; contacting the array with one or more inquiry probe, wherein an inquiry probe can be a nucleic acid, polypeptide, or antibody (which is preferably other than 46798 nucleic acid, polypeptide, or antibody); providing a two-dimensional array having a plurality of addresses, each address of the plurality being positionally distinguishable from each other address of the plurality, and each address of the plurality having a unique capture probe, e.g., wherein the capture probes are from a cell or subject which does not express 46798 (or does not express as highly as in the case of the 46798 positive plurality of capture probes) or from a cell or subject which in which a 46798 mediated response has not been elicited (or has been elicited to a lesser extent than in the first sample); contacting the array with one or more inquiry probes (which is preferably other than a 46798 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or malexpress 46798 or from a cell or subject in which a 46798-mediated response has been elicited, e.g., by contact of the cell with 46798 nucleic acid or protein, or administration to the cell or subject 46798 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 46798 (or does not express as highly as in the case of the 46798 positive plurality of capture probes) or from a cell or subject which in which a 46798 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 46798, e.g., analyzing structure, function, or relatedness to other nucleic acid or amino acid sequences. The method includes: providing a 46798 nucleic acid or amino acid sequence, e.g., nucleotide sequence from 46798 or a portion thereof; comparing the 46798 sequence with one or more preferably a plurality of sequences from a collection of sequences, e.g., a nucleic acid or protein sequence database; to thereby analyze 46798.

The method can include evaluating the sequence identity between a 46798 sequence and a database sequence. The method can be performed by accessing the database at a second site, e.g., via the internet.

In another aspect, the invention features, a set of oligonucleotides, useful, e.g., for identifying SNPs, or identifying specific alleles of 46798. The set includes a plurality of oligonucleotides, each of which has a different nucleotide at an interrogation position, e.g., an SNP or the site of a mutation. In a preferred embodiment, the plurality of oligonucleotides are identical in sequence with one another (except for differences in length). The oligonucleotides can be provided with differential labels, such that an oligonucleotide that hybridizes to one allele provides a signal that is distinguishable from an oligonucleotide that hybridizes to a second allele.

The sequence of a 46798 molecules is provided in a variety of mediums to facilitate use thereof. A sequence can be provided as a manufacture, other than an isolated nucleic acid or amino acid molecule, which contains a 46798. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form.

A 46798 nucleotide or amino acid sequence can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect™ and Microsoft Word™, or represented in the form of an ASCII file, stored in a database application, such as DB2, Sybase™, Oracle™, or the like. The skilled artisan can readily adapt any number of data processor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention that match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, can be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 46798 sequence that includes recording the sequence on a computer readable matrix. In a preferred embodiment, the record includes one or more of the following: identification of an open reading frame; identification of a domain, region, or site; identification of the start of transcription; identification of the transcription terminator; the full length amino acid sequence of the protein, or a mature form thereof; the 5'- end of the translated region; or 5'- and/or 3'-regulatory regions.

In another aspect, the invention features a method of analyzing a sequence. The method includes: providing a 46798 sequence or record, in computer readable form; comparing a second sequence to the gene name sequence; thereby analyzing a sequence. Comparison can include comparing to sequences for sequence identity or determining if one sequence is included within the other, e.g., determining if the 46798 sequence includes a sequence being compared. In a preferred embodiment, the 46798 or second sequence is stored on a first computer, e.g., at a first site and the comparison is performed, read, or recorded on a second computer, e.g., at a second site. For example, the 46798 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5'-end of the translated region; or 5'- and/or 3'-regulatory regions.

This invention is further illustrated by the following examples that should not be construed as limiting. The contents of all references, patents and published patent applications cited throughout this application are incorporated herein by reference.

EXAMPLES

Example 1

Identification and Characterization of Human 46798 cDNA

The long form human 46798 nucleotide sequence (FIG. 1; SEQ ID NO: 1), which is approximately 2527 nucleotides in length including non-translated regions, contains a predicted methionine-initiated coding sequence at about nucleotide residues 300–1859. The coding sequence encodes a 520 amino acid protein (SEQ ID NO: 2). The short form human 46798 nucleotide sequence (FIG. 3; SEQ ID NO: 11), which is approximately 2310 nucleotides in length including non-translated regions, contains a predicted methionine-initiated coding sequence at about nucleotide residues 317–1652 The coding sequence encodes a 445 amino acid protein (SEQ ID NO: 12).

Example 2

Tissue Distribution of 46798 mRNA

Northern blot hybridizations with various RNA samples can be performed under standard conditions and washed under stringent conditions, i.e., 0.2× SSC at 65° C. A DNA probe corresponding to all or a portion of a 46798 cDNA (i.e., one of SEQ ID NOs: 1 and 11) can be used. The DNA can, for example, be radioactively labeled with 32P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb™ hybridization solution (Clontech) and washed at high stringency according to manufacturer's recommendations.

Example 3

Recombinant Expression of 46798 in Bacterial Cells

In this example, 46798 is expressed as a recombinant glutathione-S-transferase (GST) fusion polypeptide in *E. coli* and the fusion polypeptide is isolated and characterized. Specifically, 46798 nucleic acid sequences are fused to GST nucleic acid sequences and this fusion construct is expressed in *E. coli*, e.g., strain PEB199. Expression of the GST-46798 fusion construct in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 4

Expression of Recombinant 46798 Protein in COS Cells

To express the 46798 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 46798 protein and an HA tag (Wilson et al., 1984, Cell 37:767) or a FLAG tag fused in-frame to its 3'-end of the fragment is cloned into the polylinker region of the vector, thereby placing the expression of the recombinant protein under the control of the CMV promoter.

To construct the plasmid, the 46798 DNA sequence is amplified by PCR using two primers. The 5' primer contains the restriction site of interest followed by approximately twenty nucleotides of the 46798 coding sequence starting from the initiation codon; the 3'-end sequence contains complementary sequences to the other restriction site of interest, a translation stop codon, the HA tag or FLAG tag and the last 20 nucleotides of the 46798 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the 46798 gene is inserted in the desired orientation. The ligation mixture is transformed into *E. coli* cells (strains HB101, DH5alpha, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 46798-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook et al., (1989, Molecular Cloning: A Laboratory Manual. 2nd ed., Cold Spring Harbor Laboratory Press, Cold Spring Harbor, N.Y.). The expression of the 46798 polypeptide is detected by radiolabeling ($^{35}$S-methionine or $^{35}$S-cysteine, available from NEN, Boston, Mass., can be used) and immunoprecipitation (Harlow et al., 1988, Antibodies: A Laboratory Manual, Cold Spring Harbor Laboratory Press, Cold Spring Harbor, N.Y.) using an HA-specific monoclonal antibody. Briefly, the cells are labeled for 8 hours with $^{35}$S-methionine (or $^{35}$S-cysteine). The culture media are then collected and the cells are lysed using detergents (RIPA buffer, 150 millimolar NaCl, 1% NP-40, 0.1% SDS, 0.5% DOC, 50 millimolar Tris, pH 7.5). Both the cell lysate and the culture media are precipitated with an HA-specific monoclonal antibody. Precipitated polypeptides are then analyzed by SDS-PAGE. Alternatively, DNA containing the 46798 coding sequence is cloned directly into the polylinker of the pcDNA/Amp vector using the appropriate restriction sites. The resulting plasmid is transfected into COS cells in the manner described above, and the expression of the 46798 polypeptide is detected by radiolabeling and immunoprecipitation using a 46798-specific monoclonal antibody.

Example 5

Expression of the 46798 Gene

Tables 1–4 display the results of real time quantitative PCR (TAQMAN®) analysis of 46798 gene expression in a variety of cells and tissues.

TABLE 1

| Tissue Type | Relative Expression of the 46798 Gene |
|---|---|
| Normal Artery | 121 |
| Diseased Aorta | 21.4 |
| Normal Vein | 56.7 |
| Coronary Smooth Muscle Cells | 0.00 |
| Human Umbilical Vein Endothelial Cells | 105 |
| Hemangioma | 21.1 |
| Normal Heart | 5.35 |
| Heart Congestive Heart Failure | 10.1 |

TABLE 1-continued

| Tissue Type | Relative Expression of the 46798 Gene |
|---|---|
| Kidney | 38.1 |
| Skeletal Muscle | 20.4 |
| Normal Adipose | 37.0 |
| Pancreas | 27.4 |
| Primary Osteoblasts | 0.00 |
| Differentiated Osteoclasts | 0.00 |
| Normal Skin | 82.8 |
| Normal Spinal Cord | 19.2 |
| Normal Brain Cortex | 122 |
| Normal Brain Hypothalamus | 130 |
| Nerve | 137 |
| Dorsal Root Ganglion | 160 |
| Normal Breast | 38.5 |
| Breast Tumor | 1.26 |
| Normal Ovary | 25.2 |
| Ovary Tumor | 1.32 |
| Normal Prostate | 12.2 |
| Prostate Tumor | 14.8 |
| Salivary Glands | 2.39 |
| Normal Colon | 73.1 |
| Colon Tumor | 54.6 |
| Normal Lung | 34.6 |
| Lung Tumor | 35.4 |
| Lung Chronic Obstructive Pulmonary Disease | 84.5 |
| Colon Inflammatory Bowel Disease | 17.4 |
| Normal Liver | 0.00 |
| Liver Fibrosis | 3.09 |
| Normal Spleen | 0.43 |
| Normal Tonsil | 24.6 |
| Normal Lymph node | 7.57 |
| Normal Small Intestine | 17.8 |
| Macrophages | 0.00 |
| Synovium | 6.52 |
| Bone Marrow—Mononuclear Cells | 0.00 |
| Activated Peripheral Blood Mononuclear Cells | 0.00 |
| Neutrophils | 0.00 |
| Megakaryocytes | 0.00 |
| Erythroid | 0.00 |

TABLE 2

| Tissue Type | Relative Expression of the 46798 Gene |
|---|---|
| PIT 400 Normal Breast | 0.04 |
| PIT 372 Normal Breast | 0.41 |
| CHT 559 Normal Breast | 0.00 |
| CLN 168 Breast Tumor: IDC | 0.18 |
| MDA 304 Breast Tumor: MD-IDC | 0.06 |
| CHT 2002 Breast Tumor: IDC | 0.07 |
| CHT 562 Breast Tumor: IDC | 0.03 |
| NDR 138 Breast Tumor ILC (LG) | 0.46 |
| CHT 1841 Lymph Node (Breast Metastasis) | 0.00 |
| PIT 58 Lung (Breast Metastasis) | 0.55 |
| CHT 620 Normal Ovary | 0.21 |
| PIT 208 Normal Ovary | 0.04 |
| CLN 012 Ovary Tumor | 0.14 |
| CLN 07 Ovary Tumor | 0.00 |
| CLN 17 Ovary Tumor | 0.09 |
| MDA 25 Ovary Tumor | 0.50 |
| MDA 216 Ovary Tumor | 0.00 |
| PIT 298 Normal Lung | 1.77 |
| MDA 185 Normal Lung | 1.35 |
| CLN 930 Normal Lung | 1.29 |
| MPI 215 Lung Tumor-Small Cell | 0.31 |
| MDA 259 Lung Tumor-PDNSCCL | 0.12 |
| CHT 832 Lung Tumor-PDNSCCL | 8.09 |
| MDA 262 Lung Tumor-SCC | 0.67 |
| CHT 793 Lung Tumor-ACA | 0.30 |
| CHT 331 Lung Tumor-ACA | 3.73 |
| CHT 405 Normal Colon | 0.52 |
| CHT 523 Normal Colon | 3.79 |
| CHT 371 Normal Colon | 2.67 |

TABLE 2-continued

| Tissue Type | Relative Expression of the 46798 Gene |
|---|---|
| CHT 382 Colon Tumor: MD | 0.00 |
| CHT 528 Colon Tumor: MD | 2.07 |
| CLN 609 Colon Tumor | 0.59 |
| NDR 210 Colon Tumor: MD-PD | 0.67 |
| CHT 340 Colon-Liver Metastasis | 0.16 |
| NDR 100 Colon-Liver Metastasis | 2.06 |
| PIT 260 Normal Liver (Female) | 0.00 |
| CHT 1653 Cervix Squamous Cell Carcinoma | 69.1 |
| CHT 569 Cervix Squamous Cell Carcinoma | 2.64 |
| A24 HMVEC-Arr | 0.03 |
| C48 HMVEC-Prol | 0.00 |
| Pooled Hemangiomas | 0.13 |
| HCT116N22 Normoxic | 0.00 |
| HCT116H22 Hypoxic | 0.00 |

TABLE 3

| Tissue Type | Relative Expression of the 46798 Gene |
|---|---|
| CHT 410 Normal Colon | 2.17 |
| CHT 425 Normal Colon | 1.87 |
| CHT 371 Normal Colon | 0.63 |
| PIT 281 Normal Colon | 5.74 |
| NDR 211 Normal Colon | 0.73 |
| CHT 122 Adenomas | 2.02 |
| CHT 887 Adenomas | 3.21 |
| CHT 414 Colonic ACA-B | 0.73 |
| CHT 841 Colonic ACA-B | 0.03 |
| CHT 890 Colonic ACA-B | 0.22 |
| CHT 910 Colonic ACA-B | 0.00 |
| CHT 377 Colonic ACA-B | 0.03 |
| CHT 520 Colonic ACA-C | 0.57 |
| CHT 596 Colonic ACA-C | 0.00 |
| CHT 907 Colonic ACA-C | 0.62 |
| CHT 372 Colonic ACA-C | 1.70 |
| NDR 210 Colonic ACA-C | 0.26 |
| CHT 1365 Colonic ACA-C | 0.39 |
| CLN 740 Normal Liver | 0.00 |
| CLN 741 Normal Liver | 0.00 |
| NDR 165 Normal Liver | 0.00 |
| NDR 150 Normal Liver | 0.00 |
| PIT 236 Normal Liver | 0.00 |
| CHT 1878 Normal Liver | 0.00 |
| CHT 119 Colon Liver Metastasis | 4.91 |
| CHT 131 Colon Liver Metastasis | 0.31 |
| CHT 218 Colon Liver Metastasis | 0.40 |
| CHT 739 Colon Liver Metastasis | 0.28 |
| CHT 755 Colon Liver Metastasis | 0.24 |

TABLE 3-continued

| Tissue Type | Relative Expression of the 46798 Gene |
|---|---|
| CHT 215 Colon Abdominal Metastasis | 0.22 |
| PIT 337 Normal Colon | 2.41 |
| CHT 807 Colonic ACA-B | 5.05 |
| CHT 382 Colonic ACA-B | 0.48 |
| CHT 077 Colon Liver Metastasis | 35.28 |

TABLE 4

| Tissue Type | Relative Expression of the 46798 Gene |
|---|---|
| CHT 371 Normal Colon | 2.40 |
| CHT 523 Normal Colon | 4.13 |
| NDR 104 Normal Colon | 8.85 |
| CHT 520 Colonic ACA-C | 1.33 |
| CHT 1365 Colonic ACA-C | 0.84 |
| CHT 382 Colonic ACA-B | 0.00 |
| CHT 122 Adenocarcinoma | 3.17 |
| CHT 077 Liver-Colon Metastasis | 0.08 |
| CHT 739 Liver-Colon Metastasis | 0.15 |
| CHT 755 Liver-Colon Metastasis | 0.46 |
| CHT001 Liver-Colon Metastasis | 0.14 |
| CHT 084 Liver-Colon Metastasis | 0.52 |
| CHT 113 Liver-Colon Metastasis | 0.10 |
| CHT 114 Liver-Colon Metastasis | 0.71 |
| CHT 127 Liver-Colon Metastasis | 1.09 |
| CHT 137 Liver-Colon Metastasis | 0.00 |
| CHT 218 Liver-Colon Metastasis | 0.44 |
| CHT 220 Liver-Colon Metastasis | 0.21 |
| CHT 324 Liver-Colon Metastasis | 0.25 |
| CHT 340 Liver-Colon Metastasis | 0.56 |
| CHT 530 Liver-Colon Metastasis | 1.57 |
| CHT 849 Liver-Colon Metastasis | 0.90 |
| CHT 1637 Liver-Colon Metastasis | 0.47 |
| CHT131 Liver-Colon Metastasis | 0.73 |
| NDR 165 Normal Liver | 0.00 |
| NDR 150 Normal Liver | 0.00 |
| PIT 236 Normal Liver | 0.00 |

Equivalents

Those skilled in the art will recognize, or be able to ascertain using no more than routine experimentation, many equivalents to the specific embodiments of the invention described herein. Such equivalents are intended to be encompassed by the following claims.

SEQUENCE LISTING

<160> NUMBER OF SEQ ID NOS: 24

<210> SEQ ID NO 1
<211> LENGTH: 2527
<212> TYPE: DNA
<213> ORGANISM: Homo sapiens

<400> SEQUENCE: 1

```
gccgggcctc cgcccctcc gcctgccttt ccttcctccc tccctcggtc cccggggccg        60
gcggacccgc gggcaggcac tgcccgggct ggacgacgtc tggccggctc ccggcgaagg       120
gcagcggagg agcggcccag agcgcgcagc tagggcactg gcgaaacccc gggacagtcc       180
```

-continued

| | |
|---|---|
| ctctccgtgc gggggcggcg cagagcagtc ccatccccgg ggtcccgggc gcggctgact | 240 |
| gccggctggt tccctgcgcg cagtagctcc ccgagccggg ctgcaccgga ggcggcgaga | 300 |
| tggtcgcgcg cgtcggcctc ctgctgcgcg ccctgcagct gctactgtgg ggccacctgg | 360 |
| acgcccagcc cgcggagcgc ggaggccagg agctgcgcaa ggaggcggag gcattcctag | 420 |
| agaagtacga atacctcaat gaacaggtcc ccaaagctcc cacctccact cgattcagcg | 480 |
| atgccatcag agcgtttcag tgggtgtccc agctacctgt cagcggcgtg ttggaccgcg | 540 |
| ccaccctgcg ccagatgact cgtccccgct gcggggttac agataccaac agttatgcgg | 600 |
| cctgggctga gaggatcagt gacttgtttg ctagacaccg gaccaaaatg aggcgtaaga | 660 |
| aacgctttgc aaagcaaggt aacaaatggt acaagcagca cctctcctac cgcctggtga | 720 |
| actggcctga gcatctgccg gagccggcag ttcggggcgc cgtgcgcgcc gccttccagt | 780 |
| tgtggagcaa cgtctcagcg ctggagttct gggaggcccc agccacaggc cccgctgaca | 840 |
| tccggctcac cttcttccaa ggggaccaca acgatgggct gggcaatgcc tttgatggcc | 900 |
| caggggcgc cctggcgcac gccttcctgc cccgccgcgg cgaagcgcac ttcgaccaag | 960 |
| atgagcgctg gtccctgagc cgccgccgcg ggcgcaacct gttcgtggtg ctggcgcacg | 1020 |
| agatcggtca cacgcttggc ctcacccact cgcccgcgcc gcgcgcgctc atggcgccct | 1080 |
| actacaagag gctgggccgc gacgcgctgc tcagctggga cgacgtgctg gccgtgcaga | 1140 |
| gcctgtatgg gaagccccta gggggctcag tggccgtcca gctcccagga aagctgttca | 1200 |
| ctgactttga gacctgggac tcctacagcc cccaaggaag gcgccctgaa acgcagggcc | 1260 |
| ctaaatactg ccactcttcc ttcgatgcca tcactgtaga caggcaacag caactgtaca | 1320 |
| tttttaaagg gagccatttc tgggaggtgg cagctgatgg caacgtctca gagccccgtc | 1380 |
| cactgcagga agatgggtc gggctgcccc ccaacattga ggctgcggca gtgtcattga | 1440 |
| atgatggaga tttctacttc ttcaaagggg gtcgatgctg gaggttccgg ggccccaagc | 1500 |
| cagtgtgggg tctcccacag ctgtgccggg caggggcct gccccgccat cctgacgccg | 1560 |
| ccctcttctt ccctcctctg cgccgcctca tcctcttcaa gggtgcccgc tactacgtgc | 1620 |
| tggcccgagg gggactgcaa gtggagccct actacccccg aagtctgcag gactggggag | 1680 |
| gcatccctga ggaggtcagc ggcgccctgc cgaggcccga tggctccatc atcttcttcc | 1740 |
| gagatgaccg ctactggcgc ctcgaccagg ccaaactgca ggcaaccacc tcgggccgct | 1800 |
| gggcaccga gctgccctgg atgggctgct ggcatgccaa ctcggggagc gccctgttct | 1860 |
| gaaggcacct cctcacctca gaaactggtg gtgctctcag ggcaaaatca tgttccccac | 1920 |
| ccccggggca gaaccctct tagaagcctc tgagtccctc tgcagaagac cgggcagcaa | 1980 |
| agcctccatc tggaagtctg tctgcctttg ttccttgaag aatgcagcat tgtctttgtc | 2040 |
| tgtccccacc acatggaggt gggggtggga tcaatcttag gaaaagcaaa aaagggtccc | 2100 |
| agatcccttg gcctttcct ccgaggactt ctatcctccc caggcctttg ttttttcggc | 2160 |
| taaaggtaca gttcctttca agaggtaaca gcactgggat ccaagcaggg ggatgaaaaa | 2220 |
| ctcagcagag aaattcgaga ccattttgca agactgtgcc cttctcctca ggaccccctg | 2280 |
| gctcagttct tgaaaaacgg tgtcatattt agtcagaggc cccaccccca ggaagcatgg | 2340 |
| atgggatgaa aggcacaggc gtctccaacc tcaaggccc tttgtggggt caggacacag | 2400 |
| agtgggaggg agactgatgc aggcctacca gtccctggct ttttgtctgg ggctggaata | 2460 |
| aagaggtgcc ttcagctggt gggccgagag gcaggaagca gccttccttg gaaaaaaaaa | 2520 |
| aaaaaaa | 2527 |

<210> SEQ ID NO 2
<211> LENGTH: 520
<212> TYPE: PRT
<213> ORGANISM: Homo sapiens

<400> SEQUENCE: 2

```
Met Val Ala Arg Val Gly Leu Leu Arg Ala Leu Gln Leu Leu
1               5                   10                  15

Trp Gly His Leu Asp Ala Gln Pro Ala Glu Arg Gly Gly Gln Glu Leu
            20                  25                  30

Arg Lys Glu Ala Glu Ala Phe Leu Glu Lys Tyr Gly Tyr Leu Asn Glu
                35                  40                  45

Gln Val Pro Lys Ala Pro Thr Ser Thr Arg Phe Ser Asp Ala Ile Arg
    50                  55                  60

Ala Phe Gln Trp Val Ser Gln Leu Pro Val Ser Gly Val Leu Asp Arg
65                  70                  75                  80

Ala Thr Leu Arg Gln Met Thr Arg Pro Arg Cys Gly Val Thr Asp Thr
                85                  90                  95

Asn Ser Tyr Ala Ala Trp Ala Glu Arg Ile Ser Asp Leu Phe Ala Arg
                100                 105                 110

His Arg Thr Lys Met Arg Arg Lys Lys Arg Phe Ala Lys Gln Gly Asn
            115                 120                 125

Lys Trp Tyr Lys Gln His Leu Ser Tyr Arg Leu Val Asn Trp Pro Glu
130                 135                 140

His Leu Pro Glu Pro Ala Val Arg Gly Ala Val Arg Ala Ala Phe Gln
145                 150                 155                 160

Leu Trp Ser Asn Val Ser Ala Leu Glu Phe Trp Glu Ala Pro Ala Thr
                165                 170                 175

Gly Pro Ala Asp Ile Arg Leu Thr Phe Phe Gln Gly Asp His Asn Asp
            180                 185                 190

Gly Leu Gly Asn Ala Phe Asp Gly Pro Gly Gly Ala Leu Ala His Ala
        195                 200                 205

Phe Leu Pro Arg Arg Gly Glu Ala His Phe Asp Gln Asp Glu Arg Trp
210                 215                 220

Ser Leu Ser Arg Arg Gly Arg Asn Leu Phe Val Val Leu Ala His
225                 230                 235                 240

Glu Ile Gly His Thr Leu Gly Leu Thr His Ser Pro Ala Pro Arg Ala
                245                 250                 255

Leu Met Ala Pro Tyr Tyr Lys Arg Leu Gly Arg Asp Ala Leu Leu Ser
            260                 265                 270

Trp Asp Asp Val Leu Ala Val Gln Ser Leu Tyr Gly Lys Pro Leu Gly
        275                 280                 285

Gly Ser Val Ala Val Gln Leu Pro Gly Lys Leu Phe Thr Asp Phe Glu
    290                 295                 300

Thr Trp Asp Ser Tyr Ser Pro Gln Gly Arg Arg Pro Glu Thr Gln Gly
305                 310                 315                 320

Pro Lys Tyr Cys His Ser Ser Phe Asp Ala Ile Thr Val Asp Arg Gln
                325                 330                 335

Gln Gln Leu Tyr Ile Phe Lys Gly Ser His Phe Trp Glu Val Ala Ala
            340                 345                 350

Asp Gly Asn Val Ser Glu Pro Arg Pro Leu Gln Glu Arg Trp Val Gly
        355                 360                 365

Leu Pro Pro Asn Ile Glu Ala Ala Ala Val Ser Leu Asn Asp Gly Asp
```

```
                370             375             380
Phe Tyr Phe Phe Lys Gly Gly Arg Cys Trp Arg Phe Arg Gly Pro Lys
385                 390                 395                 400

Pro Val Trp Gly Leu Pro Gln Leu Cys Arg Ala Gly Gly Leu Pro Arg
                405                 410                 415

His Pro Asp Ala Ala Leu Phe Phe Pro Pro Leu Arg Arg Leu Ile Leu
                420                 425                 430

Phe Lys Gly Ala Arg Tyr Tyr Val Leu Ala Arg Gly Gly Leu Gln Val
                435                 440                 445

Glu Pro Tyr Tyr Pro Arg Ser Leu Gln Asp Trp Gly Gly Ile Pro Glu
450                 455                 460

Glu Val Ser Gly Ala Leu Pro Arg Pro Asp Gly Ser Ile Ile Phe Phe
465                 470                 475                 480

Arg Asp Asp Arg Tyr Trp Arg Leu Asp Gln Ala Lys Leu Gln Ala Thr
                485                 490                 495

Thr Ser Gly Arg Trp Ala Thr Glu Leu Pro Trp Met Gly Cys Trp His
                500                 505                 510

Ala Asn Ser Gly Ser Ala Leu Phe
                515                 520

<210> SEQ ID NO 3
<211> LENGTH: 1560
<212> TYPE: DNA
<213> ORGANISM: Homo sapiens

<400> SEQUENCE: 3
atggtcgcgc gcgtcggcct cctgctgcgc gccctgcagc tgctactgtg gggccacctg      60
gacgcccagc ccgcggagcg cggaggccag gagctgcgca aggaggcgga ggcattccta     120
gagaagtacg ataccctcaa tgaacaggtc cccaaagctc ccacctccac tcgattcagc     180
gatgccatca gagcgtttca gtgggtgtcc cagctacctg tcagcggcgt gttggaccgc     240
gccaccctgc gccagatgac tcgtccccgc tgcggggtta cagataccaa cagttatgcg     300
gcctgggctg agaggatcag tgacttgttt gctagacacc ggaccaaaat gaggcgtaag     360
aaacgctttg caaagcaagg taacaaatgg tacaagcagc acctctccta ccgcctggtg     420
aactggcctg agcatctgcc ggagccggca gttcggggcg ccgtgcgcgc cgccttccag     480
ttgtggagca acgtctcagc gctggagttc tgggaggccc cagccacagg ccccgctgac     540
atccggctca ccttcttcca aggggaccac aacgatgggc tgggcaatgc ctttgatggc     600 ccaggggggcg ccctggcgca cgccttcctg ccccgccgcg gcgaagcgca cttcgaccaa     660
gatgagcgct ggtccctgag ccgccgccgc gggcgcaacc tgttcgtggt gctggcgcac     720
gagatcggtc acacgcttgg cctcacccac tcgcccgcgc gcgcgcgcgct catggcgccc     780 tactacaaga ggctgggccg cgacgcgctg ctcagctggg acgacgtgct ggccgtgcag     840
agcctgtatg ggaagcccct aggggctca gtggccgtcc agctcccagg aaagctgttc     900
actgactttg agacctggga ctcctacagc cccaaggaa gcgccctga acgcagggc     960 cctaaatact gccactcttc cttcgatgcc atcactgtag acaggcaaca gcaactgtac    1020
atttttaaag ggagccattt ctggaggtg cagctgatg caacgtctc agagcccgt       1080 ccactgcagg aaagatgggt cgggctgccc ccaacattg aggctgcggc agtgtcattg    1140
aatgatggag atttctactt cttcaaaggg ggtcgatgct ggaggttccg gggccccaag    1200
ccagtgtggg gtctcccaca gctgtgccgg gcaggggggcc tgccccgcca tcctgacgcc    1260
```

-continued

```
gccctcttct tccctcctct gcgccgcctc atcctcttca agggtgcccg ctactacgtg    1320
ctggcccgag ggggactgca agtggagccc tactaccccc gaagtctgca ggactgggga    1380
ggcatccctg aggaggtcag cggcgccctg ccgaggcccg atggctccat catcttcttc    1440
cgagatgacc gctactggcg cctcgaccag gccaaactgc aggcaaccac ctcgggccgc    1500
tgggccaccg agctgccctg gatgggctgc tggcatgcca actcggggag cgccctgttc    1560
```

```
<210> SEQ ID NO 4
<211> LENGTH:
<212> TYPE:
<213> ORGANISM:

<400> SEQUENCE: 4

000

<210> SEQ ID NO 5
<211> LENGTH:
<212> TYPE:
<213> ORGANISM:

<400> SEQUENCE: 5

000

<210> SEQ ID NO 6
<211> LENGTH:
<212> TYPE:
<213> ORGANISM:

<400> SEQUENCE: 6

000

<210> SEQ ID NO 7
<211> LENGTH:
<212> TYPE:
<213> ORGANISM:

<400> SEQUENCE: 7

000

<210> SEQ ID NO 8
<211> LENGTH:
<212> TYPE:
<213> ORGANISM:

<400> SEQUENCE: 8

000

<210> SEQ ID NO 9
<211> LENGTH:
<212> TYPE:
<213> ORGANISM:

<400> SEQUENCE: 9

000

<210> SEQ ID NO 10
<211> LENGTH:
<212> TYPE:
<213> ORGANISM:

<400> SEQUENCE: 10

000
```

<210> SEQ ID NO 11
<211> LENGTH: 2310
<212> TYPE: DNA
<213> ORGANISM: Homo sapiens

<400> SEQUENCE: 11

```
gtcgacccac gcgtccggcc gggcctccgc cccctccgcc tgcctttcct tcctccctcc      60
ctcggtcccc ggggccggcg gacccgcggg caggcactgc ccgggctgga cgacgtctgg     120
ccggctcccg gcgaagggca gcggaggagc ggcccagagc gcgcagctag ggcactggcg     180
aaaccccggg acagtccctc tccgtgcggg ggcggcgcag agcagtccca tccccggggt     240
cccgggcgcg gctgactgcc ggctggttcc ctgcgcgcag tagctccccg agccgggctg     300
caccggaggc ggcgagatgg tcgcgcgcgt cggcctcctg ctgcgcgccc tgcagctgct     360
actgtggggc cacctggacg cccagcccgc ggagcgcgga ggccaggagc tgcgcaagga     420
ggcggaggca ttcctagaga agtacggata cctcaatgaa caggtcccca agctcccac     480
ctccactcga ttcagcgatg ccatcagagc gtttcagtgg gtgtcccagc tacctgtcag     540
cggcgtgttg gaccgcgcca ccctgcgcca gatgactcgt cccgctgcg ggttacaga     600
taccaacagt tatgcggcct gggctgagag gatcagtgac ttgtttgcta gacaccggac     660
caaaatgagg cgtaagaaac gctttgcaaa gcaaggggc gccctggcgc acgccttcct     720
gccccgccgc ggcgaagcgc acttcgacca agatgagcgc tggtccctga gccgccgccg     780
cgggcgcaac ctgttcgtgg tgctggcgca cgagatcggt cacacgcttg gcctcaccca     840
ctcgcccgcg ccgcgcgcgc tcatggcgcc ctactacaag aggctgggcc gcgacgcgct     900
gctcagctgg gacgacgtgc tggccgtgca gagcctgtat gggaagcccc tagggggctc     960
agtggccgtc cagctcccag gaaagctgtt cactgacttt gagacctggg actcctacag    1020
cccccaagga aggcgccctg aaacgcaggg ccctaaatac tgccactctt ccttcgatgc    1080
catcactgta gacaggcaac agcaactgta catttttaaa gggagccatt ctgggaggt    1140
ggcagctgat ggcaacgtct cagagccccg tccactgcag gaaagatggg tcgggctgcc    1200
ccccaacatt gaggctgcgg cagtgtcatt gaatgatgga gatttctact tcttcaaagg    1260
gggtcgatgc tggaggttcc ggggcccca gccagtgtgg ggtctcccac agctgtgccg    1320
ggcaggggc ctgccccgcc atcctgacgc cgccctcttc ttccctcctc tgcgccgcct    1380
catcctcttc aagggtgccc gctactacgt gctggcccga ggggactgc aagtggagcc    1440
ctactacccc cgaagtctgc aggactgggg aggcatccct gaggaggtca gcggcgccct    1500
gccgaggccc gatggctcca tcatcttctt ccgagatgac cgctactggc gcctcgacca    1560
ggccaaactg caggcaacca cctcgggccg ctgggccacc gagctgccct ggatgggctg    1620
ctggcatgcc aactcgggga gcgccctgtt ctgaaggcac ctcctcacct cagaaactgg    1680
tggtgctctc agggcaaaat catgttcccc accccgggg cagaacccct cttagaagcc    1740
tctgagtccc tctgcagaag accgggcagc aaagcctcca tctggaagtc tgtctgcctt    1800
tgttccttga agaatgcagc attgtctttg tctgtcccca ccacatggag gtgggggtgg    1860
gatcaatctt aggaaaagca aaaagggtc ccagatcccc tggccctttc ctccgaggac    1920
ttctatcctc cccaggcctt tgtttcttcg gctaaaggta cagttccttt caagaggtaa    1980
cagcactggg atccaagcag ggggatgaaa aactcagcag agaaattcga gaccattttg    2040
caagactgtg cccttctcct caggaccccc tggctcagtt cttgaaaaac ggtgtcatat    2100
```

-continued

```
ttagtcagag gccccacccc caggaagcat ggatggggat gaaggcacag gcgtctccaa    2160
cctcagaggc cctttgtggg gtcaggacac agagtgggag ggagactgat gcaggcctac    2220
cagtccctgg cttttgtct ggggctggaa taaagaggtg ccttcagctg gtgggccgag     2280
aaaaaaaaaa aaaaaaaaa gggcggccgc                                      2310
```

<210> SEQ ID NO 12
<211> LENGTH: 445
<212> TYPE: PRT
<213> ORGANISM: Homo sapiens

<400> SEQUENCE: 12

```
Met Val Ala Arg Val Gly Leu Leu Arg Ala Leu Gln Leu Leu
1               5                   10                  15

Trp Gly His Leu Asp Ala Gln Pro Ala Glu Arg Gly Gly Gln Glu Leu
                20                  25                  30

Arg Lys Glu Ala Glu Ala Phe Leu Glu Lys Tyr Gly Tyr Leu Asn Glu
            35                  40                  45

Gln Val Pro Lys Ala Pro Thr Ser Thr Arg Phe Ser Asp Ala Ile Arg
        50                  55                  60

Ala Phe Gln Trp Val Ser Gln Leu Pro Val Ser Gly Val Leu Asp Arg
65                  70                  75                  80

Ala Thr Leu Arg Gln Met Thr Arg Pro Arg Cys Gly Val Thr Asp Thr
                85                  90                  95

Asn Ser Tyr Ala Ala Trp Ala Glu Arg Ile Ser Asp Leu Phe Ala Arg
            100                 105                 110

His Arg Thr Lys Met Arg Arg Lys Arg Phe Ala Lys Gln Gly Gly
        115                 120                 125

Ala Leu Ala His Ala Phe Leu Pro Arg Arg Gly Glu Ala His Phe Asp
130                 135                 140

Gln Asp Glu Arg Trp Ser Leu Ser Arg Arg Gly Arg Asn Leu Phe
145                 150                 155                 160

Val Val Leu Ala His Glu Ile Gly His Thr Leu Gly Leu Thr His Ser
                165                 170                 175

Pro Ala Pro Arg Ala Leu Met Ala Pro Tyr Tyr Lys Arg Leu Gly Arg
            180                 185                 190

Asp Ala Leu Leu Ser Trp Asp Val Leu Ala Val Gln Ser Leu Tyr
        195                 200                 205

Gly Lys Pro Leu Gly Gly Ser Val Ala Val Gln Leu Pro Gly Lys Leu
        210                 215                 220

Phe Thr Asp Phe Glu Thr Trp Asp Ser Tyr Ser Pro Gln Gly Arg Arg
225                 230                 235                 240

Pro Glu Thr Gln Gly Pro Lys Tyr Cys His Ser Ser Phe Asp Ala Ile
                245                 250                 255

Thr Val Asp Arg Gln Gln Leu Tyr Ile Phe Lys Gly Ser His Phe
            260                 265                 270

Trp Glu Val Ala Ala Asp Gly Asn Val Ser Glu Pro Arg Pro Leu Gln
        275                 280                 285

Glu Arg Trp Val Gly Leu Pro Pro Asn Ile Glu Ala Ala Val Ser
        290                 295                 300

Leu Asn Asp Gly Asp Phe Tyr Phe Lys Gly Gly Arg Cys Trp Arg
305                 310                 315                 320

Phe Arg Gly Pro Lys Pro Val Trp Gly Leu Pro Gln Leu Cys Arg Ala
                325                 330                 335
```

-continued

```
Gly Gly Leu Pro Arg His Pro Asp Ala Ala Leu Phe Phe Pro Pro Leu
            340                 345                 350

Arg Arg Leu Ile Leu Phe Lys Gly Ala Arg Tyr Tyr Val Leu Ala Arg
            355                 360                 365

Gly Gly Leu Gln Val Glu Pro Tyr Tyr Pro Arg Ser Leu Gln Asp Trp
            370                 375                 380

Gly Gly Ile Pro Glu Glu Val Ser Gly Ala Leu Pro Arg Pro Asp Gly
385                 390                 395                 400

Ser Ile Ile Phe Phe Arg Asp Asp Arg Tyr Trp Arg Leu Asp Gln Ala
                405                 410                 415

Lys Leu Gln Ala Thr Thr Ser Gly Arg Trp Ala Thr Glu Leu Pro Trp
            420                 425                 430

Met Gly Cys Trp His Ala Asn Ser Gly Ser Ala Leu Phe
            435                 440                 445

<210> SEQ ID NO 13
<211> LENGTH: 1335
<212> TYPE: DNA
<213> ORGANISM: Homo sapiens

<400> SEQUENCE: 13
atggtcgcgc gcgtcggcct cctgctgcgc gccctgcagc tgctactgtg gggccacctg      60
gacgcccagc ccgcggagcg cggaggccag gagctgcgca aggaggcgga ggcattccta     120
gagaagtacg gatacctcaa tgaacaggtc cccaaagctc ccacctccac tcgattcagc     180
gatgccatca gagcgtttca gtgggtgtcc cagctacctg tcagcggcgt gttggaccgc     240 gccacccctgc gccagatgac tcgtccccgc tgcggggtta cagataccaa cagttatgcg     300
gcctgggctg agaggatcag tgacttgttt gctagacacc ggaccaaaat gaggcgtaag     360
aaacgctttg caaagcaagg gggcgccctg gcgcacgcct tcctgccccg ccgcggcgaa     420
gcgcacttcg accaagatga gcgctggtcc ctgagccgcc gccgcgggcg caacctgttc     480
gtggtgctgg cgcacgagat cggtcacacg cttggcctca cccactcgcc cgcgccgcgc     540
gcgctcatgg cgccctacta caagaggctg gccgcgacg cgctgctcag ctgggacgac     600
gtgctggccg tgcagagcct gtatgggaag cccctagggg gctcagtggc cgtccagctc     660
ccaggaaagc tgttcactga ctttgagacc tgggactcct acagccccca aggaaggcgc     720
cctgaaacgc agggccctaa atactgccac tcttccttcg atgccatcac tgtagacagg     780
caacagcaac tgtacatttt taaagggagc catttctggg aggtggcagc tgatggcaac     840
gtctcagagc cccgtccact gcaggaaaga tgggtcgggc tgccccccaa cattgaggct     900
gcggcagtgt cattgaatga tggagatttc tacttcttca aaggggtcg atgctggagg     960 ttccggggcc ccaagccagt gtgggtctc ccacagctgt gccgggcagg gggcctgccc    1020
cgccatcctg acgccgccct cttcttccct cctctgcgcc gctcatcct cttcaagggt    1080 gcccgctact acgtgctggc ccgaggggga ctgcaagtgg agccctacta cccccgaagt    1140
ctgcaggact ggggaggcat ccctgaggag gtcagcggcg ccctgccgag gcccgatggc    1200
tccatcatct tcttccgaga tgaccgctac tggcgcctcg accaggccaa actgcaggca    1260
accacctcgg gccgctgggc caccgagctg ccctggatgg gctgctggca tgccaactcg    1320
gggagcgccc tgttc                                                     1335

<210> SEQ ID NO 14
<211> LENGTH:
<212> TYPE:
```

```
<213> ORGANISM:

<400> SEQUENCE: 14

000

<210> SEQ ID NO 15
<211> LENGTH:
<212> TYPE:
<213> ORGANISM:

<400> SEQUENCE: 15

000

<210> SEQ ID NO 16
<211> LENGTH:
<212> TYPE:
<213> ORGANISM:

<400> SEQUENCE: 16

000

<210> SEQ ID NO 17
<211> LENGTH:
<212> TYPE:
<213> ORGANISM:

<400> SEQUENCE: 17

000

<210> SEQ ID NO 18
<211> LENGTH:
<212> TYPE:
<213> ORGANISM:

<400> SEQUENCE: 18

000

<210> SEQ ID NO 19
<211> LENGTH:
<212> TYPE:
<213> ORGANISM:

<400> SEQUENCE: 19

000

<210> SEQ ID NO 20
<211> LENGTH:
<212> TYPE:
<213> ORGANISM:

<400> SEQUENCE: 20

000

<210> SEQ ID NO 21
<211> LENGTH: 520
<212> TYPE: PRT
<213> ORGANISM: Homo sapiens

<400> SEQUENCE: 21

Met Val Ala Arg Val Gly Leu Leu Arg Ala Leu Gln Leu Leu
1               5                   10                  15

Trp Gly His Leu Asp Ala Gln Pro Ala Glu Arg Gly Gly Gln Glu Leu
                20                  25                  30
```

```
Arg Lys Glu Ala Glu Ala Phe Leu Glu Lys Tyr Gly Tyr Leu Asn Glu
         35                  40                  45

Gln Val Pro Lys Ala Pro Thr Ser Thr Arg Phe Ser Asp Ala Ile Arg
     50                  55                  60

Ala Phe Gln Trp Val Ser Gln Leu Pro Val Ser Gly Val Leu Asp Arg
65                  70                  75                  80

Ala Thr Leu Arg Gln Met Thr Arg Pro Arg Cys Gly Val Thr Asp Thr
                 85                  90                  95

Asn Ser Tyr Ala Ala Trp Ala Glu Arg Ile Ser Asp Leu Phe Ala Arg
             100                 105                 110

His Arg Thr Lys Met Arg Arg Lys Lys Arg Phe Ala Lys Gln Gly Asn
             115                 120                 125

Lys Trp Tyr Lys Gln His Leu Ser Tyr Arg Leu Val Asn Trp Pro Glu
         130                 135                 140

His Leu Pro Glu Pro Ala Val Arg Gly Ala Val Arg Ala Ala Phe Gln
145                 150                 155                 160

Leu Trp Ser Asn Val Ser Ala Leu Glu Phe Trp Glu Ala Pro Ala Thr
                 165                 170                 175

Gly Pro Ala Asp Ile Arg Leu Thr Phe Phe Gln Gly Asp His Asn Asp
             180                 185                 190

Gly Leu Gly Asn Ala Phe Asp Gly Pro Gly Gly Ala Leu Ala His Ala
         195                 200                 205

Phe Leu Pro Arg Arg Gly Glu Ala His Phe Asp Gln Asp Glu Arg Trp
         210                 215                 220

Ser Leu Ser Arg Arg Gly Arg Asn Leu Phe Val Val Leu Ala His
225                 230                 235                 240

Glu Ile Gly His Thr Leu Gly Leu Thr His Ser Pro Ala Pro Arg Ala
                 245                 250                 255

Leu Met Ala Pro Tyr Tyr Lys Arg Leu Gly Arg Asp Ala Leu Leu Ser
             260                 265                 270

Trp Asp Asp Val Leu Ala Val Gln Ser Leu Tyr Gly Lys Pro Leu Gly
         275                 280                 285

Gly Ser Val Ala Val Gln Leu Pro Gly Lys Leu Phe Thr Asp Phe Glu
     290                 295                 300

Thr Trp Asp Ser Tyr Ser Pro Gln Gly Arg Arg Pro Glu Thr Gln Gly
305                 310                 315                 320

Pro Lys Tyr Cys His Ser Ser Phe Asp Ala Ile Thr Val Asp Arg Gln
                 325                 330                 335

Gln Gln Leu Tyr Ile Phe Lys Gly Ser His Phe Trp Glu Val Ala Ala
             340                 345                 350

Asp Gly Asn Val Ser Glu Pro Arg Pro Leu Gln Glu Arg Trp Val Gly
         355                 360                 365

Leu Pro Pro Asn Ile Glu Ala Ala Val Ser Leu Asn Asp Gly Asp
     370                 375                 380

Phe Tyr Phe Phe Lys Gly Gly Arg Cys Trp Arg Phe Arg Gly Pro Lys
385                 390                 395                 400

Pro Val Trp Gly Leu Pro Gln Leu Cys Arg Ala Gly Gly Leu Pro Arg
                 405                 410                 415

His Pro Asp Ala Ala Leu Phe Phe Pro Pro Leu Arg Arg Leu Ile Leu
             420                 425                 430

Phe Lys Gly Ala Arg Tyr Tyr Val Leu Ala Arg Gly Gly Leu Gln Val
         435                 440                 445
```

```
Glu Pro Tyr Tyr Pro Arg Ser Leu Gln Asp Trp Gly Ile Pro Glu
            450                 455                 460
Glu Val Ser Gly Ala Leu Pro Arg Pro Asp Gly Ser Ile Ile Phe Phe
465                 470                 475                 480
Arg Asp Asp Arg Tyr Trp Arg Leu Asp Gln Ala Lys Leu Gln Ala Thr
                    485                 490                 495
Thr Ser Gly Arg Trp Ala Thr Glu Leu Pro Trp Met Gly Cys Trp His
            500                 505                 510
Ala Asn Ser Gly Ser Ala Leu Phe
            515                 520

<210> SEQ ID NO 22
<211> LENGTH: 393
<212> TYPE: PRT
<213> ORGANISM: Homo sapiens

<400> SEQUENCE: 22

Met Val Ala Arg Val Gly Leu Leu Arg Ala Leu Gln Leu Leu Leu
1               5                   10                  15
Trp Gly His Leu Asp Ala Gln Pro Ala Glu Arg Gly Gly Gln Glu Leu
            20                  25                  30
Arg Lys Glu Ala Glu Ala Phe Leu Glu Lys Tyr Gly Tyr Leu Asn Glu
        35                  40                  45
Gln Val Pro Lys Ala Pro Thr Ser Thr Arg Phe Ser Asp Ala Ile Arg
    50                  55                  60
Ala Phe Gln Trp Val Ser Gln Leu Pro Val Ser Gly Val Leu Asp Arg
65                  70                  75                  80
Ala Thr Leu Arg Gln Met Thr Arg Pro Arg Cys Gly Val Thr Asp Thr
                    85                  90                  95
Asn Ser Tyr Ala Ala Trp Ala Glu Arg Ile Ser Asp Leu Phe Ala Arg
                100                 105                 110
His Arg Thr Lys Met Arg Arg Lys Arg Phe Ala Lys Gln Gly Asn
            115                 120                 125
Lys Trp Tyr Lys Gln His Leu Ser Tyr Arg Leu Val Asn Trp Pro Glu
130                 135                 140
His Leu Pro Glu Pro Ala Val Arg Gly Ala Val Arg Ala Ala Phe Gln
145                 150                 155                 160
Leu Trp Ser Asn Val Ser Ala Leu Glu Phe Trp Glu Ala Pro Ala Thr
                165                 170                 175
Gly Pro Ala Asp Ile Arg Leu Thr Phe Phe Gln Gly Asp His Asn Asp
            180                 185                 190
Gly Leu Gly Asn Ala Phe Asp Gly Pro Gly Gly Ala Leu Ala His Ala
        195                 200                 205
Phe Leu Pro Arg Arg Gly Glu Ala His Phe Asp Gln Asp Glu Arg Trp
    210                 215                 220
Ser Leu Ser Arg Arg Arg Gly Arg Asn Leu Phe Val Val Leu Ala His
225                 230                 235                 240
Glu Ile Gly His Thr Leu Gly Leu Thr His Ser Pro Ala Pro Arg Ala
                    245                 250                 255
Leu Met Ala Pro Tyr Tyr Lys Arg Leu Gly Arg Asp Ala Leu Leu Ser
                260                 265                 270
Trp Asp Asp Val Leu Ala Val Gln Ser Leu Tyr Gly Lys Pro Leu Gly
            275                 280                 285
Gly Ser Val Ala Val Gln Leu Pro Gly Lys Leu Phe Thr Asp Phe Glu
        290                 295                 300
```

```
Thr Trp Asp Ser Tyr Ser Pro Gln Gly Arg Arg Pro Glu Thr Gln Gly
305                 310                 315                 320

Pro Lys Tyr Cys His Ser Ser Phe Asp Ala Ile Thr Val Asp Arg Gln
                325                 330                 335

Gln Gln Leu Tyr Ile Phe Lys Gly Ser His Phe Trp Glu Val Ala Ala
            340                 345                 350

Asp Gly Asn Val Ser Glu Pro Arg Pro Leu Gln Glu Arg Trp Val Gly
            355                 360                 365

Leu Pro Pro Asn Ile Glu Ala Ala Val Ser Leu Asn Asp Gly Asp
    370                 375                 380

Phe Tyr Phe Phe Lys Val Gln Ser Val
385                 390

<210> SEQ ID NO 23
<211> LENGTH: 469
<212> TYPE: PRT
<213> ORGANISM: Homo sapiens

<400> SEQUENCE: 23

Lys Ala Pro Thr Ser Thr Arg Phe Ser Asp Ala Ile Arg Ala Phe Gln
1               5                   10                  15

Trp Val Ser Gln Leu Pro Val Ser Gly Val Leu Asp Arg Ala Asn Leu
            20                  25                  30

Arg Gln Met Thr Arg Pro Arg Cys Gly Val Thr Asp Thr Asn Ser Tyr
        35                  40                  45

Ala Ala Trp Ala Glu Arg Ile Ser Asp Leu Phe Ala Arg His Arg Thr
    50                  55                  60

Lys Met Arg Arg Lys Lys Arg Phe Ala Lys Gln Gly Asn Lys Trp Tyr
65                  70                  75                  80

Lys Gln His Leu Ser Tyr Arg Leu Val Asn Trp Pro Glu His Leu Pro
                85                  90                  95

Glu Pro Ala Val Arg Gly Ala Val Arg Ala Ala Phe Gln Leu Trp Ser
            100                 105                 110

Asn Val Ser Ala Leu Glu Phe Trp Glu Ala Pro Ala Thr Gly Pro Ala
        115                 120                 125

Asp Ile Arg Leu Thr Phe Phe Gln Gly Asp His Asn Asp Gly Leu Gly
    130                 135                 140

Asn Ala Phe Asp Gly Pro Gly Gly Ala Leu Ala His Ala Phe Leu Pro
145                 150                 155                 160

Arg Arg Gly Glu Ala His Phe Asp Gln Asp Glu Arg Trp Ser Leu Ser
                165                 170                 175

Arg Arg Arg Gly Arg Asn Leu Phe Val Val Leu Ala His Glu Ile Gly
            180                 185                 190

His Thr Leu Gly Leu Thr His Ser Pro Ala Pro Arg Ala Leu Met Ala
        195                 200                 205

Pro Tyr Tyr Lys Arg Leu Gly Arg Asp Ala Leu Leu Ser Trp Asp Asp
    210                 215                 220

Val Leu Ala Val Gln Ser Leu Tyr Gly Lys Pro Leu Gly Gly Ser Val
225                 230                 235                 240

Ala Val Gln Leu Pro Gly Lys Leu Phe Thr Asp Phe Glu Thr Trp Asp
                245                 250                 255

Ser Tyr Ser Pro Gln Gly Arg Arg Pro Glu Thr Gln Gly Pro Lys Tyr
            260                 265                 270

Cys His Ser Ser Phe Asp Ala Ile Thr Val Asp Arg Gln Gln Gln Leu
```

```
                        275                 280                 285
Tyr Ile Phe Lys Gly Ser His Phe Trp Glu Val Ala Ala Asp Gly Asn
            290                 295                 300
Val Ser Glu Pro Arg Pro Leu Gln Glu Arg Trp Val Gly Leu Pro Pro
305                 310                 315                 320
Asn Ile Glu Ala Ala Val Ser Leu Asn Asp Gly Asp Phe Tyr Phe
                325                 330                 335
Phe Lys Gly Gly Arg Cys Trp Arg Phe Arg Gly Pro Lys Pro Val Trp
            340                 345                 350
Gly Leu Pro Gln Leu Cys Arg Ala Gly Leu Pro Arg His Pro Asp
                355                 360                 365
Ala Ala Leu Phe Phe Pro Pro Leu Arg Arg Leu Ile Leu Phe Lys Gly
            370                 375                 380
Ala Arg Tyr Tyr Val Leu Ala Arg Gly Gly Leu Gln Val Glu Pro Tyr
385                 390                 395                 400
Tyr Pro Arg Ser Leu Gln Asp Trp Gly Gly Ile Pro Glu Glu Val Ser
                405                 410                 415
Gly Ala Leu Pro Arg Pro Asp Gly Ser Ile Ile Phe Phe Arg Asp Asp
            420                 425                 430
Arg Tyr Trp Arg Leu Asp Gln Ala Lys Leu Gln Ala Thr Thr Ser Gly
                435                 440                 445
Arg Trp Ala Thr Glu Leu Pro Trp Met Gly Cys Trp His Ala Asn Ser
            450                 455                 460
Gly Ser Ala Leu Phe
465

<210> SEQ ID NO 24
<211> LENGTH: 520
<212> TYPE: PRT
<213> ORGANISM: Homo sapiens

<400> SEQUENCE: 24

Met Val Ala Arg Val Gly Leu Leu Leu Arg Ala Leu Gln Leu Leu Leu
1               5                   10                  15
Trp Gly His Leu Asp Ala Gln Pro Ala Glu Arg Gly Gly Gln Glu Leu
                20                  25                  30
Arg Lys Glu Ala Glu Ala Phe Leu Glu Lys Tyr Gly Tyr Leu Asn Glu
            35                  40                  45
Gln Val Pro Lys Ala Pro Thr Ser Thr Arg Phe Ser Asp Ala Ile Arg
        50                  55                  60
Ala Phe Gln Trp Val Ser Gln Leu Pro Val Ser Gly Val Leu Asp Arg
65                  70                  75                  80
Ala Thr Leu Arg Gln Met Thr Arg Pro Arg Cys Gly Val Thr Asp Thr
                85                  90                  95
Asn Ser Tyr Ala Ala Trp Ala Glu Arg Ile Ser Asp Leu Phe Ala Arg
                100                 105                 110
His Arg Thr Lys Met Arg Arg Lys Arg Phe Ala Lys Gln Gly Asn
            115                 120                 125
Lys Trp Tyr Lys Gln His Leu Ser Tyr Arg Leu Val Asn Trp Pro Glu
        130                 135                 140
His Leu Pro Glu Pro Ala Val Arg Gly Ala Val Arg Ala Ala Phe Gln
145                 150                 155                 160
Leu Trp Ser Asn Val Ser Ala Leu Glu Phe Trp Glu Ala Pro Ala Thr
                165                 170                 175
```

-continued

```
Gly Pro Ala Asp Ile Arg Leu Thr Phe Phe Gln Gly Asp His Asn Asp
            180                 185                 190

Gly Leu Gly Asn Ala Phe Asp Gly Pro Gly Gly Ala Leu Ala His Ala
            195                 200                 205

Phe Leu Pro Arg Arg Gly Glu Ala His Phe Asp Gln Asp Glu Arg Trp
            210                 215                 220

Ser Leu Ser Arg Arg Arg Gly Arg Asn Leu Phe Val Val Leu Ala His
225                 230                 235                 240

Glu Ile Gly His Thr Leu Gly Leu Thr His Ser Pro Ala Pro Arg Ala
                    245                 250                 255

Leu Met Ala Pro Tyr Tyr Lys Arg Leu Gly Arg Asp Ala Leu Leu Ser
            260                 265                 270

Trp Asp Asp Val Leu Ala Val Gln Ser Leu Tyr Gly Lys Pro Leu Gly
            275                 280                 285

Gly Ser Val Ala Val Gln Leu Pro Gly Lys Leu Phe Thr Asp Phe Glu
            290                 295                 300

Thr Trp Asp Ser Tyr Ser Pro Gln Gly Arg Arg Pro Glu Thr Gln Gly
305                 310                 315                 320

Pro Lys Tyr Cys His Ser Ser Phe Asp Ala Ile Thr Val Asp Arg Gln
                    325                 330                 335

Gln Gln Leu Tyr Ile Phe Lys Gly Ser His Phe Trp Glu Val Ala Ala
            340                 345                 350

Asp Gly Asn Val Ser Glu Pro Arg Pro Leu Gln Glu Arg Trp Val Gly
            355                 360                 365

Leu Pro Pro Asn Ile Glu Ala Ala Val Ser Leu Asn Asp Gly Asp
            370                 375                 380

Phe Tyr Phe Phe Lys Gly Gly Arg Cys Trp Arg Phe Arg Gly Pro Lys
385                 390                 395                 400

Pro Val Trp Gly Leu Pro Gln Leu Cys Arg Ala Gly Gly Leu Pro Arg
                    405                 410                 415

His Pro Asp Ala Ala Leu Phe Phe Pro Pro Leu Arg Arg Leu Ile Leu
                    420                 425                 430

Phe Lys Gly Ala Arg Tyr Tyr Val Leu Ala Arg Gly Gly Leu Gln Val
            435                 440                 445

Glu Pro Tyr Tyr Pro Arg Ser Leu Gln Asp Trp Gly Gly Ile Pro Glu
            450                 455                 460

Glu Val Ser Gly Ala Leu Pro Arg Pro Asp Gly Ser Ile Ile Phe Phe
465                 470                 475                 480

Arg Asp Asp Arg Tyr Trp Arg Leu Asp Gln Ala Lys Leu Gln Ala Thr
                    485                 490                 495

Thr Ser Gly Arg Trp Ala Thr Glu Leu Pro Trp Met Gly Cys Trp His
            500                 505                 510

Ala Asn Ser Gly Ser Ala Leu Phe
            515                 520
```

What is claimed is:

1. An isolated nucleic acid molecule selected from the group consisting of:
    a) a nucleic acid molecule comprising a nucleotide sequence which is at least 95% identical to the nucleotide sequence of SEQ ID NO: 11, wherein the nucleic acid molecule encodes a polypeptide having matrix metalloproteinase activity;
    b) a nucleic acid molecule comprising a fragment of at least 1224 consecutive nucleotide residues of the nucleotide sequence of SEQ ID NO: 11, wherein said consecutive nucleotide residues encode a polypeptide having matrix metalloproteinase activity;
    c) a nucleic acid molecule which encodes a polypeptide comprising the amino acid sequence of SEQ ID NO: 12;
    d) a nucleic acid molecule which encodes a fragment of a polypeptide comprising the amino acid sequence of SEQ ID NO: 12, wherein the fragment comprises at least 150 contiguous amino acids of SEQ ID NO: 12, wherein said at least 150 contiguous amino acids have matrix metalloproteinase activity; and e) a nucleic acid molecule which hybridizes over its full length to the complement of a nucleic acid molecule having a sequence consisting of SEQ ID NO: 11, under conditions of incubation at 45° C. in 6.0× standard saline citrate buffer (SSC) followed by washing in 0.2×SSC, 0.1% SDS at 50° C. to 65° C., wherein the nucleic acid molecule encodes a polypeptide having matrix metalloproteinase activity.

2. The isolated nucleic acid molecule of claim 1, which is selected from the group consisting of:

a) a nucleic acid comprising the nucleotide sequence of SEQ ID NO: 11; and b) a nucleic acid molecule which encodes a polypeptide comprising the amino acid sequence of SEQ ID NO: 12.

3. A vector comprising the nucleic acid molecule of claim 1.

4. The nucleic acid molecule of claim 1 further comprising a nucleic acid sequence encoding a heterologous polypeptide.

5. A host cell that contains the vector of claim 3.

6. The host cell of claim 5, wherein the host cell is a mammalian cell.

7. A method for producing a polypeptide comprising culturing the host cell of claim 5 under conditions in which the nucleic acid molecule is expressed.

8. The host cell of claim 5, wherein the nucleic acid molecule is expressed in the cell.

9. A vector comprising the nucleic acid molecule of claim 4.

10. A host cell that contains the nucleic acid molecule of claim 4.

11. The host cell of claim 10, wherein the nucleic acid molecule is expressed in the cell.

12. The host cell of claim 11, wherein the host cell is a mammalian cell.

13. A method for producing a fusion polypeptide comprising culturing the host cell of claim 10 under conditions in which the nucleic acid molecule is expressed.

14. An isolated nucleic acid molecule comprising a nucleotide sequence which is at least 95% identical to the nucleotide sequence of SEQ ID NO:11, wherein the nucleic acid molecule encodes a polypeptide having matrix metalloproteinase activity.

15. An isolated nucleic acid molecule which encodes a polypeptide comprising the amino acid sequence of SEQ ID NO:12.

16. An isolated nucleic acid molecule which hybridizes over its full length to the complement of a nucleic acid molecule having a sequence consisting of SEQ ID NO:11 under conditions of incubation at 45° C. in 6.0× SSC followed by washing in 0.2× SSC, 0.1% SDS at 50° C. to 65° C., wherein the nucleic acid molecule encodes a polypeptide having matrix metalloproteinase activity.

* * * * *